(12) United States Patent
Dehesh

US007301070B2

(10) Patent No.: US 7,301,070 B2
(45) Date of Patent: Nov. 27, 2007

(54) PLANT FATTY ACID SYNTHASES AND USE IN IMPROVED METHODS FOR PRODUCTION OF MEDIUM-CHAIN FATTY ACIDS

(75) Inventor: Katayoon Dehesh, Vacaville, CA (US)

(73) Assignee: Calgene LLC, Davis, CA (US)

( * ) Notice: Subject to any disclaimer, the term of this patent is extended or adjusted under 35 U.S.C. 154(b) by 595 days.

(21) Appl. No.: 10/635,822

(22) Filed: Aug. 7, 2003

(65) Prior Publication Data

US 2004/0068765 A1 Apr. 8, 2004

Related U.S. Application Data

(62) Division of application No. 09/057,996, filed on Apr. 9, 1998, now Pat. No. 6,660,849.

(60) Provisional application No. 60/041,815, filed on Apr. 11, 1997.

(51) Int. Cl.
*C12N 15/82* (2006.01)
*A01H 5/00* (2006.01)
(52) U.S. Cl. .................... 800/281; 800/298
(58) Field of Classification Search .............. None
See application file for complete search history.

(56) References Cited

U.S. PATENT DOCUMENTS 5,585,535 A 12/1996 Fehr et al.
6,426,447 B1 * 7/2002 Knauf et al. ............... 800/281

FOREIGN PATENT DOCUMENTS

| EP | 0 969 014 | 1/2000 |
|---|---|---|
| WO | 92/03564 | 3/1992 |
| WO | 92/20236 | 11/1992 |
| WO | 93/10240 | 5/1993 |
| WO | 94/10189 | 5/1994 |
| WO | 94/10288 | 5/1994 |
| WO | 95/06740 | 3/1995 |
| WO | 96/23892 | 8/1996 |
| WO | 98/46766 | 10/1998 |
| WO | 95/15387 | 6/1999 |
| WO | 00/07433 | 2/2000 |
| WO | 00/75343 | 12/2000 |
| WO | 01/29238 | 4/2001 |

OTHER PUBLICATIONS

Clough et al., "Purification and Characterization of 3-Ketoacyl-Acyl Carrier Protein Synthase III from Spinach", *The Journal of Biological Chemistry*, 267(29):20992-20998 (1992).
Dehesh et al., Database EMBL, Accession No. AX073486 (XP002213168) (2001).
Dehesh et al., "GT-2: A Transcription Factor with Twin Autonomous DNA-Binding Domains of Closely Related but Different Target Sequence Specificity", *The EMBO Journal*, 11(11):4131-4144 (1992).

Dehesh, "KAS IV: 3-Ketoacyl-ACP Synthase from *Cuphea sp*. is a Medium Chain Specific Condensing Enzyme", *The Plant Journal*, 15(3):383-390 (1998).
Dehesh et al., "Production of High Levels of 8:0 and 10:0 Fatty Acids in Transgenic Canola by Overexpression of CH FatB2, a Thioesterase cDNA from *Cuphea hookerinana*", *The Plant Journal*, 9(2):167-172 (1996).
Dehesh et al., "Two Novel Thioesterases are Key Determinants of the Bimodal Distribution of Acyl Chain Length of *Cuphea palustris* Seed Oil", *Plant Physiol.*, 110:203-210 (1996).
Eccleston et al., "Expression of Lauroyl-Acyl Carrier Protein Thioesterase in *Brassica napus* Seeds Induces Pathways for Both Fatty Acid Oxidation and Biosynthesis and Implies a Set Point for Triacylglycerol Accumulation", *The Plant Cell*, 10:613-621 (1998).
Fuhrmann et al., "Factors Controlling Medium-Chain Fatty Acid Synthesis in Plastids from Maturing *Cuphea* Embryos", *Z. Naturforsch*, 48c:616-622 (1993).
Harwood, "Fatty Acid Metabolism", *Ann. Rev. Plant Physiol. Plant Mol. Biol.*, 39:101-138 (1988).
Hawkins et al., "Characterization of acyl-ACP Thioesterases of Mangosteen (*Garcinia mangostana*) Seed and High Levels of Stearate Production in Transgenic Canola", *The Plant Journal*, 13(6):743-752 (1998).
International Search Report, PCT/US01/23369 dated Sep. 25, 2002 (4 pages).
Jaworski et al., "A Cerulenin Insensitive Short Chain 3-Ketoacyl-Acyl Carrier Protein Synthase in *Spinacia oleracea* Leaves", *Plant Physiology*, 90:41-44 (1989).
Kaneko et al., Database EMBL, Accession No. D90905 (XP002213167) (1996).
Kaneko et al., "Sequence Analysis of the Genome of the Unicellular Cyanobacterium *Synechocystis sp*. Strain PCC6803 II. Sequence Determination of the Entire Genome and Assignment of Potential Protein-coding Regions", *DNA Research*, 3:109-136 (1996).
Kauppinen, "Structure and Expression of the Kas12 Gene Encoding a β-Ketoacyl-Acyl Carrier Protein Synthase Iisozyme from Barley", *The Journal of Biological Chemistry*, 267(33):23999-24006 (1992).
Leonard et al., "A Cuphea β-Ketoacyl-ACP Synthase Shifts the Synthesis of Fatty Acids towards Shorter Chains in *Arabidopsis* Seeds Expressing Cuphea FatB Thioesterases", *The Plant Journal* 13(5):621-628 (1998).

(Continued)

Primary Examiner—Elizabeth F. McElwain
(74) *Attorney, Agent, or Firm*—Chunping Li; Arnold & Porter LLP

(57) ABSTRACT

By this invention, compositions and methods of use related to β-ketoacyl-ACP synthase Of special interest are synthases obtainable from *Cuphea* species. Amino acid and nucleic acid for synthase protein factors are provided, as well as methods to utilize such sequences in constructs for production of genetically engineered plants having altered fatty acid compositions. Of particular interest is the expression of synthase protein factors in conjunction with expression of plant medium-chain acyl-ACP thioesterases for production of increased levels and/or modified ratios of medium-chain fatty acids in oils of transgenic plant seeds.

5 Claims, 60 Drawing Sheets

OTHER PUBLICATIONS

Martini, "Modification of Fatty Acid Composition in the Storage Oil of Transgenic Rapeseed", *Biological Chemistry Hoppe-Seyler*, vol. 376, pp. S55 (1995).

Ohlrogge, "Design of New Plant Products: Engineering of Fatty Acid Metabolism", *Plant Physiol.*, 104:821-826 (1994).

Post-Beittenmiller et al., "In vivo Pools of Free and Acylated Acyl Carrier Proteins in Spinach", *The Journal of Biological Chemistry*, 266(3):1858-1865 (1991).

Radke et al., "Transformation of *Brassica napus* L. Using *Agrobacterium Tumefaciens*: Developmentally Regulated Expression of a Reintroduced Napin Gene", *Theor. Appl. Genet.* 75:685-694 (1988).

Schuch et al., "Medium-chain acyl-ACP Thioesterase is not the Exclusive Enzyme Responsible for Early Chain-Length Termination in Medium-Chain Fatty Acid Synthesis", *Grasas y. Aceites*, vol. 44, Fasc 2, pp. 126-128 (1993).

Shimakata et al., "Isolation and Function of Spinach Leaf β-Ketoacyl-(Acyl-Carrier-Protein) Synthases", *Proceedings of National Academy of Science*, USA, 79:5808-5812 (1982).

Siggard-Andersen et al., "The fabJ-Encoded β-Ketoacyl-(Acyl Carrier Protein) Synthase IV from *Escherichia coli* is Sensitive to Cerulenin and Specific for Short -Chain Substrates", Proc. Natl. Acad. Sci., USA, 91:11027-11031 (1994).

Slabaugh et al., "Condensing Enzymes from *Cuphea wrightii* Associated with Medium Chain Fatty Acid Biosynthesis", *The Plant Journal*, 13(5):611-620 (1998).

Slabaugh et al., GenEMBL Sequence Accession No. U67317 (1996).

Slabaugh et al., "cDNA Clones Encoding β-Ketoacyl-Acyl Carrier Protein Synthase III from *Cuphea wrightii*", Plant Physiology, 108:443-444 (1995).

Tai et al., "3-Ketoacyl-Acyl Carrier Protein Synthase III from Spinach (*Spinacia oleracea*) is not Similar to Other Condensing Enzymes of Fatty Acid Synthase", *Plant Physiology*, 103:1361-1367 (1993).

Töpfer et al., "Modification of Plant Lipid Synthesis", *Science*, 268:681-685 (1995).

Tsay et al., "Isolation and Characterization of the β- Ketoacyl-Acyl Carrier Protein Synthase III Gene (fabH) from *Escherichia coli* K12", 267(10):6807-6814 (1992).

Voelker et al., "Genetic Engineering of a Quantitative Trait: Metabolic and Genetic Parameters Influencing the Accumulation of Laurate in Rapeseed", *The Plant Journal*, 9(2):229-241 (1996).

Voelker et al., "Plant Acyl-ACP Thioesterases: Chain-Length Determining Enzymes in Plant Fatty Acid Biosynthesis", *Genetic Engineering*, 18:111-133 (1996).

Voelker et al., "Fatty Acid Biosynthesis Redirected to Medium-Chains in Transgenic Oilseed Plants", *Science*, 257:72-74 (1992).

Walsh et al., "The Short Chain Condensing Enzyme has a Widespread Occurrence in the Fatty Acid Synthetases from Higher Plants", *Phytochemistry*, 29(12):3797-3799 (1990).

Winter et al., "Decarboxylation of Malonyl-(Acyl Carrier Protein) by 3-Oxoacyl-)Acyl Carrier Protein) Synthases in Plant Fatty Acid Biosynthesis", *Biochem. J.*, 321:313-318 (1997).

McKeon et al., "Purification and Characterization of the Stearoyl-Acyl Carrier Protein Desaturase and the Acyl-Acyl Carrier Protein Thioesterase from Maturing Seeds of Safflower", *The Journal of Biological Chemistry*, 257(20):12141-12147 (1982).

DATABASE EMBL Accession No. U24177 dated Apr. 29, 1995.

European Search Report issued Feb. 27, 2007 in EP 05 10 5986.

Siggaard-Andersen et al., "Primary structure of a cerulenin-binding β-Ketoacyl-[acyl carrier protein] synthase from barley chloroplasts", Proc. Natl. Acad. Sci. USA, 88:4114-418 (1991).

\* cited by examiner

```
AGC TCC ACC GCG GTG GCG GCC GCT CTA GAA CTA GTG GAT CCC CCG GGC    48
Ser Ser Thr Ala Val Ala Ala Ala Leu Glu Leu Val Asp Pro Pro Gly

TGC AGG AAT TCG GCA CGA GCC GAT CTC GGT GCC GAC CGC CTC TCC AAG    96
Cys Arg Asn Ser Ala Arg Ala Asp Leu Gly Ala Asp Arg Leu Ser Lys

ATC GAC AAG GAG AGA GCC GGA GTG CTG GGA ACA GGA ATG GGT GGT       144
Ile Asp Lys Glu Arg Ala Gly Val Leu Gly Thr Gly Met Gly Gly

CTG ACT GTC TTC TCT GAC GGG GTT CAG TCT CTT ATC GAG AAG GGT CAC   192
Leu Thr Val Phe Ser Asp Gly Val Gln Ser Leu Ile Glu Lys Gly His

CGG AAA ATC ACC CCT TTC TTC ATC CCC TAT GCC ATT ACA AAC ATG GGG   240
Arg Lys Ile Thr Pro Phe Phe Ile Pro Tyr Ala Ile Thr Asn Met Gly

TCT GCC CTG CTC GCT ATC GAA TTT GGT CTC ATG GGC CCA AAC TAT TCA   288
Ser Ala Leu Leu Ala Ile Glu Phe Gly Leu Met Gly Pro Asn Tyr Ser

ATT TCC ACT GCA TGT GCC ACT TCC AAC TAC TGC TTC CAT GCT GCC GCT   336
Ile Ser Thr Ala Cys Ala Thr Ser Asn Tyr Cys Phe His Ala Ala Ala

AAT CAT ATC CGC CGT GGT GAG GCT GAT CTT ATG ATT GCT GGA GGC ACT   384
Asn His Ile Arg Arg Gly Glu Ala Asp Leu Met Ile Ala Gly Gly Thr
```

FIGURE 1

| | | | | | | | |
|---|---|---|---|---|---|---|---|
| GAG | GCC | GCA | ATC | ATT | CCA | ATT | GGG | TTG | GGA | GGC | TTT | GTG | GCT | TGC | AGG | 432 |
| Glu | Ala | Ala | Ile | Ile | Pro | Ile | Gly | Leu | Gly | Gly | Phe | Val | Ala | Cys | Arg | |
| GCT | TTG | TCT | CAA | AGG | AAC | GAT | GAC | CCG | CAG | ACT | GCC | TCT | AGG | CCC | TGG | 480 |
| Ala | Leu | Ser | Gln | Arg | Asn | Asp | Asp | Pro | Gln | Thr | Ala | Ser | Arg | Pro | Trp | |
| GAT | AAA | GAC | CGT | GAT | GGT | TTT | GTG | ATG | GGT | GAA | GGT | GCT | GGA | GTG | TTG | 528 |
| Asp | Lys | Asp | Arg | Asp | Gly | Phe | Val | Met | Gly | Glu | Gly | Ala | Gly | Val | Leu | |
| GTG | ATG | GAG | AGC | TTG | GAA | CAT | GCA | ATG | AGA | CGA | GGA | GCA | CCG | ATT | ATT | 576 |
| Val | Met | Glu | Ser | Leu | Glu | His | Ala | Met | Arg | Arg | Gly | Ala | Pro | Ile | Ile | |
| GCA | GAG | TAT | TTG | GGA | GGT | GCA | ATC | AAC | TGT | GAT | GCT | TAT | CAC | ATG | ACT | 624 |
| Ala | Glu | Tyr | Leu | Gly | Gly | Ala | Ile | Asn | Cys | Asp | Ala | Tyr | His | Met | Thr | |
| GAT | CCA | AGG | GCT | GAT | GGT | CTT | GGT | GTC | TCT | TGC | ATT | GAG | AGT | AGC | 672 |
| Asp | Pro | Arg | Ala | Asp | Gly | Leu | Gly | Val | Ser | Ser | Cys | Ile | Glu | Ser | Ser | |
| CTT | GAA | GAT | GCT | GGC | GTC | TCA | CCT | GAA | GAG | GTC | AAT | TAC | ATA | AAT | GCT | 720 |
| Leu | Glu | Asp | Ala | Gly | Val | Ser | Pro | Glu | Glu | Val | Asn | Tyr | Ile | Asn | Ala | |

FIGURE 1

CAT GCG ACT TCT ACT CTA GCT GGG GAT CTC GCC GAG ATA AAT GCC ATC   768
His Ala Thr Ser Thr Leu Ala Gly Asp Leu Ala Glu Ile Asn Ala Ile

AAG AAG GTT TTC AAG AAC ACA AAG GAT ATC AAA ATT AAT GCA ACT AAG   816
Lys Lys Val Phe Lys Asn Thr Lys Asp Ile Lys Ile Asn Ala Thr Lys

TCA ATG ATC GGA CAC TGT CTT GGA GCA TCT GGA GGT CTT GAA GCT ATA   864
Ser Met Ile Gly His Cys Leu Gly Ala Ser Gly Gly Leu Glu Ala Ile

GCG ACT ATT AAG GGA ATA AAC ACC GGC TGG CTT CAT CCC AGC ATT AAT   912
Ala Thr Ile Lys Gly Ile Asn Thr Gly Trp Leu His Pro Ser Ile Asn

CAA TTC AAT CCT GAG CCA TCG GTG GAG TTC GAC ACT GTT GCC AAC AAG   960
Gln Phe Asn Pro Glu Pro Ser Val Glu Phe Asp Thr Val Ala Asn Lys

AAG CAG CAA CAC GAA GTT AAC GTT GCG ATC TCA AAT TCA TTC GGA TTT  1008
Lys Gln Gln His Glu Val Asn Val Ala Ile Ser Asn Ser Phe Gly Phe

GGA GGC CAC AAC TCA GTC GTG GCT TTC TCG GCT TTC AAG CCA TGATTA   1056
Gly Gly His Asn Ser Val Val Ala Phe Ser Ala Phe Lys Pro

FIGURE 1

```
CCCATTTCAC AAGGTACTTG TCATTGAGAA TACGGATTAT GGACTTGCAG AGTAATTTCC    1116
CCATGTTTGT CGGAAGAGCA TATTACCACG GTTGTCCGTC AAACCCATTT AGGATACTGT    1176
TCTATGTAAT AAACTAAGG  ATTATTAATT TCCCTTTTAA TCCTGTCTCC AGTTTGAGCA    1236
TGAATTATA  TTTATTTTAT CTTAGAAAGG TCAAATAAGA TTTTGTTTTA CCTCTGTAAA    1296
ACTTTGTTT  GTATTGGAAA GGAAGTGCCG TCTCAAAAA  AAAAAAAA AA              1340
```

FIGURE 1

Sequence Range: 1 to 1704

```
         10              20              30           40
AAA TTA ACC CTC ACT AAA GGG AAC AAA AGC TGG AGC TCC ACC GNG GTG
Lys Leu Thr Leu Thr Lys Gly Asn Lys Ser Trp Ser Ser Thr Xxx Val>
 50              60              70              80              90
GCG GCC GCT CTA GAA CTA GTG GAT CCC CCG GGC TGC AGG AAT TCG GCA
Ala Ala Ala Leu Glu Leu Val Asp Pro Pro Gly Cys Arg Asn Ser Ala>
        100             110             120             130             140
CGA GCC GGC ATG GGC CTC GTC TCC GTA TTC TCC GAC GTC GAC TCT
Arg Ala Gly Met Gly Leu Val Ser Val Phe Gly Ser Asp Val Asp Ser>
       150             160             170             180             190
TAT TAC GAA AAG CTC CTC TCC GGC GAG AGC GGG ATC AGC TTA ATC GAC
Tyr Tyr Glu Lys Leu Leu Ser Gly Glu Ser Gly Ile Ser Leu Ile Asp>
       200             210             220             230             240
CGC TTC GAC GCT TCC AAG TTC CCC ACC AGG TTC GGC CAG ATC CGG
Arg Phe Asp Ala Ser Lys Phe Pro Thr Arg Phe Gly Gln Ile Arg>
       250             260             270             280
GGA TTC AAC GCG ACG GGA TAC ATC GAC TAC GGG AAG AAC GAC AGG AGG CTC
Gly Phe Asn Ala Thr Gly Tyr Ile Asp Tyr Gly Lys Asn Asp Arg Arg Leu>
 90            300             310             320             330
GAC GAT TGC CTC CGC TAC TGC ATT GTC GCC GGG AAG AAG GCT CTC GAA
Asp Asp Cys Leu Arg Tyr Cys Ile Val Ala Gly Lys Lys Ala Leu Glu>
```

FIGURE 2

```
340                350                360                370                380
AAT TCC GAT CTC GGC GGT GAA AGC CTC TCC AAG ATT GAT AAG GAG AGA
Asn Ser Asp Leu Gly Gly Glu Ser Leu Ser Lys Ile Asp Lys Glu Arg>
     390                400                410                420                430
GCT GGA GTG CTA GTT GGA ACT GGT ATG GGT GGC CTA ACC GTC TTC TCT
Ala Gly Val Leu Val Gly Thr Gly Met Gly Gly Leu Thr Val Phe Ser>
          440                450                460                470                480
GAC GGG GTT CAG AAT CTC ATC GAG AAA GGT CAC CGG AAG ATC TCC CCG
Asp Gly Val Gln Asn Leu Ile Glu Lys Gly His Arg Lys Ile Ser Pro>
               490                500                510                520
TTT TTC ATT CCC TAT GCC ATT ACA AAC ATG GGG TCT GCT CTG CTT GCC
Phe Phe Ile Pro Tyr Ala Ile Thr Asn Met Gly Ser Ala Leu Leu Ala>
     30                540                550                560                570
ATC GAT TTG GGT CTG ATG GGC CCA AAC TAT TCG ATT TCA ACT GCA TGT
Ile Asp Leu Gly Leu Met Gly Pro Asn Tyr Ser Ile Ser Thr Ala Cys>
          580                590                600                610                620
GCT ACT TCC AAC TAC TGC TTT TAT GCC GCT AAT CAT ATC CGC CGA
Ala Thr Ser Asn Tyr Cys Phe Tyr Ala Ala Asn His Ile Arg Arg>
               630                640                650                660                670
GGC GAG GCT GAC CTC ATG ATT GCT GGA ACT GAG GCT GCA ATC ATT
Gly Glu Ala Asp Leu Met Ile Ala Gly Thr Glu Ala Ala Ile Ile>
```

FIGURE 2

```
                                              710                    760
680            690            700                    740    750                     810
       CCA ATT GGG TTA GGA GGA TTC GTT GCC TGC AGG GCT TTA TCT CAA AGG
       Pro Ile Gly Leu Gly Gly Phe Val Ala Cys Arg Ala Leu Ser Gln Arg>

AAT GAT GAC CCT CAG ACT GCC TCA AGG CCG TGG GAT AAG GAC CGT GAT
       Asn Asp Asp Pro Gln Thr Ala Ser Arg Pro Trp Asp Lys Asp Arg Asp>

770            780                                                   860
                      790            800            850    
       GGT TTT GTG ATG GGC GAA GGG GCT GGA GTA TTG GTT ATG GAG AGC TTG
       Gly Phe Val Met Gly Glu Gly Ala Gly Val Leu Val Met Glu Ser Leu>

820            830            840            890    900            910
       GAA CAT GCA ATG AAA CGA GGA GCG CCG ATT ATT GCA GAA TAT TTG GGA
       Glu His Ala Met Lys Arg Gly Ala Pro Ile Ile Ala Glu Tyr Leu Gly>

870            880                                                   960
       GGT GCA GTC AAT TGT GAT GCT TAT CAT ATG ACT GAT CCA AGG GCT GAT
       Gly Ala Val Asn Cys Asp Ala Tyr His Met Thr Asp Pro Arg Ala Asp>

920            930            940            950    
       GGG CTT GGT GTC TCC TCT TGC ATT GAG AGC AGT CTG GAA GAT GCT GGG
       Gly Leu Gly Val Ser Ser Cys Ile Glu Ser Ser Leu Glu Asp Ala Gly>

970            980            990            1000
       GTC TCA CCT GAA GAG GTC AAT TAC ATA AAT GCT CAT GCG ACT TCC ACT
       Val Ser Pro Glu Glu Val Asn Tyr Ile Asn Ala His Ala Thr Ser Thr>
```

FIGURE 2

```
 10         1020        1030        1040        1050
             *
CTT GCT GGG GAT CTT GCC GAG ATA AAT GCC ATC AAG AAG GTT TTC AAG
Leu Ala Gly Asp Leu Ala Glu Ile Asn Ala Ile Lys Lys Val Phe Lys>

1060        1070        1080        1090        1100
                          *
AAC ACC AAG GAA ATC ACA ATC AAT GCA ACT AAG TCG ATG ATC GGA CAC
Asn Thr Lys Glu Ile Thr Ile Asn Ala Thr Lys Ser Met Ile Gly His>

1110        1120        1130        1140        1150
                                      *
TGT CTT GGA GCA TCA GGG GGT CTT GAA GCC ATT GCA ACA ATT AAG GGA
Cys Leu Gly Ala Ser Gly Gly Leu Glu Ala Ile Ala Thr Ile Lys Gly>

1160        1170        1180        1190        1200
                                                  *
ATA ACC ACC GGC TGG CTT CAT CCC AGC ATA AAC CAA TTC AAT CCC GAG
Ile Thr Thr Gly Trp Leu His Pro Ser Ile Asn Gln Phe Asn Pro Glu>

1210        1220        1230        1240
CCA TCA GTG GAA TTC GAC ACA GTT GCC AAC AAG AAG CAG CAA CAT GAA
Pro Ser Val Glu Phe Asp Thr Val Ala Asn Lys Lys Gln Gln His Glu>

50          1260        1270        1280        1290
             *
GTG AAT GTT GCT ATC TCA AAT TCA TTC GGA TTC GGA GGC CAC AAC TCA
Val Asn Val Ala Ile Ser Asn Ser Phe Gly Phe Gly Gly His Asn Ser>

1300        1310        1320        1330        1340
                          *
GTT GTA GCT TTC TCA GCC TTC AAG CCA TGA TTA CTC GGT TCA AAT GCA
Val Val Ala Phe Ser Ala Phe Lys Pro

FIGURE 2
```

```
AATTGTTGC TGAGACAGTG AGCTTCAACT TGCAGAGCAA TTTTTTACAT GCCTTGTCGT
CGGAAGAGCG TAATACCGGG ATAGTTCCTT GATAGTTCAT TTAAGGATGTT TTACTGCAAT
AATCGAAGAT TATTTCCATT CTAATCCAGT CTCCGNCGAG TTTGAGAATC TATCTGTTTG
TATTAGAAAG AACGAGGCAA GATTTGTTT CATGTTTGTG TTTGTAATAC TTTCTTTTG
CCCTGTCAA TGGCATTTAA GATAAGCTTA TAAAAAAA AAAACTGAG
GGGGGCCCG GTACCCAAT CGCCCTATAG TGAGTCGTAT GACAATTCAC TGTCCGTCGG
```

*FIGURE 2*

Sequence Range: 1 to 2046

```
              10         20         30         40         50         60
                                                                       *
                     ACTAAGGGA ACAAAGCTG GAGCTCCACC GCGGTGGCGG CCGCTCTAGA ACTAGTGGAT 70         80         90        100        110        120
                                                                       *
         CCCCCGGGCT GCAGGAATTC GGCACGAGTT TCTTACTTG GGTCGGCTCA GCTCAGGTGT 130        140        150        160
                                              *
         TCCA ATG GCG ACC GCT TCT TGC ATG GTT GCG TCC CCT TTC TGT ACG TGG
              Met Ala Thr Ala Ser Cys Met Val Ala Ser Pro Phe Cys Thr Trp 170        180        190        200        210
                    *
         CTC GTA GCT GCA TGC ATG CCA ACT TCA TCC GAC AAC GAC CCA CGT TCC
         Leu Val Ala Ala Cys Met Pro Thr Ser Asp Asn Asp Pro Arg Ser 220        230        240        250        260
                                       *
         CTT TCC CAC AAG CGG CTC CGC CTC TCC CGT CGC CGG AGG ACT CTC TCC
         Leu Ser His Lys Arg Leu Arg Leu Ser Arg Arg Arg Arg Thr Leu Ser 270        280        290        300        310
                                                  *
         TCC CAT TGC TCC CTC CGC TTC CAA TGC CTC GAT CCT TGC
         Ser His Cys Ser Leu Arg Gly Ser Thr Phe Gln Cys Leu Asp Pro Cys 320        330        340        350        360
                                                                  *
         AAC CAG CAA CGC TTC CTC GGG GAT AAC GGA TTC GCT TCC CTC TTC GGA
         Asn Gln Gln Arg Phe Leu Gly Asp Asn Gly Phe Ala Ser Leu Phe Gly
```

FIGURE 3

```
                               380            390            400
TCC AAG CCT CTT CGT TCA AAT CGC GGC CAC CTG AGG CTC GGC CGC ACT
Ser Lys Pro Leu Arg Ser Asn Arg Gly His Leu Arg Leu Gly Arg Thr
410            420            430            440            450
TCC CAT TCC GGG GAG GTC ATG GCT GTG CAA CCT GCA CAG GAA
Ser His Ser Gly Glu Val Met Ala Val Gln Pro Ala Gln Glu
460            470            480            490            500
GTC TCC ACA AAT AAG AAA CCT GCT ACC AAG CAA AGG CGA GTA GTT GTG
Val Ser Thr Asn Lys Lys Pro Ala Thr Lys Gln Arg Arg Val Val Val
510            520            530            540            550
ACA GGT ATG GGC GTG GTG ACT CCT CTA GGC CAT GAC CCC GAT GTT TAC
Thr Gly Met Gly Val Val Thr Pro Leu Gly His Asp Pro Asp Val Tyr
560            570            580            590            600
TAC AAC AAT CTC CTA GAC GGA ATA AGT GGC ATA AGT GAG ATA GAG AAC
Tyr Asn Asn Leu Leu Asp Gly Ile Ser Gly Ile Ser Glu Ile Glu Asn
610            620            630            640
TTC GAC TGC TCT CAG TTT CCC ACG AGA ATT GCC GGA GAG ATC AAG TCT
Phe Asp Cys Ser Gln Phe Pro Thr Arg Ile Ala Gly Glu Ile Lys Ser
650            660            670            680            690
TTT TCC ACA GAT GGC TGG GTG GCC CCA AAG TTC TCC GAG AGG ATG GAC
Phe Ser Thr Asp Gly Trp Val Ala Pro Lys Phe Ser Glu Arg Met Asp
```

FIGURE 3

```
700
       AAG TTC ATG CTT TAC ATG CTG ACT GCA GGC AAG AAA GCA TTA GCA GAT
       Lys Phe Met Leu Tyr Met Leu Thr Ala Gly Lys Lys Ala Leu Ala Asp
              710         720         730         740
                           *
750                                             790
       GGT GGA ATC ACT GAA GAT GCG ATG AAA GAG CTC AAT AAA AGA AAG TGT
       Gly Gly Ile Thr Glu Asp Ala Met Lys Glu Leu Asn Lys Arg Lys Cys
              760         770         780                     840
                                       *                       *
800                                             830
       GGA GTT CTC ATT GGC TCC GGA TTG GGC GGT ATG AAG GTA TTC AGC GAT
       Gly Val Leu Ile Gly Ser Gly Leu Gly Gly Met Lys Val Phe Ser Asp
              810         820                     880

850                                             870
       TCC ATT GAA GCT CTG AGG ACT TCA TAT AAG AAG ATC AGT CCC TTT TGT
       Ser Ile Glu Ala Leu Arg Thr Ser Tyr Lys Lys Ile Ser Pro Phe Cys
              860                     870         930

890                                             920
       GTA CCT TTT TCT ACC ACA AAT ATG GGA TCC GCT ATT CTT GCA ATG GAC
       Val Pro Phe Ser Thr Thr Asn Met Gly Ser Ala Ile Leu Ala Met Asp
900                     910                     970         980
       *                                         *
940                                             960
       TTG GGA TGG ATG GGC CCT AAC TAT TCG ATA TCA ACT GCC TGT GCA ACA
       Leu Gly Trp Met Gly Pro Asn Tyr Ser Ile Ser Thr Ala Cys Ala Thr
              950
```

FIGURE 3

```
                           1010              1020            1030
     990         1000        *                 *
AGT AAC TTC TGT ATA CTG AAT GCT GCG AAC CAC ATA ATC AAA GGC GAA
Ser Asn Phe Cys Ile Leu Asn Ala Ala Asn His Ile Ile Lys Gly Glu 1040        1050        1060        1070            1080
                                                               *
GCA GAC ATG ATG CTT TGT GGT GGC TCG GAT GCG GCC GTT TTA CCT GTT
Ala Asp Met Met Leu Cys Gly Gly Ser Asp Ala Ala Val Leu Pro Val 1090        1100        1110        1120
GGT TTG GGA GGT TTC GTA GCA TGC CGA GCT TTG TCA CAG AGG AAT AAT
Gly Leu Gly Gly Phe Val Ala Cys Arg Ala Leu Ser Gln Arg Asn Asn 1130        1140        1150        1160        1170
         *
GAC CCT ACC AAA GCT TCG AGA CCA TGG GAC AGT AAT CGT GAT GGA TTT
Asp Pro Thr Lys Ala Ser Arg Pro Trp Asp Ser Asn Arg Asp Gly Phe 1180        1190        1200        1210        1220
                             *
GTG ATG GGA GAA GGA GCT GGA GCA GTT CTT CTT GAG GAG TTA GAG CAT
Val Met Gly Glu Gly Ala Gly Ala Val Leu Leu Glu Glu Leu Glu His 1230        1240        1250        1260        1270
                                       *
GCA AAG AAA AGA GGT GCA ACC ATT TAT GCG GAA TTT CTA GGT GGG AGT
Ala Lys Lys Arg Gly Ala Thr Ile Tyr Ala Glu Phe Leu Gly Gly Ser 1280        1290        1300        1310            1320
                                                      *
TTC ACT TGC GAC GCC TAC CAC ATG ACC GAG CCT CAC CCT GAA GGA GCT
Phe Thr Cys Asp Ala Tyr His Met Thr Glu Pro His Pro Glu Gly Ala
```

FIGURE 3

```
            1330                1340                1350                1360
GGT GTG ATC CTC TGC ATA GAG AAG GCC TTG GCT CAG TCC GGA GTC TCG
Gly Val Ile Leu Cys Ile Glu Lys Ala Leu Ala Gln Ser Gly Val Ser
1370           1380                1390                1400                1410
AGG GAA GAC GTA AAT TAC ATA AAT GCG CAT GCA ACT TCC ACT CCT GCT
Arg Glu Asp Val Asn Tyr Ile Asn Ala His Ala Thr Ser Thr Pro Ala
        1420                1430                1440                1450                1460
GGA GAT ATC AAG GAA TAC CAA GCT CTC GCC CAC TGT TTC GGC CAA AAC
Gly Asp Ile Lys Glu Tyr Gln Ala Leu Ala His Cys Phe Gly Gln Asn
1470           1480                1490                1500                1510
AGT GAG CTG AGA GTG AAT TCC ACC AAA TCG ATG ATC GGT CAC CTT CTT
Ser Glu Leu Arg Val Asn Ser Thr Lys Ser Met Ile Gly His Leu Leu
        1520                1530                1540                1550                1560
GGA GCT GGT GGC GTA GAA GCA GTT CAG GCA ATA AGG
Gly Gly Ala Gly Gly Val Glu Ala Val Gln Ala Ile Arg
1570           1580                1590                1600
ACA GGA TGG ATC CAT CCA AAT ATT AAT TTG GAA GAC CCG GAC GAA GGC
Thr Gly Trp Ile His Pro Asn Ile Asn Leu Glu Asp Pro Asp Glu Gly
1610           1620                1630                1640                1650
GTG GAT GCA AAA CTG CTC GTC GGC CCT AAG AAG GAG AAA CTG AAG GTC
Val Asp Ala Lys Leu Leu Val Gly Pro Lys Lys Glu Lys Leu Lys Val

FIGURE 3
```

```
1660          1670          1680          1690          1700
AAG GTC GGT TTG TCC AAT TCA TTT GGG TTC GGC GGC CAT AAC TCA TCC
Lys Val Gly Leu Ser Asn Ser Phe Gly Phe Gly Gly His Asn Ser Ser
         1710          1720          1730          1740          1750          1760
ATA CTA TTT GCC CCC TGC AAC TAG A AAAGAGTCTG TGGAAGCCGA GAGTCTTTGA
Ile Leu Phe Ala Pro Cys Asn ***
        1770       1780       1790       1800       1810       1820
GAACTCATGC ACGTTAGTAG CTTCTTATGC CTCTGAAACC GAGATAGACC GGCTACTCGA
        1830       1840       1850       1860       1870       1880
GGGGATGCCA AAGATACTCC TTGCCGGTAT TGGTGTTAAG AGATCACTGC TTGTCCCTTT
        1890       1900       1910       1920       1930       1940
TATTTCTTC TTCTTTTGAG AGCTTTAACC GAGGTAGTCG TATTTTCGAG CTTTTCGAAT
        1950       1960       1970       1980       1990       2000
ACATGTTCGT TATCGGATCA ATGTGTTTCT TCTAAGATCA TTTGTAATGC ATATTTGAA
        2010       2020       2030       2040
AAACCACATC TCAGTATGCA AAATAAAAA AAAAAAAAA AAAAA
```

FIGURE 3

Sequence Range: 1 to 1921

```
                                                                    60
CGGCACGAGG TCACCTCTTA CCTCGCCTGC TTCGAGCCCT GCCATGACTA CTACACCTCC
                                                                   120
GCATCCTTGT TCGGATCCAG GCCCATCCGC ACCACCCGCA GGCACCGGAG GCTCAATCGA
                                                                   180
GCTTCCCCTT CCGGGGAGGC AATGGCTGTG GCTCTGCAAC CTGCACAGGA AGTTACCACA
                                                                   220
AAG AAG AAG CCA AGT ATC AAA CAG CGG GTA GTT GTG ACT GGA ATG
Lys Lys Lys Pro Ser Ile Lys Gln Arg Val Val Val Thr Gly Met>
                                                                   270
GGT GTG GTG ACT CCT CTA GGC CAT GAC CCT GAT GTT TTC TAC AAT AAT
Gly Val Val Thr Pro Leu Gly His Asp Pro Asp Val Phe Tyr Asn Asn>
                                                                   320
CTG CTT GAT GGA ACG AGT GGC ATA AGT GAG ATA GAG ACC TTT GAT TGT
Leu Leu Asp Gly Thr Ser Gly Ile Ser Glu Ile Glu Thr Phe Asp Cys>
                                                                   370
GCT CAA TTT CCT ACG AGA ATT GCT GGA GAG ATC AAG TCT TTC TCC ACA
Ala Gln Phe Pro Thr Arg Ile Ala Gly Glu Ile Lys Ser Phe Ser Thr>
```

FIGURE 4

```
                                                                    420
                                                                     *
380          390          400          410
GAT GGT TGG GTG GCC CCG AAG CTC TCC AAG AGG ATG GAC AAG TTC ATG
Asp Gly Trp Val Ala Pro Lys Leu Ser Lys Arg Met Asp Lys Phe Met>

430          440          450          460
CTT TAC ATG CTG ACT GCC GGC AAG AAA GCA TTA ACA AAT GGT GGA ATC
Leu Tyr Met Leu Thr Ala Gly Lys Lys Ala Leu Thr Asn Gly Gly Ile>

470          480          490          500          510
             *
ACC GAA GAT GTG ATG AAA GAG CTA GAT AAA AGA AAA TGC GGA GTT CTC
Thr Glu Asp Val Met Lys Glu Leu Asp Lys Arg Lys Cys Gly Val Leu>

520          530          540          550          560
                                       *
ATT GGC TCA GCA ATG GGT GGA ATG AAG GTA TTC AAT CCC TTT TGT GTA CCT TTC
Ile Gly Ser Ala Met Gly Gly Met Lys Val Phe Asn Pro Phe Cys Val Pro Phe>

570          580          590          600          610
                                       *
GCC CTA AGG ATT TCA TAT AAG AAG ATG AAT GGA TCA GCT ATG CTT GCA ATG GAC TTG GGA TGG
Ala Leu Arg Ile Ser Tyr Lys Lys Met Asn Gly Ser Ala Met Leu Ala Met Asp Leu Gly Trp>

620          630          640          650          660
                                                                   *
GCT ACC ACA AAT ATG GGA TCA GCT ATG CTT GCA ATG GAC TTG GGA TGG
Ala Thr Thr Asn Met Gly Ser Ile Ser Thr Ala Cys Val Pro Asn Phe>

670          680          690          700
ATG GGC CCC AAC TAC TCG ATA TCT ACT GCT TGT GCA ACG AGT AAC TTT
Met Gly Pro Asn Tyr Ser Ile Ser Thr Ala Cys Ala Thr Ser Asn Phe>

FIGURE 4
```

```
710
TGT ATC CTG AAT GCT GCG AAC CAC ATA ATC AGA GGC GAA GCA GAT GTG
Cys Ile Leu Asn Ala Ala Asn His Ile Ile Arg Gly Glu Ala Asp Val>
        720                730                740                750

ATG CTT TGC GGG GGC TCA GAT GCG GTA ATC ATA CCT ATT GGT ATG GGA
Met Leu Cys Gly Gly Ser Asp Ala Val Ile Ile Pro Ile Gly Met Gly>
760                770                780                790                800

GGT TTT GTT GCA TGC CGA GCT TTG TCA CAG AGA AAT GCC GAC CCT ACT
Gly Phe Val Ala Cys Arg Ala Leu Ser Gln Arg Asn Ala Asp Pro Thr>
        810                820                830                840                850

AAA GCT TCA AGA CCA TGG GAC AGT AAT CGT GAT GGA TTT GTT ATG GGG
Lys Ala Ser Arg Pro Trp Asp Ser Asn Arg Asp Gly Phe Val Met Gly>
860                870                880                890                900

GAA GGA GCT GGA GTG CTA CTA CTA GAG GAG TTA GAG CAT GCA AAG AAA
Glu Gly Ala Gly Val Leu Leu Leu Glu Glu Leu Glu His Ala Lys Lys>
        910                920                930                940

AGA GGT GCG ACT ATT TAC GCA GAA TTT CTA GGT GGA AGT TTC ACT TGC
Arg Gly Ala Thr Ile Tyr Ala Glu Phe Leu Gly Gly Ser Phe Thr Cys>
950                960                970                980                990

GAT GCC TAC CAC ATG ACC GAG CCT CAC CCT GAT GGA GCT GGA GTG ATT
Asp Ala Tyr His Met Thr Glu Pro His Pro Asp Gly Ala Gly Val Ile>
        1000                1010                1020                1030                1040
```

CTC TGC ATA GAG AAG GCT TTG GCT CAG TCA GGA GTC TCT AGG GAA GAC
                                    Leu Cys Ile Glu Lys Ala Leu Ala Gln Ser Gly Val Ser Arg Glu Asp>

1100           1110           1120           1130           1140

GTA AAT TAC ATA AAT GCA CAT GCC ACA TCC ACT CCA GCT GGA GAT ATC
                                    Val Asn Tyr Ile Asn Ala His Ala Thr Ser Thr Pro Ala Gly Asp Ile>

1150           1160           1170           1180

AAA GAG TAC CAA GCT CTT ATC CAC TGT TTC GGC CAA AAC GAG TTA
                                    Lys Glu Tyr Gln Ala Leu Ile His Cys Phe Gly Gln Asn Glu Leu>

1190           1200           1210           1220           1230

AAA GTG AAT TCT ACC AAA TCA ATG ATT GGT CAC CTT CTC GGA GCA GCC
                                    Lys Val Asn Ser Thr Lys Ser Met Ile Gly His Leu Leu Gly Ala Ala>

1240           1250           1260           1270           1280

GGT GTG GAA GCA GTT TCA GTA GTT CAG GCA ATA AGG ACT GGG TGG
                                    Gly Gly Val Glu Ala Val Ser Val Val Gln Ala Ile Arg Thr Gly Trp>

1290           1300           1310           1320           1330

ATC CAT CCG AAT ATT AAT TTG GAA AAC CCA GAT GAA GGC GTG GAT ACC
                                    Ile His Pro Asn Ile Asn Leu Glu Asn Pro Asp Glu Gly Val Asp Thr>

1340           1350           1360           1370           1380

AAA TTG CTC GTG GGC CCT AAG AAG GAG AGA CTG AAC ATT AAG GTC GGT
                                    Lys Leu Leu Val Gly Pro Lys Lys Glu Arg Leu Asn Ile Lys Val Gly>

FIGURE 4
```

```
           1390           1400           1410           1420
TTG TCT AAT TCA TTC GGG TTT GGT GGG CAC AAC TCG TCC ATA CTC TTC
Leu Ser Asn Ser Phe Gly Phe Gly Gly His Asn Ser Ser Ile Leu Phe>

1430           1440           1450           1460           1470           1480
                 *
GCC CCT TAC AAC TAG GGCGTTT CATGTGTGGA ATTCTACTCA ATCTATCAAA
Ala Pro Tyr Asn ***>

1490      1500      1510      1520      1530      1540
          *
GCTGAAGTTT TGAGGACTCC AGCATGTTGG TAGCTCCTTA CGTCTCTAGA CATGCCCATG 1550      1560      1570      1580      1590      1600
          *
AGTTTTGTGT CGGGAGCTGT AGTCGGAACC ATGACGGATT GAGTACTCAT GGCGACACAG 1610      1620      1630      1640      1650      1660
          *
GATATACTCC TTGCTAGAAT TGTTAGAGCA CTATTCATTA TCCCATTTTT TTTCTGAAT 1670      1680      1690      1700      1710      1720
          *
CTCCCTCCTT ACGGTAGTTG TACTTTCGAG CGTTTCATCG AGTCAGTGAA GAAGAGAACA 1730      1740      1750      1760      1770      1780
          *
AAGCTAACTC GGGCACGTAG TAACCATTTG CCCTTTGTTT TGCTCTCTAT TTTATGCCG 1790      1800      1810      1820      1830      1840
          *
TTTTGTGGGT TAAAATTGT AAAACTAGAC GACTGGTTTG TTTTCTCTTG ATCATGGAG
```

FIGURE 4

```
      1850       1860       1870       1880       1890       1900
                    *
ATGTATGGCC ATATTTGCCT TTCATTGATG ATAAAAAAA AAAAAAAAA AAAAAAAAA
      1910       1920
                    *
AAAAAAAAA AAAAAAAAA A
```

FIGURE 4

```
CTGGTACGCC TGCAGGTACC GGTCCGGAAT TCCCGGGTCG ACCCACGGCT CCGTCTTCCC      60

ACTCCGATCG TTCTTCTTCC ACCGCATCTC TTCTCTTCTC TTGGCTTCTC CGCCATCCTC     120

CGCCGCC ATG CAT TCC CTC CAG TCA CTC CCC TCC CTT CGG GCC TCC CCG CTC   169
        Met His Ser Leu Gln Ser Leu Pro Ser Leu Arg Ala Ser Pro Leu
         1               5                  10

GAC CCC TTC CGC CCC AAA TCA TCC ACC GTC CGC CCC CTC CAC CGA GCA       217
Asp Pro Phe Arg Pro Lys Ser Ser Thr Val Arg Pro Leu His Arg Ala
 15                  20                  25                  30

TCA ATT CCC AAC GTC CGG GCC GCT CGG GCT TCC CCC ACC GTC TCC GCT CCC AAG   265
Ser Ile Pro Asn Val Arg Ala Ala Ser Pro Thr Val Ser Ala Pro Lys
         35                  40                  45

CGC GAG ACC GAC CCC AAG CGC GTC GTG ATC ACC GGA ATG GGC CTT           313
Arg Glu Thr Asp Pro Lys Arg Val Val Ile Thr Gly Met Gly Leu
     50                  55                  60

GTC TCC GTT TTC GGC TCC GAC GTC TAC TAC GAC CGC TTC GAC GCC AAG CTC CTG   361
Val Ser Val Phe Gly Ser Asp Val Tyr Tyr Asp Arg Phe Asp Ala Lys Leu Leu
 65                  70                  75

TCA GGC GAG AGC GGG ATC GGC CCA ATC GAC GGC TTC GAC GCC TCC AAG       409
Ser Gly Glu Ser Gly Ile Gly Pro Ile Asp Arg Phe Asp Ala Ser Lys
         80                  85                  90

TTC CCC ACC AGG TTC GGC GGC GGC CAG ATT CGT GGC GGC TTC AAC ATG GGA   457
Phe Pro Thr Arg Phe Gly Gly Gln Ile Arg Gly Phe Asn Met Gly
     95                  100                 105                 110

TAC ATT GAC GGC AAA AAC GAC AGG CGG CTT GAT GAT TGC CTT CGC TAC       505
Tyr Ile Asp Gly Lys Asn Asp Arg Arg Leu Asp Asp Cys Leu Arg Tyr
         115                 120                 125
```

FIGURE 5

| | | | | | | | | | | | | | | | | |
|---|---|---|---|---|---|---|---|---|---|---|---|---|---|---|---|---|
| TGC | ATT | GTC | GCC | GGG | AAG | AAG | TCT | CTT | GAG | GAC | GCC | GAT | CTC | GGT | GCC | 553 |
| Cys | Ile | Val | Ala | Gly | Lys | Lys | Ser | Leu | Glu | Asp | Ala | Asp | Leu | Gly | Ala | |
| | | | 130 | | | | | 135 | | | | | 140 | | | |
| GAC | CGC | CTC | TCC | AAG | ATC | GAC | AAG | AGA | GCC | GGA | GTG | CTG | GTT | GGG | | 601 |
| Asp | Arg | Leu | Ser | Lys | Ile | Asp | Lys | Arg | Ala | Gly | Val | Leu | Val | Gly | | |
| | | | 145 | | | | | 150 | | | | | 155 | | | |
| ACA | GGA | ATG | GGT | GGT | CTG | ACT | GTC | TTC | TCT | GAC | GGG | GTT | CAA | TCT | CTT | 649 |
| Thr | Gly | Met | Gly | Gly | Leu | Thr | Val | Phe | Ser | Asp | Gly | Val | Gln | Ser | Leu | |
| | | | 160 | | | | | 165 | | | | | 170 | | | |
| ATC | GAG | AAG | GGT | CAC | CGG | AAA | ATC | ACC | CCT | TTC | TTC | ATC | CCC | TAT | GCC | 697 |
| Ile | Glu | Lys | Gly | His | Arg | Lys | Ile | Thr | Pro | Phe | Phe | Ile | Pro | Tyr | Ala | |
| | | | 175 | | | | | 180 | | | | | 185 | | | 190 |
| ATT | ACA | AAC | ATG | GGG | TCT | GCC | CTG | CTC | GCT | ATT | GAA | CTC | GGT | CTG | ATG | 745 |
| Ile | Thr | Asn | Met | Gly | Ser | Ala | Leu | Leu | Ala | Ile | Glu | Leu | Gly | Leu | Met | |
| | | | | 195 | | | | | 200 | | | | | 205 | | |
| GGC | CCA | AAC | TAT | TCA | ATT | TCC | ACT | GCA | TGT | GCC | ACT | TCC | AAC | TAC | TGC | 793 |
| Gly | Pro | Asn | Tyr | Ser | Ile | Ser | Thr | Ala | Cys | Ala | Thr | Ser | Asn | Tyr | Cys | |
| | | | 210 | | | | | 215 | | | | | 220 | | | |
| TTC | CAT | GCT | GCT | AAT | CAT | ATC | CGC | CGT | GGT | GAG | GCT | GAT | CTT | ATG | | 841 |
| Phe | His | Ala | Ala | Asn | His | Ile | Arg | Arg | Gly | Glu | Ala | Asp | Leu | Met | | |
| | | | 225 | | | | | 230 | | | | | 235 | | | |
| ATT | GCT | GGA | GGC | ACT | GAG | GCC | GCA | ATC | ATT | CCA | ATT | GGG | TTG | GGA | GGC | 889 |
| Ile | Ala | Gly | Gly | Thr | Glu | Ala | Ala | Ile | Ile | Pro | Ile | Gly | Leu | Gly | Gly | |
| | | | 240 | | | | | 245 | | | | | 250 | | | |

FIGURE 5

```
TTT GTG GCT TGC AGG GCT CTG TCT CAA AGG AAC GAT GAC CCT CAG ACT       937
Phe Val Ala Cys Arg Ala Leu Ser Gln Arg Asn Asp Asp Pro Gln Thr
255                 260                 265                 270

GCC TCT AGG CCC TGG GAT AAA GAC CGT GAT GGT TTT GTG ATG GGT GAA       985
Ala Ser Arg Pro Trp Asp Lys Asp Arg Asp Gly Phe Val Met Gly Glu
            275                 280                 285

GGT GCT GGA GTG TTG GTG CTG GAG AGC TTG GAA CAT GCA ATG AAA CGA      1033
Gly Ala Gly Val Leu Val Leu Glu Ser Leu Glu His Ala Met Lys Arg
        290                 295                 300

GGA GCA CCT ATT ATT GCA GAG TAT TTG GGA GGT GCA ATC AAC TGT GAT      1081
Gly Ala Pro Ile Ile Ala Glu Tyr Leu Gly Gly Ala Ile Asn Cys Asp
305                 310                 315

GCT TAT CAC ATG ACT GAC CCA AGG GCT GAT GGT GTC CTC TCC TCT          1129
Ala Tyr His Met Thr Asp Pro Arg Ala Asp Gly Val Leu Ser Ser
    320                 325                 330

TGC ATT GAG AGT AGC CTT GAA GAT GCT GGC TCA CCT GAA GAG GTC          1176
Cys Ile Glu Ser Ser Leu Glu Asp Ala Gly Val Ser Pro Glu Glu Val
335                 340                 345                 350

AAT TAC ATA AAT GCT CTA GCT GGG GAT CTC GCC                          1224
Asn Tyr Ile Asn Ala Thr Ser Thr Leu Ala Gly Asp Leu Ala
            355                 360                 365

GAG ATA AAT GCC ATC AAG GTT TTC AAG AAC ACA AAG GAT ATC AAA          1272
Glu Ile Asn Ala Ile Lys Val Phe Lys Asn Thr Lys Asp Ile Lys
370                 375                 380
```

FIGURE 5

```
ATT AAT GCA ACT AAG TCA ATG ATC GGA CAC TGT CTT GGA GCC TCT GGA      1320
Ile Asn Ala Thr Lys Ser Met Ile Gly His Cys Leu Gly Ala Ser Gly
                385                         390                395

GGT CTT GAA GCT ATA GCG ACT ATT AAG GGA ATA AAC ACC GGC TGG CTT      1368
Gly Leu Glu Ala Ile Ala Thr Ile Lys Gly Ile Asn Thr Gly Trp Leu
        400                         405                     410

CAT CCC AGC ATT AAT CAA TTC AAT CCT GAG CCA TCC GTG GAG TTC GAC      1416
His Pro Ser Ile Asn Gln Phe Asn Pro Glu Pro Ser Val Glu Phe Asp
            415                         420                 425                 430

ACT GTT GCC AAC AAG CAG CAA CAC GAA GTT AAT GTT GCG ATC TCG          1464
Thr Val Ala Asn Lys Gln Gln His Glu Val Asn Val Ala Ile Ser
                435                         440                 445

AAT TCA TTT GGA TTC GGA GGC CAC AAC TCA GTC GTG GCT TTC TCG GCT      1512
Asn Ser Phe Gly Phe Gly Gly His Asn Ser Val Val Ala Phe Ser Ala
            450                         455                 460

TTC AAG CCA TGA TTACC CATTTCACAA GGCACTGTC ATTGAGAGTA CGGTTGTTCG     1569
Phe Lys Pro
        465

TCAAACCCAT TTAGGATACT GTTCTATGTA AAAAAAGTA AGGATTATCA CTTTCCCTTC     1629

TAATCCTGTC TCCAGTTTGA GAATGAAATT ATATTTATT TAAAAAAAA AAAAAGGGC       1689

GGCCGCTCTA GAGGATCCAA GCT                                            1712
```

FIGURE 5

Sequence Range: 1 to 1802

```
           10         20         30         40         50         60
                                                                   *
          GGTCGACCCA CGGGTCCGGG CTTCCGACC ACATTCATT TCTTGCCTCG TTATCTCCGC 70         80         90        100        110
          CGCTCCTCCG CCGTCGTTCG CCGCCCCCGC C ATG CAA TCC CTC CAC TCC CCT TCC
                                            Met Gln Ser Leu His Ser Pro Ser 120                      130        140        150        160
 *
CTC CGC CCC TCC CCT CTC GAG CCC TTC CGC CTC AAT TCC CCC TCC TCC
Leu Arg Pro Ser Pro Leu Glu Pro Phe Arg Leu Asn Ser Pro Ser Ser 170        180        190        200        210
                        *
GCC GCT CTC CGC CCC CTC CGT CGC GCC AGC CTC CCC GTC ATC CGT
Ala Ala Leu Arg Pro Leu Arg Arg Ala Ser Leu Pro Val Ile Arg 220        230        240        250
                                   *
GCT GCC ACC GCC TCC GCC CCC AAG CGC GAG TCC GAC CCC AAG AAG CGG
Ala Ala Thr Ala Ser Ala Pro Lys Arg Glu Ser Asp Pro Lys Lys Arg 260        270        280        290        300
                                                      *
GTC GTC ATC ACC GGC ATG GGC CTC GTC TCC GTC TTC GGC TCC GAC GTC
Val Val Ile Thr Gly Met Gly Leu Val Ser Val Phe Gly Ser Asp Val 310                  320        330        340        350
GAC GCC TAC TAC GAC AAG CTG TCC CTC CTC AGC GGC GAG AGC GGC ATC AGC CTA
Asp Ala Tyr Tyr Asp Lys Leu Ser Leu Leu Ser Gly Glu Ser Gly Ile Ser Leu
```

FIGURE 6

```
360
ATC GAC CGC TTC GAC GCT TCC AAA TTC CCC ACC AGG TTC GCC GGC CAG
Ile Asp Arg Phe Asp Ala Ser Lys Phe Pro Thr Arg Phe Ala Gly Gln
        370              380              390              400
410                                  440              450
ATC CGT GGC TTC AAC GCG ACG GGC TAC ATC GAC GGC AAG AAC GAC CGG
Ile Arg Gly Phe Asn Ala Thr Gly Tyr Ile Asp Gly Lys Asn Asp Arg
        420              430              440              450
460                                  480              490
CGG CTC GAC GAT TGC CTC CGC TAC TGC CTT GTC GCC GGC AAG AAG GCT
Arg Leu Asp Asp Cys Leu Arg Tyr Cys Leu Val Ala Gly Lys Lys Ala
500     510              520              530              540
CTC GAA GAC GCC GAT CTC GCC CAA TCC CTC AAG ATT GAT AAG
Leu Glu Asp Ala Asp Leu Ala Gly Gln Ser Leu Ser Lys Ile Asp Lys
        560              570              580              590
GAG AGG GCC GGA GTG CTA GTT GGA ACC GGT ATG GGT GGC CTA ACT GTC
Glu Arg Ala Gly Val Leu Val Gly Thr Gly Met Gly Gly Leu Thr Val
600     610              620              630              640
TTC TCT GAC GGG GTT CAG AAT CTC ATC GAG AAA GGT CAC CGG AAG ATC
Phe Ser Asp Gly Val Gln Asn Leu Ile Glu Lys Gly His Arg Lys Ile
        660              670              680              690
TCC CCG TTT TTC ATT CCA TAT GCC ATT ACA AAC ATG GGG TCT GCG CTG
Ser Pro Phe Phe Ile Pro Tyr Ala Ile Thr Asn Met Gly Ser Ala Leu
```

FIGURE 6

```
                                                                            ACT
         CTT GCC ATC GAT TTG GGT CTG ATG GGC CCA AAC TAT TCG ATT TCA ACT
         Leu Ala Ile Asp Leu Gly Leu Met Gly Pro Asn Tyr Ser Ile Ser Thr
        700       710       720       730
740                                                    780
         GCA TGT GCT ACT TCC AAC TAC TGC TTT TAT GCT GCC GCC AAT CAT ATC
         Ala Cys Ala Thr Ser Asn Tyr Cys Phe Tyr Ala Ala Ala Asn His Ile
        750       760       770                        830
790                                 810       820
         CGC CGA GGT GAG GCT GAC CTG ATG ATT GCT GGA GGA ACT GAG GCT GCG
         Arg Arg Gly Glu Ala Asp Leu Met Ile Ala Gly Gly Thr Glu Ala Ala
        800                       860       870       880
840
         GTC ATT CCA ATT GGT TTA GGA GGA TTC GTT GCC TGC AGG GCT TTA TCT
         Val Ile Pro Ile Gly Leu Gly Gly Phe Val Ala Cys Arg Ala Leu Ser
890                       910       920                 930
        900
         CAA AGG AAT GAT GAT CCT CAG ACT GCC TCA AGG CCG TGG GAT AAG GAC
         Gln Arg Asn Asp Asp Pro Gln Thr Ala Ser Arg Pro Trp Asp Lys Asp
940                       960                 970
        950
         CGT GAT GGC TTT GTG ATG GGT GAA GGG GCT GGA GTA TTG GTT ATG GAG
         Arg Asp Gly Phe Val Met Gly Glu Gly Ala Gly Val Leu Val Met Glu
                                              1010       1020
980      990       1000
         AGC TTG GAG CAT GCA ATG AAA CGG GGA GCG CCG ATT ATT GCA GAA TAT
         Ser Leu Glu His Ala Met Lys Arg Gly Ala Pro Ile Ile Ala Glu Tyr

FIGURE 6
```

```
1030              1040              1050              1060              1070
TTG GGA GGT GCA GTC AAC TGT GAT GCT TAT CAT ATG ACT GAT CCA AGG
Leu Gly Gly Ala Val Asn Cys Asp Ala Tyr His Met Thr Asp Pro Arg
     1080              1090              1100              1110              1120
GCT GAT GGG CTT GGT GTC TCC TCG TGC ATT GAG AGC AGT CTC GAA GAT
Ala Asp Gly Leu Gly Val Ser Ser Cys Ile Glu Ser Ser Leu Glu Asp
     1130              1140              1150              1160              1170
GCC GGG GTC TCA CCT GAA GAG GTC AAT TAC ATA AAT GCT CAT GCG ACT
Ala Gly Val Ser Pro Glu Glu Val Asn Tyr Ile Asn Ala His Ala Thr
     1180              1190              1200              1210
TCT ACT CTT GCT GGG GAT CTT GCC GAG ATA AAT GCC ATT AAG AAA GTT
Ser Thr Leu Ala Gly Asp Leu Ala Glu Ile Asn Ala Ile Lys Lys Val
     1220              1230              1240              1250              1260
TTC AAG AAC ACC AAG GAA ATC AAA ATC AAT GCA ACT AAG TCA ATG ATC
Phe Lys Asn Thr Lys Glu Ile Ile Lys Ile Asn Ala Thr Lys Ser Met Ile
     1270              1280              1290              1300              1310
GGA CAC TGT CTT CTT GGA GCA TCA GGA GGT CTT GAA GCC ATC GCA ACC ATT
Gly His Cys Leu Leu Gly Ala Ser Gly Gly Leu Glu Ala Ile Ala Thr Ile
     1320              1330              1340              1350              1360
AAG GGA ATA ACC ACC GGC TGG CTT CAT CCC AGC ATT AAT CAA TTT AAT
Lys Gly Ile Thr Thr Gly Trp Leu His Pro Ser Ile Asn Gln Phe Asn
```

FIGURE 6

```
                   1370      1380      1390      1400      1410
CCC GAG CCA TCG GTG GTG GAC TTC AAC ACT GTT GCC AAC AAA AAG CAG CAA
Pro Glu Pro Ser Val Val Asp Phe Asn Thr Val Ala Asn Lys Lys Gln Gln
         1420      1430      1440      1450
                                     *
CAT GAA GTG AAC GTC GCT ATC TCG AAT TCT TTT GGA TTT GGA GGG CAC
His Glu Val Asn Val Ala Ile Ser Asn Ser Phe Gly Phe Gly Gly His
1460      1470      1480      1490      1500      1510
                                        *
AAC TCG GTT GTG GCA TTC TCA GCT TTC AAG CCA TGA ATTCT ACTTGGTCA
Asn Ser Val Val Ala Phe Ser Ala Phe Lys Pro ***
      1520      1530      1540      1550      1560      1570
                                             *
AAATGCACAC CAGTTGCTGA GATAGGGCTT CAACTTGCAG AGCAATTTTT TAAATGCCTT
      1580      1590      1600      1610      1620      1630
                                             *
GTCGGAAGAG CGTAATACCG GAATAGGTCG GTCCTTTGAT AGTTCCTCGA AGCCATTAG
      1640      1650      1660      1670      1680      1690
                                             *
GATGATGTTT TACTGTAATA ATCGAAGATG AATCCCATTT TAAATCTAGT CTCTGATTTA
      1700      1710      1720      1730      1740      1750
                                             *
TGTATTAGAA AGACCAATGA AAGATTTTGT GTCATGTTTG TGTTGTCAAT GTTATTAAG
      1760      1770      1780      1790      1800
                                             *
ATAAAGCAAA AAAAAAAAA AAGGGCGGCC GCTCTAGAGG ATCCAGCTTA CT
```

FIGURE 6

Sequence Range: 1 to 2369

```
                10         20         30         40         50         60
                                                                          .
            GTACGCCTGC AGGTACCGGT CCGGAATTCC CGGGTCGACC CACGGGTCCG CATAAAGAG
                70         80         90        100        110        120
                                                                          .
            AGAGAGAGGG ATCCATCGAA TGCGGCCACC CTCCTTTCAT CTTCGATTCA TTACCATACC
               130        140        150        160        170        180
                                                                          .
            ATTCCGCTGA TCCATTTTCC GCCTTTTCCG GGTCTTTCAT CCCAAAGGGT ATCCTTTTCT
               190        200        210        220        230
            ATCCTATCTT CTCAAAGGGT CAGTCAGTTC CCTCCA ATG CCT GCC GCC TCT TCC
                                                  Met Pro Ala Ala Ser Ser>
                240        250        260        270        280
                  *
            CTG CTC GCT TCC CCT CTC TGT ACG TGG CTC CTT GCC GCC TGC ATG TCT
            Leu Leu Ala Ser Pro Leu Cys Thr Trp Leu Leu Ala Ala Cys Met Ser>
                290        300        310        320        330
                                         *
            ACC TTC CAC CCC TCC GAC CCT CCT CCG CCT CTT CCC ATC TCC TCT CCT
            Thr Ser Phe His Pro Ser Asp Pro Leu Pro Pro Leu Pro Ser Ile Ser Ser Pro>
                340        350        360        370
                       ᵕ                    .
            CGC CGA CGC CTC TCC CGC CGC CGG ATT CTC TCC CAA TGC GCC CCA CTA
            Arg Arg Arg Leu Ser Arg Arg Arg Ile Leu Ser Gln Cys Ala Pro Leu>
```

FIGURE 7

```
380           390           400           410           420
CCT TCT GCT TCC TCC GCC CTC CGC GGA TCC AGT TTC CAT ACC CTC GTC
Pro Ser Ala Ser Ser Ala Leu Arg Gly Ser Ser Phe His Thr Leu Val>

430           440           450           460           470
ACC TCT TAC CTC GCC TGC TTC GAG CCC TGC CAT GAC TAC TAT ACA TCC
Thr Ser Tyr Leu Ala Cys Phe Glu Pro Cys His Asp Tyr Tyr Thr Ser>

480           490           500           510           520
GCA TCC TTG TTC GGA TCC AGA CCC ATT CGC ACC CGC AGG CAC CGG
Ala Ser Leu Phe Gly Ser Arg Pro Ile Arg Thr Arg Arg His Arg>

530           540           550           560           570
AGG CTC AAT CGA GCT TCC CCT TCC AGG GAG GCA ATG GCC GTG GCT CTG
Arg Leu Asn Arg Ala Ser Pro Ser Arg Glu Ala Met Ala Val Ala Leu>

580           590           600           610
CAA CCT GAA CAG GAA GTT ACC ACA AAG AAG CCA AGT ATC AAA CAG
Gln Pro Glu Gln Glu Val Thr Thr Lys Lys Pro Ser Ile Lys Gln>

620           630           640           650           660
CGG CGA GTA GTT GTG ACT GGA ATG GGT GTG ACT CCT CTA GGC CAT
Arg Arg Val Val Val Thr Gly Met Gly Val Thr Pro Leu Gly His>

670           680           690           700           710
GAC CCT GAT GTT TTC TAC AAT CTG CTT GAT GGA ACG AGT GGC ATA
Asp Pro Asp Val Phe Tyr Asn Leu Leu Asp Gly Thr Ser Gly Ile>
```

FIGURE 7

```
720                730                740                750                760
 *
AGC GAG ATA GAG ACC TTT GAT TGT GCT CAA TTT CCT ACG AGA ATT GCT
Ser Glu Ile Glu Thr Phe Asp Cys Ala Gln Phe Pro Thr Arg Ile Ala>
            770                780                790                800                810
                         *
GGA GAG ATC AAG TCT TTC TCC ACA GAT GGT TGG GTG GCC CCG AAG CTC
Gly Glu Ile Lys Ser Phe Ser Thr Asp Gly Trp Val Ala Pro Lys Leu>
  820                830                840                850
TCT AAG AGG ATG GAC AAG TTC ATG CTA TAC ATG CTG ACC GCT GGC AAG
Ser Lys Arg Met Asp Lys Phe Met Leu Tyr Met Leu Thr Ala Gly Lys>
860                870                880                890                900
                                                                  *
AAA GCA TTA ACA GAT GGT GGA ATC ACC GAA GAT GTG AAA GAG CTA
Lys Ala Leu Thr Asp Gly Gly Ile Thr Glu Asp Val Met Lys Glu Leu>
   910                920                930                940                950
GAT AAA AGA AAA TGC GGA GTT CTC ATT GGC TCA GCA ATG GGT GGA ATG
Asp Lys Arg Lys Cys Gly Val Leu Ile Gly Ser Ala Met Gly Gly Met>
  960                970                980                990                1000
 *
AAG GTA TTC AAT GAT GCC ATT GAA GCC CTA AGG ATT TCA TAT AAG AAG
Lys Val Phe Asn Asp Ala Ile Glu Ala Leu Arg Ile Ser Tyr Lys Lys>
            1010                1020                1030                1040                1050
                              *
ATG AAT CCC TTT TGT GTA CCT TTC GCT ACC ACA AAT ATG GGA TCA GCT
Met Asn Pro Phe Cys Val Pro Phe Ala Thr Thr Asn Met Gly Ser Ala>

FIGURE 7
```

```
                    1060           1070           1080           1090
ATG CTT GCA ATG GAC TTG GGA TGG ATG GGG CCC AAC TAC TCG ATA TCT
Met Leu Ala Met Asp Leu Gly Trp Met Gly Pro Asn Tyr Ser Ile Ser>

1100           1110           1120           1130           1140
ACT GCT TGT GCA ACG AGT AAC TTT TGT ATA ATG AAT GCT GCG AAC CAT
Thr Ala Cys Ala Thr Ser Asn Phe Cys Ile Met Asn Ala Ala Asn His>

1150           1160           1170           1180           1190
ATA ATC AGA GGC GAA GCA GAT GTG ATG CTT TGC GGG GGC TCA GAT GCG
Ile Ile Arg Gly Glu Ala Asp Val Met Leu Cys Gly Gly Ser Asp Ala>

1200           1210           1220           1230           1240
GTA ATC ATA CCT ATT GGT ATG GGT TTT GTT GCA TGC CGA GCT TTG
Val Ile Ile Pro Ile Gly Met Gly Gly Phe Val Ala Cys Arg Ala Leu>

1250           1260           1270           1280           1290
TCC CAG AGA AAT TCC GAC CCT ACT AAA GCT TCA AGA CCA TGG GAC AGT
Ser Gln Arg Asn Ser Asp Pro Thr Lys Ala Ser Arg Pro Trp Asp Ser>

1300           1310           1320           1330
AAT CGT GAT GGA TTT GTT ATG GGG GAA GCT GGA GCT GGA GTG CTA CTA
Asn Arg Asp Gly Phe Val Met Gly Glu Ala Gly Ala Gly Val Leu Leu>

1340           1350           1360           1370           1380
GAG GAG TTG GAG CAT GCA AAG AAA AGA GGT GCG ACT ATT TAC GCA GAA
Glu Glu Leu Glu His Ala Lys Lys Arg Gly Ala Thr Ile Tyr Ala Glu>
```

FIGURE 7

```
     1390            1400            1410            1420            1430
TTT CTA GGT GGG AGT TTC ACT TGC GAT GCC TAC CAC ATG ACC GAG CCT
Phe Leu Gly Gly Ser Phe Thr Cys Asp Ala Tyr His Met Thr Glu Pro>

1440            1450            1460            1470            1480
CAC CCT GAT GGA GCT GGA GTG ATT CTC ATA GAG AAG GCT TTG GCT
His Pro Asp Gly Ala Gly Val Ile Leu Cys Ile Glu Lys Ala Leu Ala>

1490            1500            1510            1520            1530
CAG TCA GGA GTC TCT AGG GAA GAC GTA AAT TAC ATA AAT GCC CAT GCC
Gln Ser Gly Val Ser Arg Glu Asp Val Asn Tyr Ile Asn Ala His Ala>

1540            1550            1560            1570
ACA TCC ACT CCG GCT GGA GAT ATC AAA GAG TAC CAA GCT CTT ATC CAC
Thr Ser Thr Pro Ala Gly Asp Ile Lys Glu Tyr Gln Ala Leu Ile His>

1580            1590            1600            1610            1620
TGT TTC GGC CAA AAC AGA GAG TTA AAA GTT AAT TCA ACC AAA TCA ATG
Cys Phe Gly Gln Asn Arg Glu Leu Lys Val Asn Ser Thr Lys Ser Met>

1630            1640            1650            1660            1670
ATT GGT CAC CTT CTC GGA GCA GCC GGT GGT GAA GCA GTT TCA GTA
Ile Gly His Leu Leu Gly Ala Ala Gly Gly Val Glu Ala Val Ser Val>

1680            1690            1700            1710            1720
GTT CAG GCA ATA AGG ACT GGG ATC CAT CCG AAT ATT TTG GAA
Val Gln Ala Ile Arg Thr Gly Trp Ile His Pro Asn Ile Asn Leu Glu>

FIGURE 7
```

```
                                1730         1740         1750         1760         1770
                                              *
AAC CCA GAT GAA GGC GTG GAT ACA AAA TTG CTC GTG GGT CCT AAG AAG
Asn Pro Asp Glu Gly Val Asp Thr Lys Leu Leu Val Gly Pro Lys Lys>
              1780         1790         1800         1810
                                          *
GAG AGA CTG AAC GTT AAG GTC GGT TTG TCT AAT TCA TTT GGG TTT GGT
Glu Arg Leu Asn Val Lys Val Gly Leu Ser Asn Ser Phe Gly Phe Gly>
1820         1830         1840         1850         1860         1870
                                                      *
GGG CAC AAC TCG TCC ATA CTC TTC GCC CCT TAC ATC TAG GAC GTTCCGTGT
Gly His Asn Ser Ser Ile Leu Phe Ala Pro Tyr Ile ***>
   1880         1890         1900         1910         1920         1930
                                                        *
GTGGAATTCT ACTCAACATA TCAAAGCTGA AGTTTTGAGG ACTCCAGCAT GTTGGTAGCT
   1940         1950         1960         1970         1980         1990
                                                        *
CCTTACGTCT CTAGACATGC CCATGAGTTT TGTGTCCGGA GCTTTAGTCG GAACCATGAC
   2000         2010         2020         2030         2040         2050
                                                        *
GGATTGAGTA CTCATGGCGA CACTTGATAT ACTCCTTGCT AGAATTGTTG GTAGAGCAAT
   2060         2070         2080         2090         2100         2110
                                                        *
ATTCATTATC TCATATTTTT TTTTTCTCTG AAATCTCCCT CCTTGCAATA GTTGTACTTT
   2120         2130         2140         2150         2160         2170
                                                        *
CGAGCTTTTC ATCGAGTCAG TGAAGAAGAG ACAAAGCTG TTAACTCGGG CACGTAGTAA
```

FIGURE 7

```
      2180       2190       2200       2210       2220       2230
CCATTGCCC TTTGTTTGC TCTCTATTC ATCACGTTT TGTGGTTTA AAATTGTAA 2240       2250       2260       2270       2280       2290
AACTAGAAGA CTGGTTTAGA TGGTTTGTT TTCTCATTGA TAATTGGGGR ATGTATGTTT 2300       2310       2320       2330       2340       2350
TGGAAATAAA AAAAAAAAA AAAAAAAAA AAAAAAAAA AAAAAAAAA AAAAAAAAA

2360
AGGGCGGCCG CTCTAGAGG
```

FIGURE 7

Sequence Range: 1 to 2374

```
         10         20         30         40         50         60
                                                                    *
--A-CNTGGTC CGGAATTCCC GGGTCGACCC ACGGGTCCGC GACGCCAACC CACACCAAAC
         70         80         90        100        110        120
                                                                    *
TTCCCTCAGCT TCTCTTCTCA AGACGGACGC CATTGGCAGC AGACAGACAG ACAGACAGAC
        130        140        150        160        170        180
                                                                    *
CCATAAAAGA GAGAGAGAGG GATCCATCGA ATGCGGGCCAC CCTCCTTTCA TCTTCGATTC
        190        200        210        220        230        240
                                                                    *
ATTACCATAC CATTCCGCTG ATCCATTTTC CGCCTTTTCC GGGTCTTTCA TCCCAAGGG
        250        260        270        280        290        300
                                                                    *
TATCCTTTTC TATCCTATCT TCTCAAAGGG TCAGTCAGTT CCCTCCAATG CCTGCCGCCT
        310        320        330        340        350        360
                                                                    *
CTTCCCCTGCT CGCTTCCCCT CTCTGTACGT GGCTCCTTGC CGCCTGCATG TCTACCTCCT
        370        380        390        400        410        420
                                                                    *
TCCACCCCTC CGACCCTCTT CCGGCTTCCA TCTCCTCTCC TCGCCGACGC CTCTCCCGCC
        430        440        450        460        470        480
                                                                    *
GCCGGATTCT CTCCCAATGC GCCCACTAC CTTCTGCTTC CTCCGCCCTC CGGGGATCCA
```

FIGURE 8

```
         490        500        510        520        530        540
                                                                   *
         GTTTCCATAC CCTCGTCACC TCTTACCTCG CCTGCTTCGA GCCCTGCCAT GACTACTATA
         550        560        570        580        590        600
                                                                   *
         CATCCGCATC CTTGTTCGGA TCCAGACCCA TTCGCACCAC CCGGCAGGCAC CGGAGGCTCA
         610        620        630        640        650        660
                                                                   *
         ATCGAGCTTC CCCTTCCAGG GGAGGCAATG GCCGTGGCTC TGCAACCTGA ACAGGAAGTT
         670        680        690        700        710        720
                                                                   *
         ACCACAAAGA AGAAGCCAAG TATCAAACAG CGGGGAGTAG TTGTGACTGG AATGGGTGTG
         730        740        750        760        770        780
                                                                   *
         GTGACTCCTC TAGGCCATGA ACCTGATGTT TTTCTACAAT AATCTGCTTG ATGGAAGAG
         790        800        810        820        830        840
                                                                   *
         TGGCATAAGC GAGATAGAGA CCTTTGATTG TGCTCAATTT CCTACGAGAA TTGCTGGAGA
         850        860        870        880        890        900
                                                                   *
         GATCAAGTCT TTCTCCACAG ATGGTTGGGT GGCCCCGAAG CTCTCTAAGA GGATGGACAA
         910        920        930        940        950        960
                                                                   *
         GTTCATGCTA TACATGCTGA CTGCTGGCAA GAAAGCAATA ACAGATGGTG GAATCACCGA
         970        980        990        1000       1010       1020
                                                                   *
         AGATGTGATG AAGAGCTAG ATAAAAGAAA ATGCGGGAGTT CTCATTGGCT CAGCAATGGG
```

FIGURE 8

```
1030      1040       1050       1060       1070       1080
                                                            *
TGGAATGAAG GTATTCAATG ATGCCATTGA AGCCCTAAGG ATTTCATATA AGAAGATGAA 1090      1100       1110       1120       1130       1140
                                                            *
TCCCTTTTGT GTACCTTTCG CTACCACAAA TATGGGATCA GCTATGCTTG CAATGGACTT 1150      1160       1170       1180       1190       1200
                                                            *
GGGATGGATG GGGCCCAACT ACTCGATATC TACTGCTTGT GCAACGAGTA ACTTTTGTAT 1210      1220       1230       1240       1250       1260
                                                            *
AATGAATGCT GCGAACCATA TAATCAGAGG CGAAGCAGAT GTGATGCTTT GCGGGGCTC 1270      1280       1290       1300       1310       1320
                                                            *
AGATGCGGTA ATCATACCTA TTGGTATGGG AGTTTTGTT GCATGCCGAG CTTTGTCCCA 1330      1340       1350       1360       1370       1380
                                                            *
GAGAAATTCC GACCCTACTA AAGCTTCAAG ACCATGGGAC AGTAATCGTG ATGGATTGT 1390      1400       1410       1420       1430       1440
                                                            *
TATGGGGGAA GGAGCTGGAG TGCTACTACT AGAGGAGTTG GAGCATGCAA AGAAAGAGG 1450      1460       1470       1480       1490       1500
                                                            *
TGCGACTATT TACGCAGAAT TTCTAGGTGG GAGTTTCACT TGGATGCCT ACCACATGAC
```

FIGURE 8

```
          1510       1520       1530       1540       1550       1560
CGAGCCTCAC CCTGATGGAG CTGGAGTGAT TCTCTGCATA GAGAAGGCTT TGGCTCAGTC 1570       1580       1590       1600       1610       1620
AGGAGTCTCT AGGGAAGAGG TAAATAACAT AAATGCCCAT GCCACATCCA CTCCGGCTGG 1630       1640       1650       1660       1670       1680
AGATATCAAA GAGTACCAAG CTCTTATCCA CTGTTTCGGC CAAAACAGAG AGTTAAAGT 1690       1700       1710       1720       1730       1740
TAATTCAACC AAATCAATGA TTGGTCACCT TCTCGGAGCA GCCGGTGGTG TGGAAGCAGT 1750       1760       1770       1780       1790       1800
TTCAGTAGTT CAGGCAATAA GGACTGGGTG GATCCATCCG AATATTAATT TGGAAACCC 1810       1820       1830       1840       1850       1860
AGATGAAGGC GTGGATACAA AATGCTCGT GGTCCTAAG AAGGAGAGAC TGAACGTTAA 1870       1880       1890       1900       1910       1920
GGTCGGTTTG TCTAATTCAT TTGGGTTGG TGGGCACAAC TGTCCATAC TCTTCGCCCC 1930       1940       1950       1960       1970       1980
TTACATCTAG GACGTTTCGT GTGTGGAATT CTACTCAACA TATCAAAGCT GAAGTTTGA 1990       2000       2010       2020       2030       2040
GGACTCCAGC AATGTGGTAG CTCCTTACGT CTCTAGACAT GCCCATGAGT TTTGTGTCCG
```

FIGURE 8

```
       2050        2060        2070        2080        2090        2100
GAGCTTTAGT CGGAACCATG ACGGATTGAG TACTCATGGC GACACTTGAT ATACTCCTTG
       2110        2120        2130        2140        2150        2160
CTAGAATTGT TGGTAGAGCA ATATTCATTA TCTCATATTT TTTTTTCTC TGAAATCTCC
       2170        2180        2190        2200        2210        2220
CTCCCTTGCAA TAGTTGTACT TTCGAGCTTT TCATCGAGTC AGTGAAGAAG AGAACAAGC
       2230        2240        2250        2260        2270        2280
CTCCCTTGCAA TAGTTGTACT TTCGAGCTTT TCATCGAGTC AGTGAAGAAG AGAACAAGC
       2290        2300        2310        2320        2330        2340
TGTTAACTCG GGCACGTAGT AACCATTGC CCTTGTTTT GCTCTCTATT TCATCACCGT
       2290        2300        2310        2320        2330        2340
TGTTAACTCG GGCACGTAGT AACCATTGC CCTTGTTTT GCTCTCTATT TCATCACCGT

TTTGTGGTTT TAAAATTTGT AAAACTAGAA GACTGGTTTA GATTGGTTTG TTTCTCAAA
       2350        2360        2370
AAAAAAAAAA AAGGGCGGGCC GCTCTAGAGG ATCC
```

FIGURE 8

Sequence Range: 1 to 1580

```
          10         20         30         40         50
CCTGAATCGG ATTCAAGAGA GAGTTTCGTT GCTGGG ATG GCG AAT GCA TCT GGG
                                        Met Ala Asn Ala Ser Gly>

60              70              80              90             100
TTT CTG GGT TCT TCA GTT CCT GCC CTG AGA AGG GCA ACT CAG CAT TCG
Phe Leu Gly Ser Ser Val Pro Ala Leu Arg Arg Ala Thr Gln His Ser>

110             120             130             140             150
ATT TCA TCG TCT CGT GGA TCT TCC TCG GAG TTT GTC TCC AAA AGG GTG
Ile Ser Ser Ser Arg Gly Ser Ser Ser Glu Phe Val Ser Lys Arg Val>

160             170             180             190
TTT TGC TGT AGT GCC GTT CAG GAT TCT GAC AGG CAG TCT TTG GGT GAT
Phe Cys Cys Ser Ala Val Gln Asp Ser Asp Arg Gln Ser Leu Gly Asp>

200     210             220             230             240
TCT CGC TCG CCG AGG CTT GTG AGT AGA GGA TGC AAA TTA ATT GGA TCT
Ser Arg Ser Pro Arg Leu Val Ser Arg Gly Cys Lys Leu Ile Gly Ser>

250             260             270             280             290
GGT TCT GCT ATA CCA GCT CTT CAA GTC TCA AAT GAT GAT CTT GCT AAA
Gly Ser Ala Ile Pro Ala Leu Gln Val Ser Asn Asp Asp Leu Ala Lys>

300             310             320             330             340
ATT GTC GAC ACC AAT GAT GAA TGG ATT ACT GTC CGA ACG GGG ATC CGC
Ile Val Asp Thr Asn Asp Glu Trp Ile Thr Val Arg Thr Gly Ile Arg>
```

FIGURE 9

```
                350           360           370           380           390
AAC CGA AGG GTT CTC TCA GGT AAA GAT AGT CTT ACA AAT TTA GCA TCA
Asn Arg Arg Val Leu Ser Gly Lys Asp Ser Leu Thr Asn Leu Ala Ser>

400           410           420           430
GAG GCA GCA AGG AAA GCT CTA GAG ATG GCA CAG GTA GAC GCA AAT GAT
Glu Ala Ala Arg Lys Ala Leu Glu Met Ala Gln Val Asp Ala Asn Asp>

440           450           460           470           480
GTG GAT ATG GTT TTG ATG TGT ACT TCT ACC CCT GAG GAC CTT TTC GGC
Val Asp Met Val Leu Met Cys Thr Ser Thr Pro Glu Asp Leu Phe Gly>

490           500           510           520           530
AGT GCT CCT CAG ATA TCG AAA GCA CTT GGC TGC AAA AAG AAT CCT TTG
Ser Ala Pro Gln Ile Ser Lys Ala Leu Gly Cys Lys Lys Asn Pro Leu>

540           550           560           570           580
TCT TAC GAC ATT ACC GCT GCA TGC AGT GGA TTT GTG TTG GGT TTA GTC
Ser Tyr Asp Ile Thr Ala Ala Cys Ser Gly Phe Val Leu Gly Leu Val>

590           600           610           620           630
TCA GCT GCT TGC CAC ATT AGA GGT GGG GGT TTT AAC AAT ATT CTA GTG
Ser Ala Ala Cys His Ile Arg Gly Gly Gly Phe Asn Asn Ile Leu Val>

640           650           660           670
ATT GGT GCT GAT TCT CTT TCT CGG TAT GTT GAC TGG ACC GAT CGG GGA
Ile Gly Ala Asp Ser Leu Ser Arg Tyr Val Asp Trp Thr Asp Arg Gly>
```

FIGURE 9

```
680
ACA TGT ATT CTC TTT GGA GAT GCT GCT GGA GCT GTA GTG CAG TCA
Thr Cys Ile Leu Phe Gly Asp Ala Ala Gly Ala Val Val Gln Ser>
         690            700            710            720

TGT GAT GCT GAG GAA GAT GGG GAC CTC TTT GCT TTT GAT TTG CAT AGC GAT
Cys Asp Ala Glu Glu Asp Gly Asp Leu Phe Ala Phe Asp Leu His Ser Asp>
         730            740            750            760            770

GGA GAT GGG CAA AGG CAT CTA AAA GCT GCA ATC AAA GAA GAT GAA GTT
Gly Asp Gly Gln Arg His Leu Lys Ala Ala Ile Lys Glu Asp Glu Val>
         780            790            800            810            820            870

GAT AAA GCC CTG GGA CAT AAT GGG TCC ATC AGA GAT TTT CCA CCA AGG
Asp Lys Ala Leu Gly His Asn Gly Ser Ile Arg Asp Phe Pro Pro Arg>
         830            840            850            860            870

CGT TCT TCA TAC TCT TGC ATC CAA ATG AAC GGT AAA GAG GTA TTC CGC
Arg Ser Ser Tyr Ser Cys Ile Gln Met Asn Gly Lys Glu Val Phe Arg>
         880            890            900            910

TTT GCT TGC CGC TCT GTG CCT CAG TCA ATC GAA TCA GCA CTT GGA AAG
Phe Ala Cys Arg Ser Val Pro Gln Ser Ile Glu Ser Ala Leu Gly Lys>
         920            930            940            950            960

GCC GGT CTT AAT GGA TCC AAC ATC GAC TGG TTG CTG CTT CAT CAG GCA
Ala Gly Leu Asn Gly Ser Asn Ile Asp Trp Leu Leu Leu His Gln Ala>
         970            980            990            1000            1010
```

FIGURE 9

```
                1020          1030          1040          1050          1060
                 *
AAT CAG AGG ATC ATT GAT GCA GTA GCA ACA CGT CTA GAG GTT CCT CAA
Asn Gln Arg Ile Ile Asp Ala Val Ala Thr Arg Leu Glu Val Pro Gln>

1070          1080          1090          1100          1110
                               *
GAA CGA ATT ATC TCA AAC TTG GCA AAT TAC GGG AAC ACT AGT GCG GCA
Glu Arg Ile Ile Ser Asn Leu Ala Asn Tyr Gly Asn Thr Ser Ala Ala>

1120          1130          1140          1150
                                             *
TCC ATT CCC TTG GCA CTA GAC GAA GCT GTG AGG AGT GGA AAT GTG AAG
Ser Ile Pro Leu Ala Leu Asp Glu Ala Val Arg Ser Gly Asn Val Lys>

1160          1170          1180          1190          1200
                                                           *
CCG GGT CAC GTG ATT GCA ACC GCA GGA TTT GGC GCC GGA CTC ACA TGG
Pro Gly His Val Ile Ala Thr Ala Gly Phe Gly Ala Gly Leu Thr Trp>

1210          1220          1230          1240          1250
                                                                          *
GGT TCT GCT ATT ATC AGG TGG GGA TAA GACTGAA GCCGAGCCAG CACTGCAGCT
Gly Ser Ala Ile Ile Arg Trp Gly ***>

1260          1270          1280          1290          1300          1310          1320
          *                                                                                    *
TCCTCTCAAA CCGATGTTTC AGAAATTTT GCTTCCATGA CCAAAAAAG AAGAAGTCAG 1330          1340          1350          1360          1370          1380
                                                                                *
TCTTTTATGG AGCAAGCAAC AGACACGAT CTTCATCACA TTGCCCTTTT TCGTTCCCCT

FIGURE 9
```

```
         1390       1400       1410       1420       1430       1440
TTTCCATTAG TTTGATGATT TGCTGACAA TACAATACCC ATAGTTTCTT TTGTCCCAA 1450       1460       1470       1480       1490       1500
TAAGTTATT GTTTCTGTT TAATTGTTCA GCTTTACTT CATTTGTCT CGGGACATG 1510       1520       1530       1540       1550       1560
GAGATGACAG CATAAACATC ATGTTTATAT TTTGCTAAAA AAAAAAAA AAAAAAAAA 1570       1580
AAAAAAAAA AAAAAAAAA
```

PLANT FATTY ACID SYNTHASES AND USE IN IMPROVED METHODS FOR PRODUCTION OF MEDIUM-CHAIN FATTY ACIDS

CROSS-REFERENCE TO RELATED APPLICATIONS

This application is a divisional of U.S. patent application Ser. No. 09/057,996, filed Apr. 9, 1998 now U.S. Pat. No. 6,660,849, which claims the benefit under 35 U.S.C. § 119(e) of U.S. patent application Ser. No. 60/041,815, filed Apr. 11, 1997. U.S. patent application Ser. No. 09/057,996 is herein incorporated by reference in its entirety.

INCORPORATION OF SEQUENCING LISTING

A paper copy of the Sequence Listing and a computer readable form of the sequence listing on diskette, containing the file named 16518131seq(ASFILED).txt which is 54,544 bytes in size (measured in MS-DOS), and which was created on Aug. 7, 2003, is herein incorporated by reference in its entirety.

FIELD OF INVENTION

The present invention is directed to genes encoding plant fatty acid synthase enzymes relevant to fatty acid synthesis in plants, and to methods of using such genes in combination with genes encoding plant medium-chain preferring thioesterase proteins. Such uses provide a method to increase the levels of medium-chain fatty acids that may be produced in seed oils of transgenic plants.

BACKGROUND

Higher plants synthesize fatty acids via a common metabolic pathway. In developing seeds, where fatty acids attached to triglycerides are stored as a source of energy for further germination, the fatty acid synthesis pathway is located in the plastids. The first step is the formation of acetyl-ACP (acyl carrier protein) from acetyl-CoA and ACP catalyzed by a short chain preferring condensing enzyme, β-ketoacyl-ACP synthase (K-S) III. Elongation of acetyl-ACP to 16- and 18-carbon fatty acids involves the cyclical action of the following sequence of reactions: condensation with a two-carbon unit from malonyl-ACP to form a longer β-ketoacyl-ACP (β-ketoacyl-ACP synthase), reduction of the keto-function to an alcohol (β-ketoacyl-ACP reductase), dehydration to form an enoyl-ACP (β-hydroxyacyl-ACP dehydrase), and finally reduction of the enoyl-ACP to form the elongated saturated acyl-ACP (enoyl-ACP reductase). β-ketoacyl-ACP synthase I (KAS I), is primarily responsible for elongation up to palmitoyl-ACP (C16:0), whereas β-ketoacyl-ACP synthase II (KAS II) is predominantly responsible for the final elongation to stearoyl-ACP (C18:0).

Genes encoding peptide components of β-ketoacyl-ACP synthases I and II have been cloned from a number of higher plant species, including castor (*Ricinus communis*) and *Brassica* species (U.S. Pat. No. 5,510,255). KAS I activity was associated with a single synthase protein factor having an approximate molecular weight of 50 kD (synthase factor B) and KAS II activity was associated with a combination of two synthase protein factors, the 50 kD synthase factor B and a 46 kd protein designated synthase factor A. Cloning and sequence of a plant gene encoding a KAS III protein has been reported by Tai and Jaworski (*Plant Physiol*. (1993) 103:1361-1367).

The end products of plant fatty acid synthetase activities are usually 16- and 18-carbon fatty acids. There are, however, several plant families that store large amounts of 8- to 14-carbon (medium-chain) fatty acids in their oilseeds. Recent studies with *Umbellularia californica* (California bay), a plant that produces seed oil rich in lauric acid (12:0), have demonstrated the existence of a medium-chain-specific isozyme of acyl-ACP thioesterase in the seed plastids. Subsequent purification of the 12:0-ACP thioesterase from *Umbellularia californica* led to the cloning of a thioesterase cDNA which was expressed in seeds of *Arabidopsis* and *Brassica* resulting in a substantial accumulation of lauric acid in the triglyceride pools of these transgenic seeds (U.S. Pat. No. 5,512,482). These results and subsequent studies with medium-chain thioesterases from other plant species have confirmed the chain-length-determining role of acyl-ACP thioesterases during de novo fatty acid biosynthesis (T. Voelker (1996) *Genetic Engineering*, Ed. J. K. Setlow, Vol. 18, pgs. 111-133).

DESCRIPTION OF THE FIGURES

FIG. 1. DNA (SEQ ID NO: 1) and translated amino acid sequence (SEQ ID NO: 2) of *Cuphea hookeriana* KAS factor B clone chKAS B-2 are provided.

FIG. 2. DNA (SEQ ID NO: 3) and translated amino acid sequence (SEQ ID NO: 4) of *Cuphea hookeriana* KAS factor B clone chKAS B-31-7 are provided.

FIG. 3. DNA (SEQ ID NO: 5) and translated amino acid sequence (SEQ ID NO: 6) of *Cuphea hookeriana* KAS factor A clone chKAS A-2-7 are provided.

FIG. 4. DNA (SEQ ID NO: 7) and translated amino acid sequence (SEQ ID NO: 8) of *Cuphea hookeriana* KAS factor A clone chKAS A-1-6 are provided.

FIG. 5. DNA (SEQ ID NO: 9) and translated amino acid sequence (SEQ ID NO: 10) of *Cuphea pullcherrima* KAS factor B clone cpuKAS B/7-8 are provided.

FIG. 6. DNA (SEQ ID NO: 11) and translated amino acid sequence (SEQ ID NO: 12) of *Cuphea pullcherrima* KAS factor B clone cpuKAS B/8-7A are provided.

FIG. 7. DNA (SEQ ID NO: 13) and translated amino acid sequence (SEQ ID NO: 14) of *Cuphea pullcherrima* KAS factor A clone cpuKAS A/p7-6A are provided.

FIG. 8. Preliminary DNA sequence (SEQ ID NO: 15) of *Cuphea pullcherrima* KAS factor A clone cpuKAS A/p8-9A is provided.

FIG. 9. DNA (SEQ ID NO: 16) and translated amino acid sequence (SEQ ID NO: 17) of *Cuphea hookeriana* KASIII clone chKASIII-27 are provided.

FIG. 19C. Graph showing the % C12:0 in transgenic plants resulting from cross of plants containing Uc FatB1 (LA86DH186) and lines expressing Ch KAS A-2-7 is provided.

SUMMARY OF THE INVENTION

Figure 10:
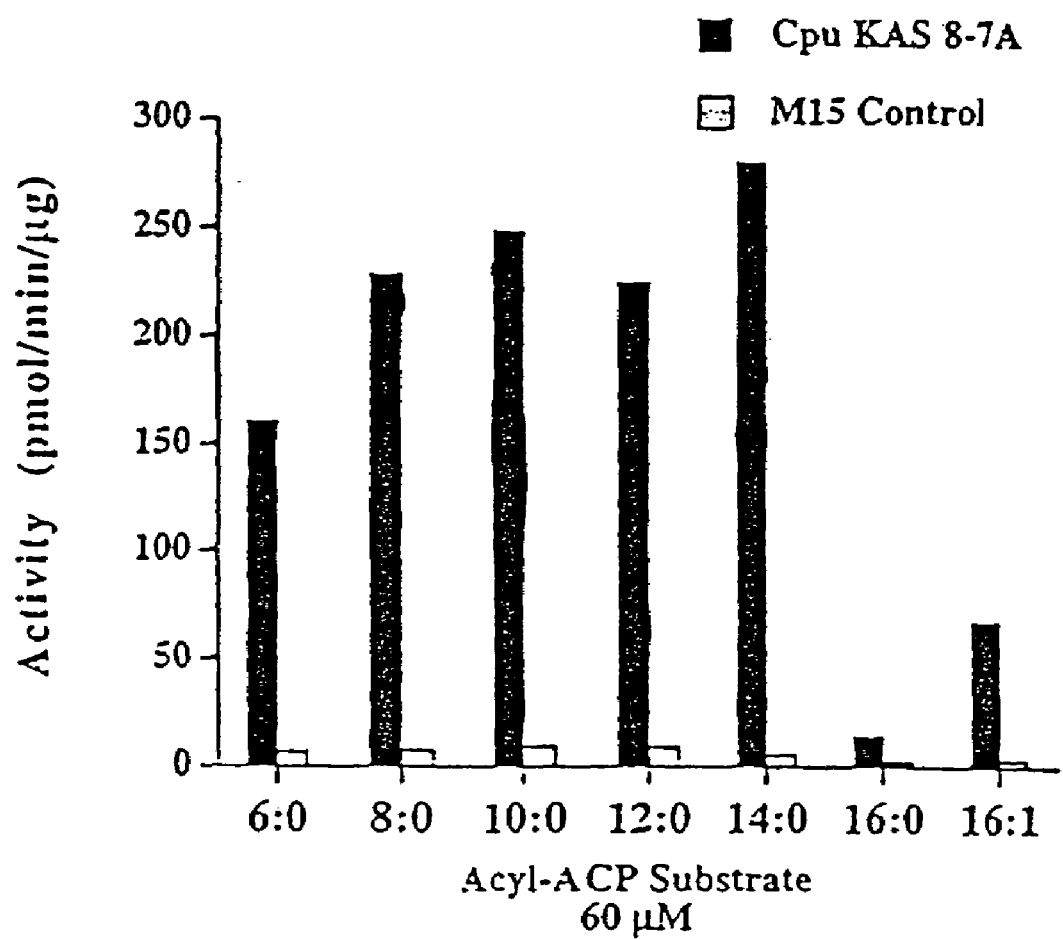
FIG. 10. The activity profile for purified cpuKAS B/8-7A using various acyl-ACP substrates is provided.

By this invention, compositions and methods of use related to β-ketoacyl-ACP synthase (KAS) are provided. Also of interest are methods and compositions of amino acid and nucleic acid sequences related to biologically active plant synthase(s).

In particular, genes encoding KAS protein factors A and B from *Cuphea* species are provided. The KAS genes are of interest for use in a variety of applications, and may be used to provide synthase I and/or synthase II activities in transformed host cells, including bacterial cells, such as *E. coli*, and plant cells. Synthase activities are distinguished by the preferential activity towards longer and shorter acyl-ACPs as well as by the sensitivity towards the KAS specific inhibitor, cerulenin. Synthase protein preparations having preferential activity towards medium chain length acyl-ACPs are synthase I-type or KAS I. The KAS I class is sensitive to inhibition by cerulenin at concentrations as low as 1 µM. Synthases having preferential activity towards longer chain length acyl-ACPs are synthase II-type or KAS II. The KAS enzymes of the II-type are also sensitive to cerulenin, but at higher concentrations (50 µM). Synthase III-type enzymes have preferential activity towards short chain length acyl-ACPs and are insensitive to cerulenin inhibition.

Nucleic acid sequences encoding a synthase protein may be employed in nucleic acid constructs to modulate the amount of synthase activity present in the host cell, especially the relative amounts of synthase I-type, synthase II-type and synthase III-type activity when the host cell is a plant host cell. In addition, nucleic acid constructs may be designed to decrease expression of endogenous synthase in a plant cell as well. One example is the use of an anti-sense synthase sequence under the control of a promoter capable of expression in at least those plant cells which normally produce the enzyme.

Of particular interest in the present invention is the coordinate expression of a synthase protein with the expression of thioesterase proteins. For example, coordinated expression of synthase factor A and a medium-chain thioesterase provides a method for increasing the level of medium-chain fatty acids which may be harvested from transgenic plant seeds. Furthermore, coordinated expression of a synthase factor A gene with plant medium-chain thioesterase proteins also provides a method by which the ratios of various medium-chain fatty acids produced in a transgenic plant may be modified. For example, by expression of a synthase factor A, it is possible to increase the ratio of C10/C8 fatty acids which are produced in plant seed oils as the result of expression of a thioesterase having activity on C8 and C10 fatty acids.

DETAILED DESCRIPTION OF THE INVENTION

A plant synthase factor protein of this invention includes a sequence of amino acids or polypeptide which is required for catalyzation of a condensation reaction between an acyl-ACP having a chain length of $C_2$ to $C_{16}$ and malonyl-ACP in a plant host cell. A particular plant synthase factor protein may be capable of catalyzing a synthase reaction in a plant host cell (for example as a monomer or homodimer) or may be one component of a multiple peptide enzyme which is capable of catalyzing a synthase reaction in a plant host cell, i.e. one peptide of a heterodimer.

Synthase I (KAS I) demonstrates preferential activity towards acyl-ACPs having shorter carbon chains, $C_2$-$C_{14}$ and is sensitive to inhibition by cerulenin at concentrations of 1 µM. Synthase II (KAS II) demonstrates preferential activity towards acyl-ACPs having longer carbon chains, $C_{14}$-$C_{16}$, and is inhibited by concentrations of cerulenin (50 µM). Synthase III demonstrates preferential activity towards acyl-CoAs having very short carbon chains, $C_2$ to $C_6$, and is insensitive to inhibition by cerulenin.

Synthase factors A and B, and synthase III proteins obtained from medium-chain fatty acid producing plant species of the genus *Cuphea* are described herein. As described in the following Examples, synthase A from *C. hookeriana* is naturally expressed at a high level and only in the seeds. *C. hookeriana* synthase B is expressed at low levels in all tissues examined. Expression of synthase A and synthase B factors in *E. coli* and purification of the resulting proteins is employed to determine activity of the various synthase factors. Results of these analyses indicate that synthase factor A from *Cuphea hookeriana* has the greatest activity on 6:0-ACP substrates, whereas synthase factor B from *Cuphea pullcherrima* has greatest activity on 14:0-ACP. Similar studies with synthase factors A and B from castor demonstrate similar activity profiles between the factor B synthase proteins from *Cuphea* and castor. The synthase A clone from castor, however, demonstrates a preference for 14:0-ACP substrate.

Expression of a *Cuphea hookeriana* KAS A protein in transgenic plant seeds which normally do not produce medium-chain fatty acids does not result in any detectable modification of the fatty acid types and contents produced in such seeds. However, when *Cuphea hookeriana* KAS A protein is expressed in conjunction with expression of a medium-chain acyl-ACP thioesterase capable of providing for production of C8 and C10 fatty acids in plant seed oils, increases in the levels of medium-chain fatty acids over the levels obtainable by expression of the medium-chain thioesterase alone are observed. In addition, where significant amounts of C8 and C10 fatty acids are produced as the result of medium-chain thioesterase expression, co-expression of a *Cuphea* KAS A protein also results in an alteration of the proportion of the C8 and C10 fatty acids that are obtained. For example, an increased proportion of C10 fatty acids may be obtained by co-expression of *Cuphea hookeriana* ChFatB2 thioesterase and a chKAS A synthase factor proteins.

Furthermore, when *Cuphea hookeriana* KAS A protein is expressed in conjunction with expression of a medium-chain acyl-ACP thioesterase capable of providing for production of C12 fatty acids in plant seed oils, increases in the levels of medium-chain fatty acids over the levels obtainable by expression of the medium-chain thioesterase alone are also observed. In addition, where significant amounts of C12 and C14 fatty acids are produced as the result of medium-chain thioesterase expression, co-expression of a *Cuphea* KAS A protein also results in an alteration of the proportion of the C12 and C14 fatty acids that are obtained. For example, an increased proportion of C12 fatty acids may be obtained by co-expression of Uc FatB1 thioesterase and a chKAS A synthase factor proteins.

However, when *Cuphea hookeriana* KAS A protein is expressed in conjunction with the expression of a long-chain acyl-ACP thioesterase capable of providing for production of C18 and C18:1 fatty acids in plant seed oils, no effect on the production of long chain fatty acids was observed. Furthermore, when plants transformed to express a long chain acyl-ACP thioesterase from mangosteen (GarmFatA1, U.S. patent application Ser. No. 08/440,845), which preferentially hydrolyzes C18:0 and C18:1 fatty acyl-ACPs, are crossed with nontransformed control plants, a significant reduction in the levels of C18:0 is obtained. Similar reductions are also observed in the levels of C18:0 in the seeds of plants resulting from crosses between plants transformed to express the GarmFatA1 and plants expressing the *Cuphea hookeriana* KAS A protein.

Thus, the instant invention provides methods of increasing and/or altering the medium-chain fatty acid compositions in transgenic plant seed oils by co-expression of medium-chain acyl-ACP thioesterases with synthase factor proteins. Furthermore, various combinations of synthase factors and medium-chain thioesterases may be achieved depending upon the particular fatty acids desired. For example, for increased production of C14 fatty acids, synthase protein factors may be expressed in combination with a C14 thioesterase, for example from *Cuphea palustris* or nutmeg may be employed (WO 96/23892). In addition, thioesterase expression may be combined with a number of different synthase factor proteins for additional effects on medium-chain fatty acid composition.

Synthases of use in the present invention include modified amino acid sequences, such as sequences which have been mutated, truncated, increased and the like, as well as such sequences which are partially or wholly artificially synthesized. The synthase protein encoding sequences provided herein may be employed in probes for further screening or used in genetic engineering constructs for transcription or transcription and translation in host cells, especially plant host cells. One skilled in the art will readily recognize that antibody preparations, nucleic acid probes (DNA and RNA) and the like may be prepared and used to screen and recover synthases and/or synthase nucleic acid sequences from other sources. Typically, a homologously related nucleic acid sequence will show at least about 60% homology, and more preferably at least about 70% homology, between the *R. communis* synthase and the given plant synthase of interest, excluding any deletions which may be present. Homology is determined upon comparison of sequence information, nucleic acid or amino acid, or through hybridization reactions.

Recombinant constructs containing a nucleic acid sequence encoding a synthase protein factor or nucleic acid sequences encoding a synthase protein factor and a medium-chain acyl-ACP thioesterase may be prepared by methods well known in the art. Constructs may be designed to produce synthase in either prokaryotic or eukaryotic cells. The increased expression of a synthase in a plant cell, particularly in conjunction with expression of medium-chain thioesterases, or decreasing the amount of endogenous synthase observed in plant cells are of special interest.

Synthase protein factors may be used, alone or in combination, to catalyze the elongating condensation reactions of fatty acid synthesis depending upon the desired result. For example, rate influencing synthase activity may reside in synthase I-type, synthase II-type, synthase III-type or in a combination of these enzymes. Furthermore, synthase activities may rely on a combination of the various synthase factors described herein.

Constructs which contain elements to provide the transcription and translation of a nucleic acid sequence of interest in a host cell are "expression cassettes". Depending upon the host, the regulatory regions will vary, including regions from structural genes from viruses, plasmid or chromosomal genes, or the like. For expression in prokaryotic or eukaryotic microorganisms, particularly unicellular hosts, a wide variety of constitutive or regulatable promoters may be employed. Among transcriptional initiation regions which have been described are regions from bacterial and yeast hosts, such as *E. coli, B. subtilis, Saccharomyces cerevisiae*, including genes such as β-galactosidase, T7 polymerase, trp-lac (tac), trp E and the like.

An expression cassette for expression of synthase in a plant cell will include, in the 5' to 3' direction of transcription, a transcription and translation initiation control regulatory region (also known as a "promoter") functional in a plant cell, a nucleic acid sequence encoding a synthase, and a transcription termination region. Numerous transcription initiation regions are available which provide for a wide variety of constitutive or regulatable, e.g., inducible, transcription of the desaturase structural gene. Among transcriptional initiation regions used for plants are such regions associated with cauliflower mosaic viruses (35S, 19S), and structural genes such as for nopaline synthase or mannopine synthase or napin and ACP promoters, etc. The transcription/translation initiation regions corresponding to such structural genes are found immediately 5' upstream to the respective start codons. Thus, depending upon the intended use, different promoters may be desired.

Of special interest in this invention are the use of promoters which are capable of preferentially expressing the synthase in seed tissue, in particular, at early stages of seed oil formation. Examples of such seed-specific promoters include the region immediately 5' upstream of a napin or seed ACP genes such as described in U.S. Pat. No. 5,420,034, desaturase genes such as described in Thompson et al (*Proc. Nat. Acad. Sci.* (1991) 88:2578-2582), or a Bce-4 gene such as described in U.S. Pat No. 5,530,194. Alternatively, the use of the 5' regulatory region associated with the plant synthase structural gene, i.e., the region immediately 5' upstream to a plant synthase structural gene and/or the transcription termination regions found immediately 3' downstream to the plant synthase structural gene, may often be desired. In general, promoters will be selected based upon their expression profile which may change given the particular application.

In addition, one may choose to provide for the transcription or transcription and translation of one or more other sequences of interest in concert with the expression or anti-sense of the synthase sequence, particularly medium-chain plant thioesterases-such as described in U.S. Pat No. 5,512,482, to affect alterations in the amounts and/or composition of plant oils.

When one wishes to provide a plant transformed for the combined effect of more than one nucleic acid sequence of interest, a separate nucleic acid construct may be provided for each or the constructs may both be present on the same plant transformation construct. The constructs may be introduced into the host cells by the same or different methods, including the introduction of such a trait by crossing transgenic plants via traditional plant breeding methods, so long as the resulting product is a plant having both characteristics integrated into its genome.

Normally, included with the DNA construct will be a structural gene having the necessary regulatory regions for expression in a host and providing for selection of transformed cells. The gene may provide for resistance to a cytotoxic agent, e.g. antibiotic, heavy metal, toxin, etc., complementation providing prototrophy to an auxotrophic host, viral immunity or the like. Depending upon the number of different host species into which the expression construct or components thereof are introduced, one or more markers may be employed, where different conditions for selection are used for the different hosts.

The manner in which the DNA construct is introduced into the plant host is not critical to this invention. Any method which provides for efficient transformation may be employed. Various methods for plant cell transformation include the use of Ti- or Ri-plasmids, microinjection, electroporation, liposome fusion, DNA bombardment or the like. In many instances, it will be desirable to have the construct bordered on one or both sides by T-DNA, particularly having the left and right borders, more particularly the right border. This is particularly useful when the construct uses *A. tumefaciens* or *A. rhizogenes* as a mode for transformation, although the T-DNA borders may find use with other modes of transformation.

The expression constructs may be employed with a wide variety of plant life, particularly plant life involved in the production of vegetable oils. These plants include, but are not limited to rapeseed, peanut, sunflower, safflower, cotton, soybean, corn and oilseed palm.

For transformation of plant cells using *Agrobacterium*, explants may be combined and incubated with the transformed *Agrobacterium* for sufficient time for transformation, the bacteria killed, and the plant cells cultured in an appropriate selective medium. Once callus forms, shoot formation can be encouraged by employing the appropriate plant hormones in accordance with known methods and the shoots transferred to rooting medium for regeneration of plants. The plants may then be grown to seed and the seed used to establish repetitive generations and for isolation of vegetable oils.

The invention now being generally described, it will be more readily understood by reference to the following examples which are included for purposes of illustration only and are not intended to limit the present invention.

EXAMPLES

Example 1

*Cuphea* KAS Factor A and B Gene Cloning

Total RNA isolated from developing seeds of *Cuphea hookeriana* and *Cuphea pullcherrima* was used for cDNA synthesis in commercial 1-based cloning vectors. For cloning each type of KAS gene, approximately 400,000-500,000 unamplified recombinant phage were plated and the plaques transferred to nitrocellulose. For KAS factor B cloning from *C. hookeriana*, a mixed probe containing *Brassica napus* KAS factor B and *Ricinus communis* (Castor) KAS factor B radiolabeled cDNA's was used. Similarly, a mixed probe containing *Brassica napus* KAS factor A and *Ricinus communis* KAS factor A cDNA clones was used to obtain *C. hookeriana* KAS factor A genes. For KASIII, a spinach KASIII cDNA clone obtained from Dr. Jan Jaworski was radiolabeled and used as a probe to isolate a KASIII clone from *C. hookeriana*. For KAS B and KAS A cloning from *C. pullcherrima*, *C. hookeriana* KAS B and KAS A genes chKAS B-2 and chKAS A-2-7 (see below) were radiolabeled and used as probes.

DNA sequence and translated amino acid sequence for *Cuphea* KAS clones are provided in FIGS. 1-9. *Cuphea hookeriana* KAS factor B clones chKAS B-2 and chKAS B-31-7 are provided in FIGS. 1 and 2. Neither of the clones is full length. *Cuphea hookeriana* KAS Factor A clones chKAS A-2-7 and chKAS A-1-6 are provided in FIGS. 3 and 4. chKAS A-2-7 contains the entire encoding sequence for the KAS factor protein. Based on comparison with other plant synthase proteins, the transit peptide is believed to be represented in the amino acids encoded by nucleotides 125-466. chKAS A-1-6 is not a full length clone although some transit peptide encoding sequence is present. Nucleotides 1-180 represent transit peptide encoding sequence, and the mature protein encoding sequence is believed to begin at nucleotide 181.

*Cuphea pullcherrima* KAS factor B clones cpuKAS B/7-8 and cpuKAS B/8-7A are provided in FIGS. 5 and 6. Both of the clones contain the entire encoding sequences for the KAS factor B proteins. The first 35 amino acids of cpuKAS B/7-8 are believed to represent the transit peptide, with the mature protein encoding sequence beginning at nucleotide 233. The first 39 amino acids of cpuKAS B/8-7A are believed to represent the transit peptide, with the mature protein encoding sequence beginning at nucleotide 209.

*Cuphea pullcherrima* KAS factor A clones cpuKAS A/p7-6A and cpuKAS A-p8-9A are provided in FIGS. 7 and 8. Both of the clones contain the entire encoding sequences for the KAS factor A proteins. Translated amino acid sequence of cpuKAS A/p7-6A is provided. The mature protein is believed to begin at the lysine residue encoded 595-597, and the first 126 amino acids are believed to represent the transit peptide. The DNA sequence of KAS A clone cpuKAS Ap8-9A is preliminary. Further analysis will be conducted to determine final DNA sequence and reveal the amino acid sequence encoded by this gene.

DNA and translated amino acid sequence of *Cuphea hookeriana* KASIII clone chKASIII-27 is provided in FIG. 9. The encoding sequence from nucleotides 37-144 of chKASIII-27 are believed to encode a transit peptide, and the presumed mature protein encoding sequence is from nucleotides 145-1233.

Deduced amino acid sequence of the *C. hookeriana* KAS factor B and KAS factor A cDNA's reveals strong homology to the *Brassica napus* and *Ricinus communis* clones previously reported. The *C. hookeriana* KAS factor B clone is more homologous to the *Ricinus* and *Brassica* KAS factor B clones (94% and 91% respectively) than it is to the *Ricinus* and *Brassica* KAS factor A clones (60% for both). Furthermore, the *C. hookeriana* KAS factor A clone is more homologous to the *Ricinus* and *Brassica* KAS factor A clones (85% and 82% respectively) than it is the *Ricinus* and *Brassica* KAS factor B clone (60% for both). The *C. hookeriana* KAS factor B cDNAs designated as chKAS B-2 and chKAS B-31-7 are 96% identical within the mature portion of the polypeptide. Similarly, the deduced amino acid sequence of the mature protein regions of the *C. hookeriana* KAS factor A clones chKAS A-2-7 and chKAS A-1-6 are 96% identical. The *C. pullcherrima* KAS clones also demonstrate homology to the *R. communis* and *Brassica napus* KAS clones. The mature protein portion of all of the KAS factor A family members in the different *Cuphea* species are 95% identical. Similarly the mature protein portion of the KAS factor B genes in *Cuphea* are also 95-97% identical with each other. However there is only approximately 60% sequence identity between KAS factor B and KAS factor A clones either within the same or different species of *Cuphea*.

Example 2

Levels and Patterns of Expression

To examine tissue specificity of KAS expression in *Cuphea hookeriana*, Northern blot analysis was conducted using total RNA isolated from seed, root, leaf and flower tissue. Two separate but identical blots were hybridized with either chKAS B-31-7 or chKAS A-2-7 coding region probes. The data from this RNA blot analysis indicate that KAS B is expressed at a similar level in all tissues examined, whereas KAS A expression is detected only in the seed. These results also demonstrate a different level of expression for each of the synthases. KAS A is an abundant message, whereas KAS B is expressed at low levels. Furthermore, even under highly stringent hybridization conditions (65_C, 0.1×SSC, 0.5% SDS), the KAS A probe hybridizes equally well with two seed transcripts of 2.3 and 1.9 kb. The larger hybridizing band is likely the transcript of the KAS A-2-7 gene since the size of its cDNA is 2046bp, and the number of clones obtained from cDNA screening corresponds well with the apparent mobility of the mRNA and its abundance on the blot.

Example 3

Expression of Plant KAS Genes in *E.coli*

DNA fragments encoding the mature polypeptide of the *Cuphea hookeriana* KAS A cDNAs and the *Cuphea pullcherrima* KAS B cDNAs were obtained by PCR and cloned into a QIAexpress expression vector (Qiagene). Experimental conditions for maximum level of expression were determined for all of these clones and the parameters for highest level of soluble fraction were identified. Cells are grown in ECLB media containing 1M sorbitol and 2.5 mM betaine overnight and subcultured as a 1:4 dilution in the same medium. Cells are then grown for 2 hours (to approximately 0.6-0.8 O.D.) and induced with 0.4 mM IPTG and allowed to grow for 5 more hours.

Enzyme activity of the affinity purified recombinant enzymes obtained from over-expression of the chKAS A-2-7 and cpuKAS B/8-7A clones was measured using a wide range of acyl-ACP substrates (6:0- to 16:1-ACP). The activity profile for cpuKAS B/8-7A is provided in FIG. 10. The data demonstrate that the enzyme is active with all acyl-ACP substrates examined, although activity on 6:0 to 14:0-ACP substrates is substantially greater than the activity on 16:0 and 16:1 substrates.

Figure 11:
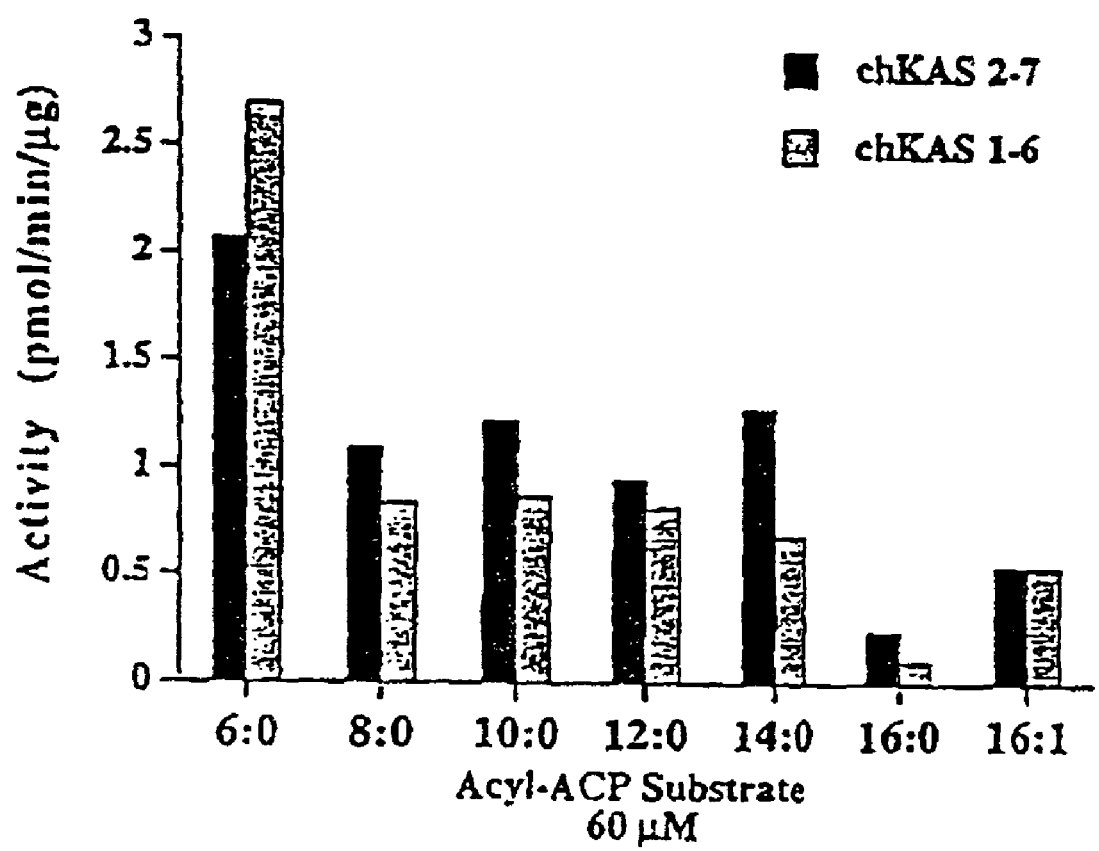
FIG. 11. The activity profile for purified chKAS A-2-7 and chKAS A-1-6 using various acyl-ACP substrates is provided.

The activity profile of the *C. hookeriana* KAS A clones chKAS A-2-7 and chKAS A-1-6 is provided in FIG. 11. The *C. hookeriana* KAS A clones are most active with C:6, and have the least activity with C:16:0 substrates. However, the activity of this clone on even the preferred C6:0 substrate is 50 fold lower than the activity of the *C. pullcherrima* KAS B clones.

Figure 12:
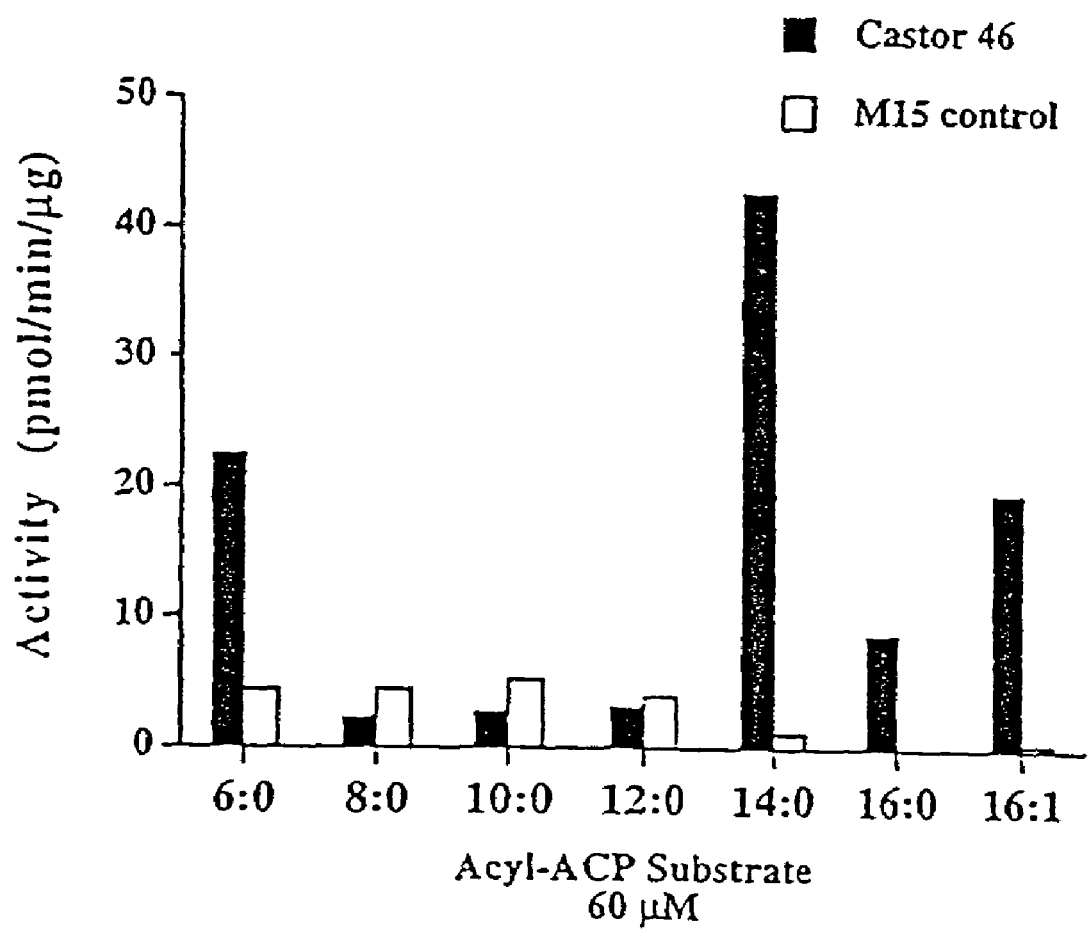
FIG. 12. The activity profile for purified castor KAS factor A using various acyl-ACP substrates is provided.
Figure 13:
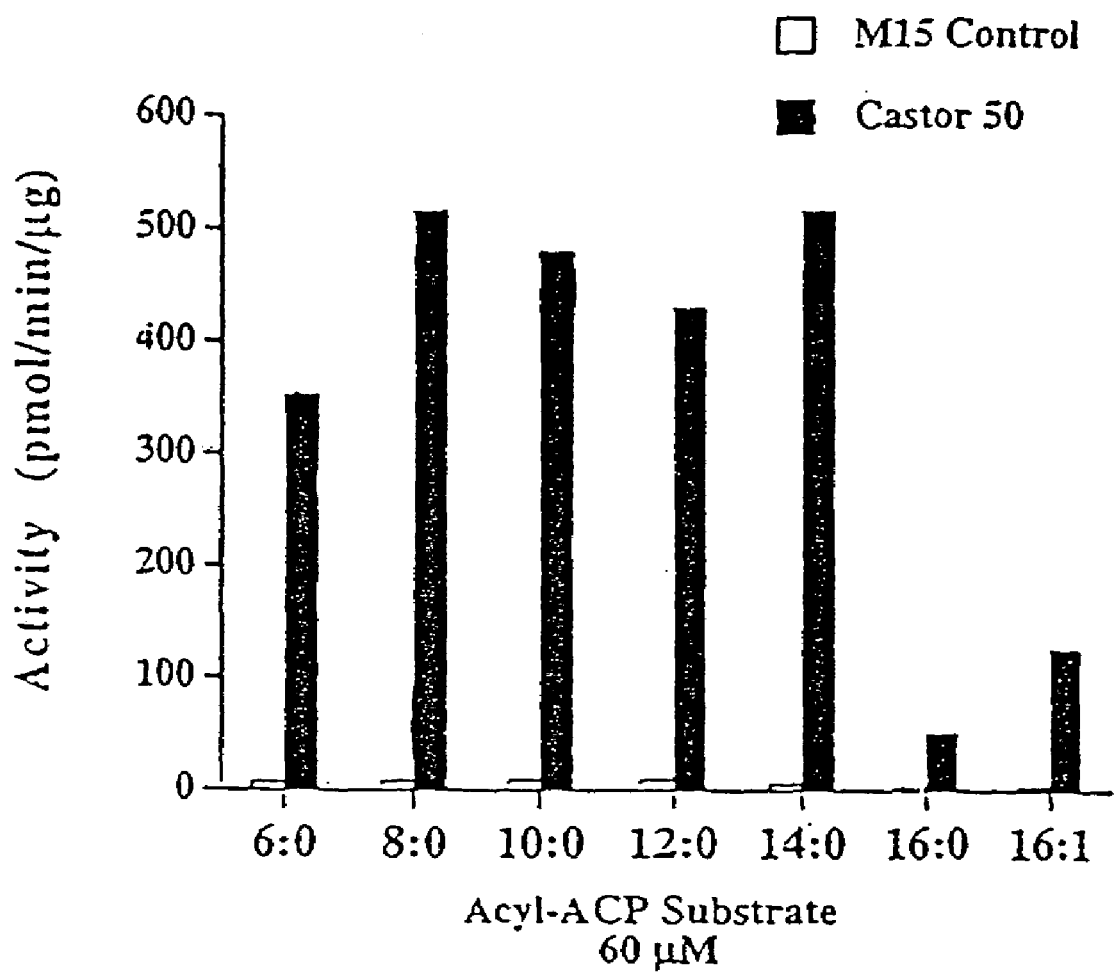
FIG. 13. The activity profile for purified castor KAS factor B using various acyl-ACP substrates is provided.

A fragment containing the mature protein encoding portion of a *R. communis* KAS factor A clone was also cloned into a QIAexpress expression vector, expressed in *E. coli* and the enzyme affinity purified as described above. The activity profile for castor KAS A is provided in FIG. 12. Highest activity is observed with C14:0 substrates, although some activity is also seen with C6:0 and C16:1. In comparison, the activity profile obtained from purified *R. communis* KAS factor B also using the QIAexpress expression system is provided in FIG. 13. The KAS B clone demonstrates substantially higher levels of activity (10 fold and higher) than the *R. communis* KAS A clone. The preference of the KAS factor B for 6:0- to 14:0-ACP substrates is consistent with the previous observations that this protein provides KAS I activity.

Example 4

KAS and TE Expression in Transgenic Seed

Both the CpFatB1 (*C. hookeriana* thioesterase cDNA; Dehesh et al. (1996) *Plant Physiol.* 110:203-210) and the chKAS A-2-7 were PCR amplified, sequenced, and cloned into a napin expression cassette. The napin/cp FatB1 and the napin/KAS A-2-7 fusions were ligated separately into the binary vector pCGN1558 (McBride and Summerfelt (*Pl.Mol.Biol.* (1990) 14:269-276) and transformed into *A. tumefaciens*, EHA101. The resulting CpFatB1 binary construct is pCGN5400 and the chKAS A-2-7 construct is pCGN5401. *Agrobacterium* mediated transformation of a *Brassica napus* canola variety was carried out as described by Radke et al. (*Theor. Appl. Genet.* (1988) 75:685-694; *Plant Cell Reports* (1992) 11:499-505). Several transgenic events were produced for each of the pCGN5400 and pCGN5401 constructs.

A double gene construct containing a napin/cpFatB1 expression construct in combination with a napin/chKAS A-2-7 expression construct was also assembled, ligated into a binary vector and used for co-cultivation of a canola *Brassica* variety. The binary construct containing the chFatB1 and chKAS A-2-7 expression constructs is pCGN5413.

Fatty acid analysis of 26 transgenic lines containing chKAS A-2-7 (5401 lines) showed no significant changes in the oil content or profile as compared to similar analyses of wild type canola seeds of the transformed variety.

Figure 14:
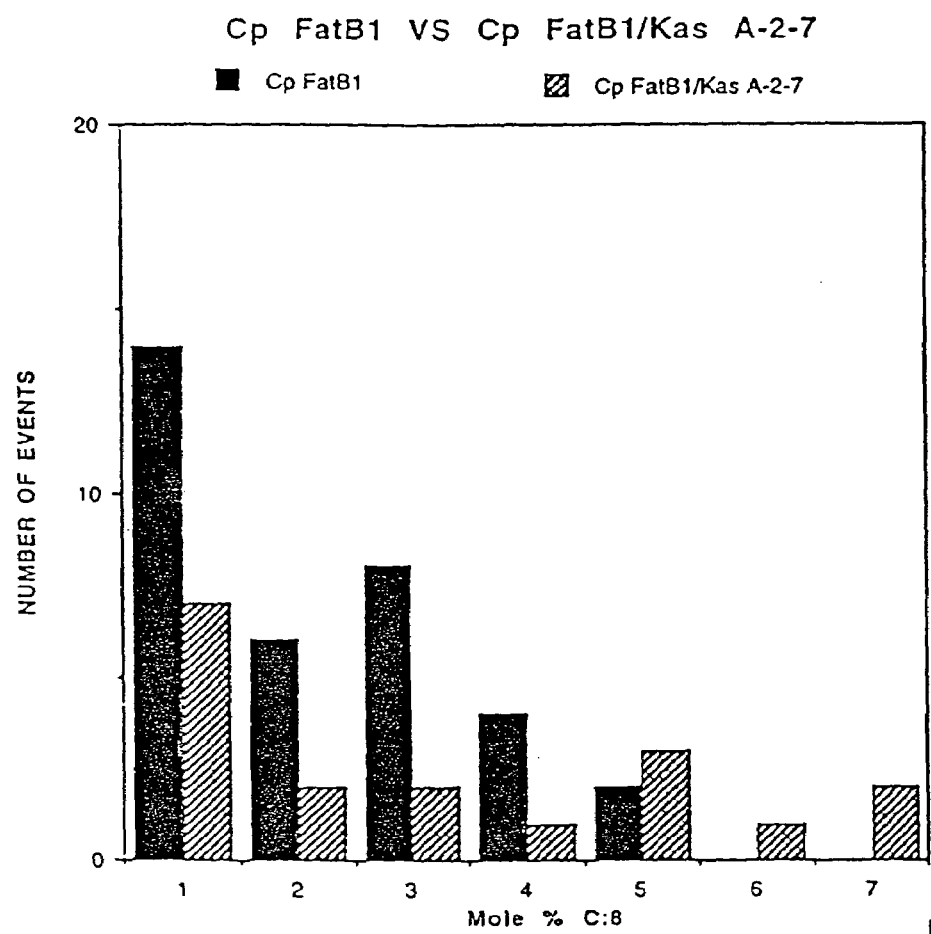
FIG. 14. A graph showing the number of plants arranged according to C8:0 content for transgenic plants containing CpFatB1 versus transgenic plants containing CpFatB1+chKAS A-2-7 is provided.

Fatty acid analysis of 36 transgenic lines containing cpFatB1 (5400 lines) showed increased levels of C:8 and C:10 in transgenic seeds. The highest level of C:8 observed in a pool seed sample was 4.2 mol %. The C:10 levels were between 30 and 35% of the C:8 content. Fatty acid analysis of 25 transgenic lines containing the TE/KAS A tandem (5413 lines) demonstrated an overall increase in both C:8 and C:10 levels relative to those observed with TE containing lines (5400) alone. In lines containing the cpFatB1 construct alone, the average level of C:8 average were 1.5 mol %, whereas the C:8 average levels in TE/KAS A tandem containing lines was 2.37 mol %. The ratio of C:8 to C:10 remained constant in both populations. The number of transgenic events relative to the C:8 content are presented in FIG. 14. These data show that the transgenic events with tandem TE/KAS A construct yield more lines with higher levels of C:8 than those events with single TE construct. For example, several lines containing nearly 7 mole % C8 were obtained with the TE/KAS A pCGN5413 construct, whereas the highest C8 containing line from the pCGN5400 TE alone transformation contained 4.2 mole % C8.

Half seed analysis of the T3 generation of transgenic canola plants expressing a ChFatB2 (*C. hookeriana* thioesterase; Dehesh et al. (1996) *The Plant Journal* 9:167-172) indicate that these plant can accumulate up to 22 weight % (33 mol %) of 8:0 and 10:0 fatty acids (4804-22-357). Segregation analysis shows that these transformants contain two loci and that they are now homozygous. Selected plants grown from these half seeds were transferred into the greenhouse and later crossed with T1 transformants that had been transformed with either *Cuphea hookeriana* KAS A (5401) alone or KAS A/CpFatB1 double constructs (5413).

Figure 15A:
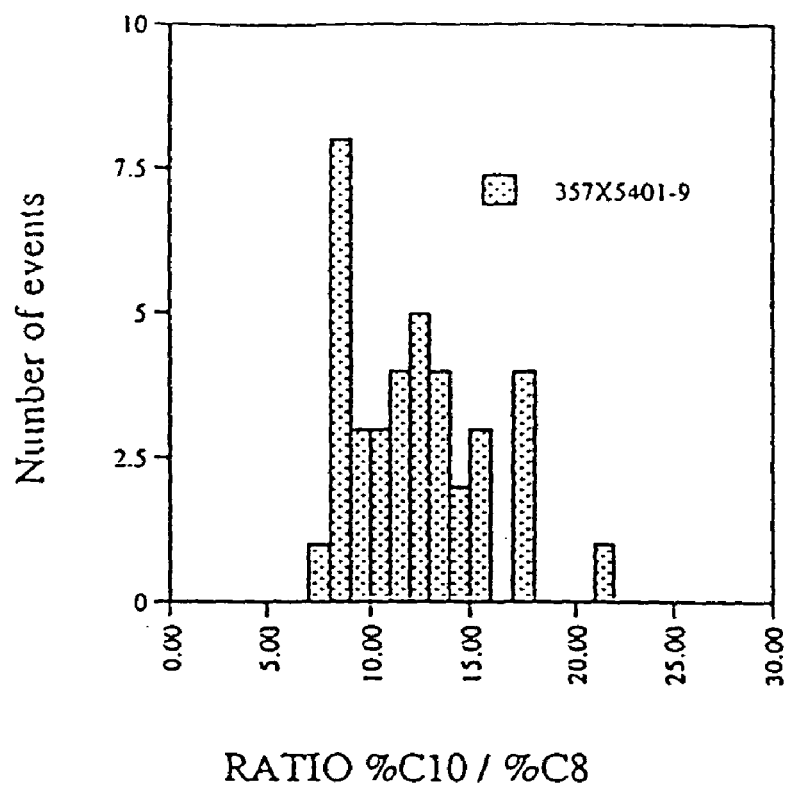
FIG. 15A. Graph showing the % C10/% C8 ratio in transgenic plants resulting from cross of plants containing ChFatB2 (4804-22-357) and 5401-9 (chKAS A-2-7 plants) is provided.
Figure 15B:
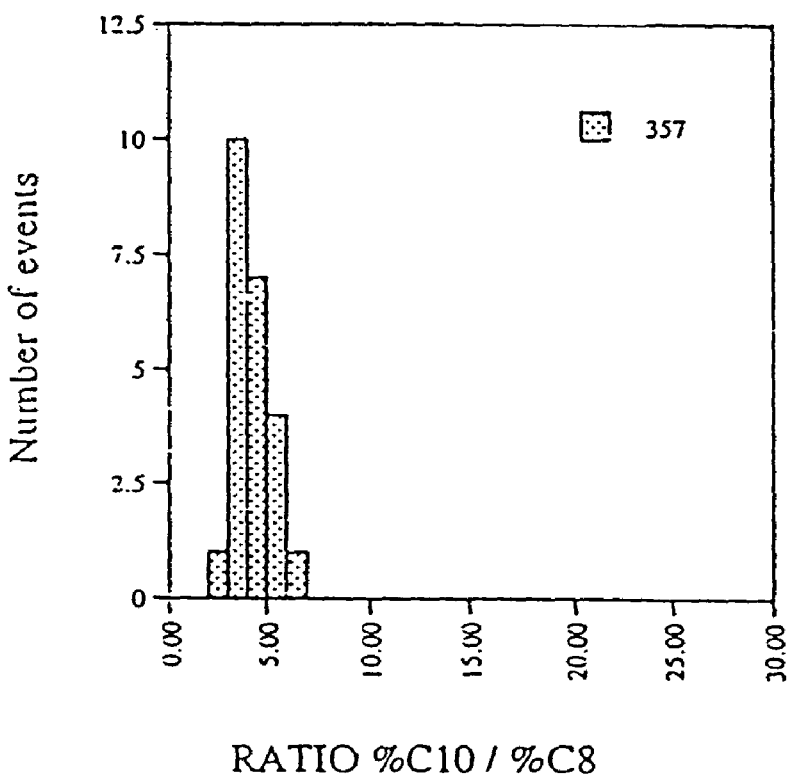
FIG. 15B. Graph showing the % C10/% C8 ratio in transgenic plants containing ChFatB2 (4804-22-357) is provided.
Figure 16A:
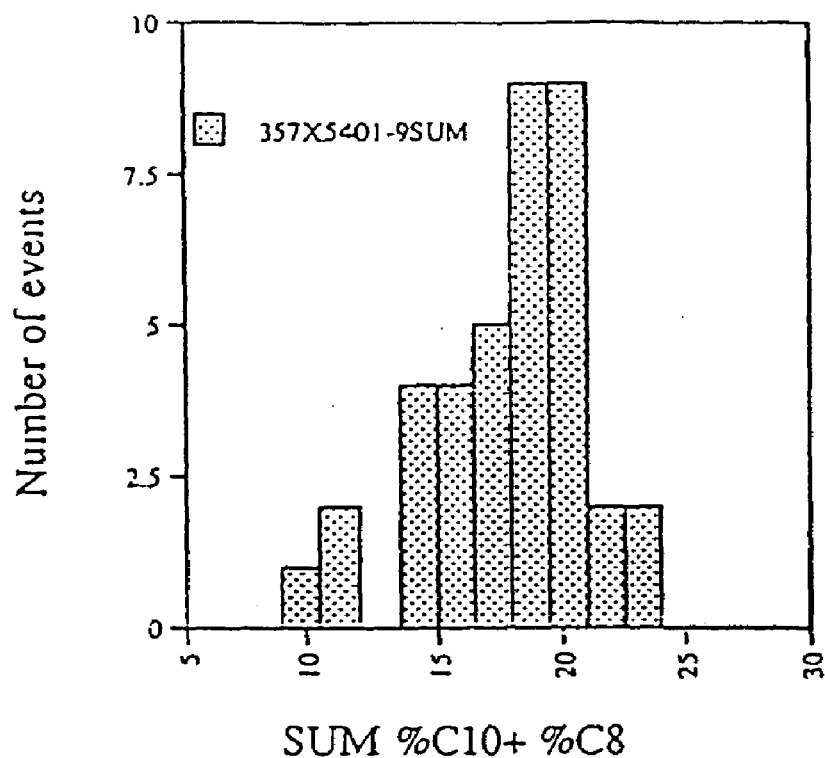
FIG. 16A. Graph showing the % C10+% C8 content in transgenic plants resulting from cross of plants containing ChFatB2 (4804-22-357) and 5401-9 (chKAS A-2-7 plants) is provided.
Figure 16B:
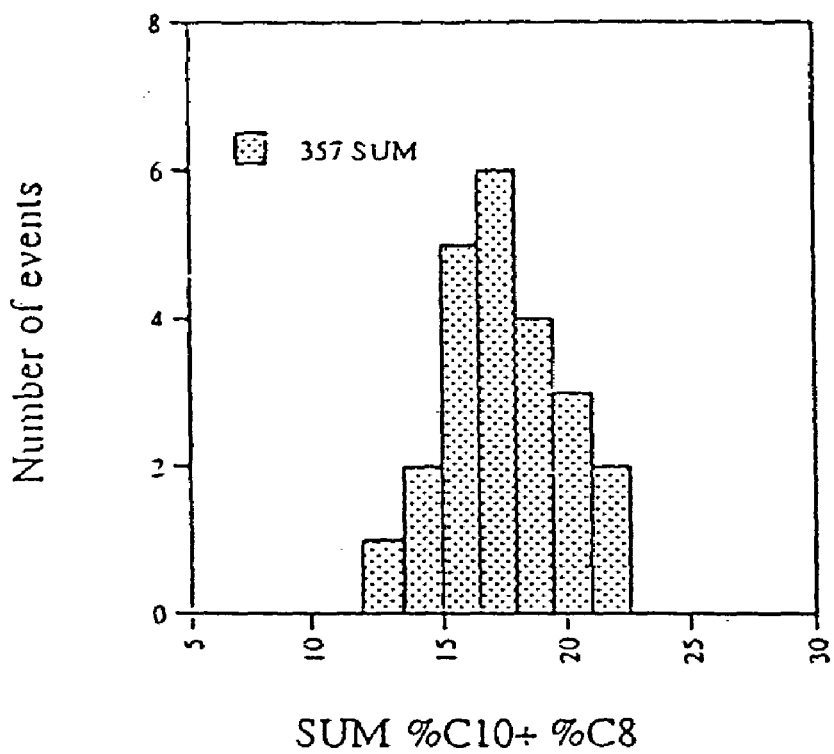
FIG. 16B. Graph showing the % C10+% C8 content in transgenic plants containing ChFatB2 (4804-22-357) is provided.

Fatty acid analysis of several events resulting from the crosses between transgenic lines containing ChFatB2 (4804-22-357) and chKAS A-2-7 (5401-9), reveal an increase in the ratio of C:10/C:8 levels (FIG. 15A and FIG. 15B). This C:10/C:8 ratio in nearly all of the transgenic events containing ChFatB2 TE alone fluctuates between 3 and 6, whereas in the F1 generation of transgenic containing both the TE and the KAS A-2-7, the ratio can be as high as 22. This increase in C:10 levels is accompanied by an increase in the total C:8 and C:10 content (FIG. 16A and 16B). The sum of the C:8 and C:10 fatty acids in the heterozygous F1 lines is as high as those in the homozygous parent line (4804-22-357), whereas the heterozygous lines usually contain substantially less C:8 and C:10 than the homozygous lines.

Figure 17A:
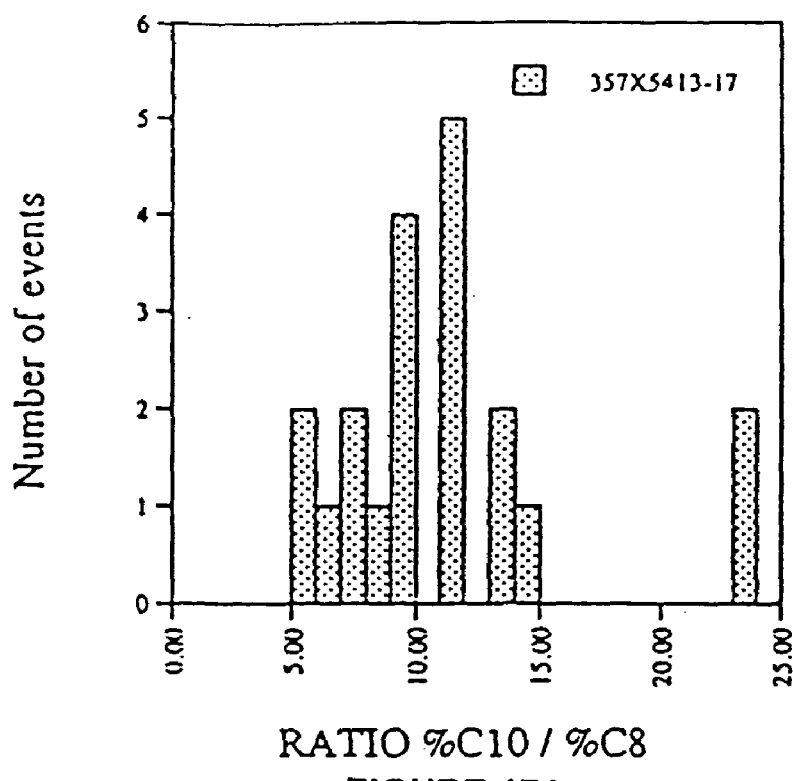
FIG. 17A. Graph showing the % C10/% C8 ratio in transgenic plants resulting from cross of plants containing ChFatB2 (4804-22-357) and 5413-17 (chKAS A-2-7+Cp-FatB1 plants) is provided.
Figure 17B:
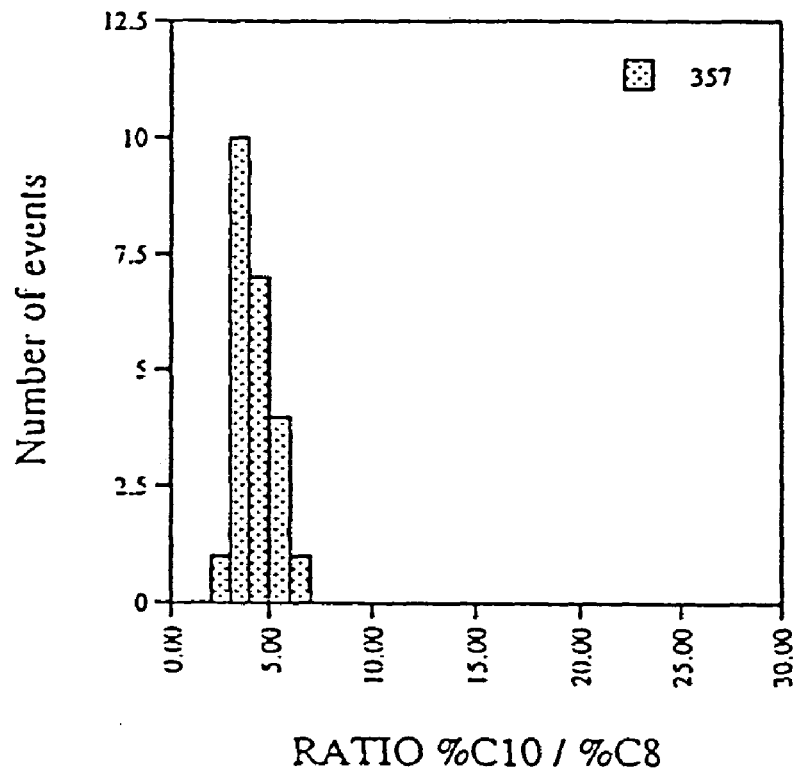
FIG. 17B. Graph showing the % C10/% C8 ratio in transgenic plants containing ChFatB2 (4804-22-357) is provided.
Figure 18A:
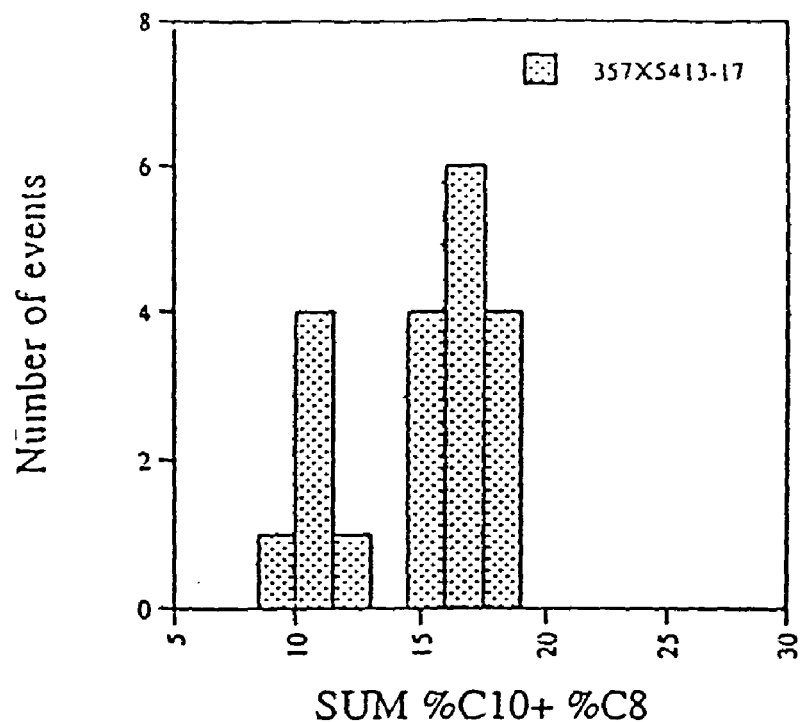
FIG. 18A. Graph showing the % C10+% C8 content in transgenic plants resulting from cross of plants containing ChFatB2 (4804-22-357) and 5413-17 (chKAS A-2-7+Cp-FatB1 plants) is provided.
Figure 18B:
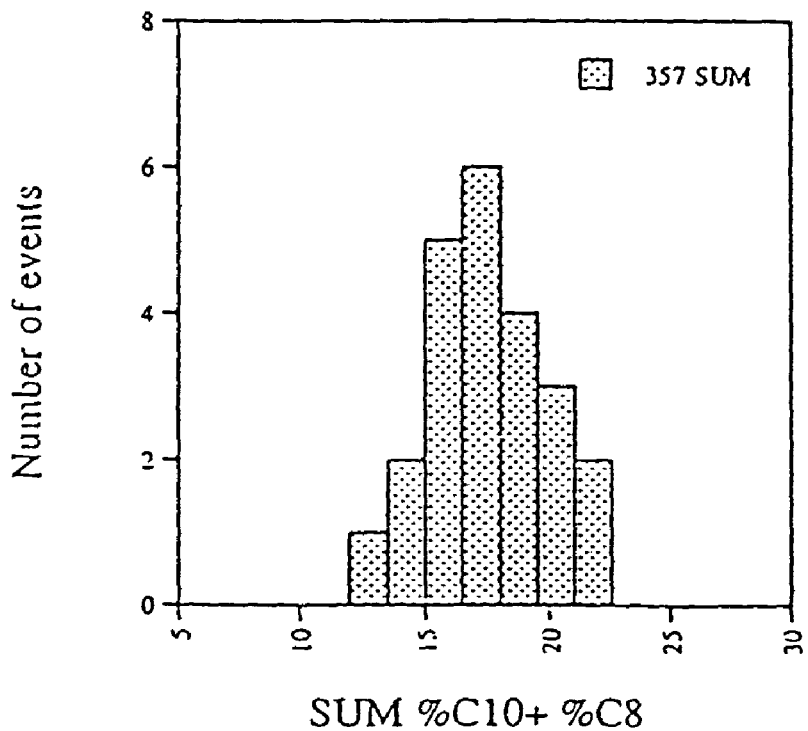
FIG. 18B. Graph showing the % C10+% C8 content in transgenic plants containing ChFatB2 (4804-22-357) is provided.

Similar results were observed in F1 generation seeds resulting from crosses performed between 4804-22-357 (ChFatB2) and the 5413-17 event (CpFatB1 and chKAS A-2-7 tandem). Levels of C:8 and C:10 in the 5413-17 line were 6.3 and 2.8 mol % respectively. Data presented in FIGS. 17A and 17B show that there is shift towards C:10 fatty acids as was observed with the 4804-22-357 (ChFatB2)×5401-9 (chKAS A-2-7) crosses. Furthermore, FIGS. 18A and 18B indicates the presence of two separate populations of heterozygotes. Those containing approximately 9-11 weight percent C:10+C:8 are believed to represent offspring containing a single copy of the ChFatB1 TE gene and no copies of the CpFatB1 and chKAS A genes from 5413. Those plants containing approximately 15-20 weight percent C:10+C:8 are believed to represent the heterozygotes containing a single ChFatB1 TE gene as well as the CpFatB1 and chKAS A genes from 5413. Thus, the level of the C:10+C:8 fatty acids does not decrease to 50% of that detected in parent lines when a copy of the ChKAS A gene is present.

To further characterize the chain length specificity of the *Cuphea hookeriana* KAS A enzyme, crosses between transgenic *Brassica napus* lines containing a California Bay (*Umbellularia californica*) 12:0 specific thioesterase, Uc FatB1 (U.S. Pat. No. 5,344,771) and chKAS A-2-7 (5401-9) were made. Half seed analysis of transgenic plants containing Uc fatB1 have previuosly indicated that these plants can accumulate up to 52 mol % C12:0 in the seed oil of homozygous dihaploid lines (LA86DH186). Crosses between the line LA86DH186 and untransformed control *Brassica* demonstrated a decrease in the C12:0 levels.

Figure 19A:
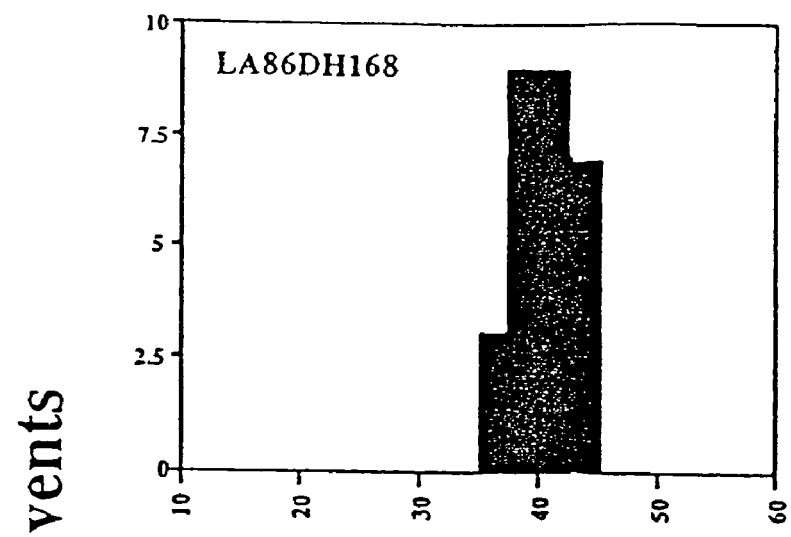
FIG. 19A. Graph showing the % C12:0 in transgenic plants containing Uc FatB1 (LA86DH186) is provided.
Figure 19B:
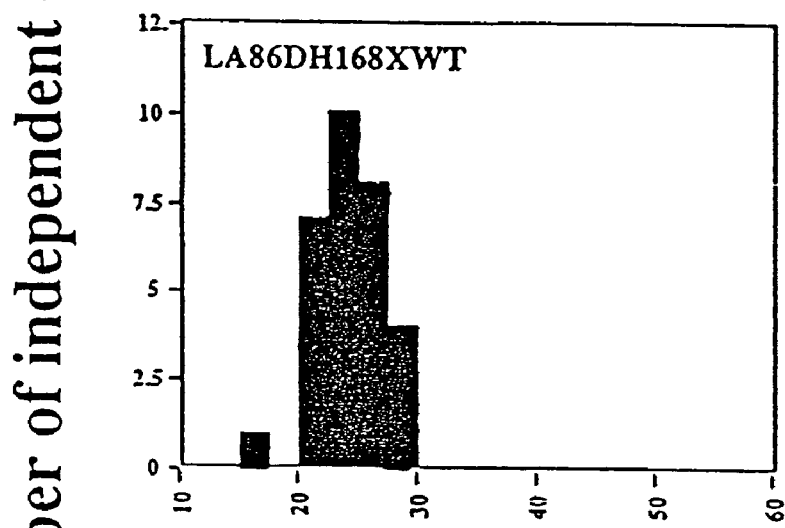
FIG. 19B. Graph showing the % C12:0 in transgenic plants resulting from cross of plants containing Uc FatB1 (LA86DH186) and wild type (X WT) is provided.
Figure 19B:
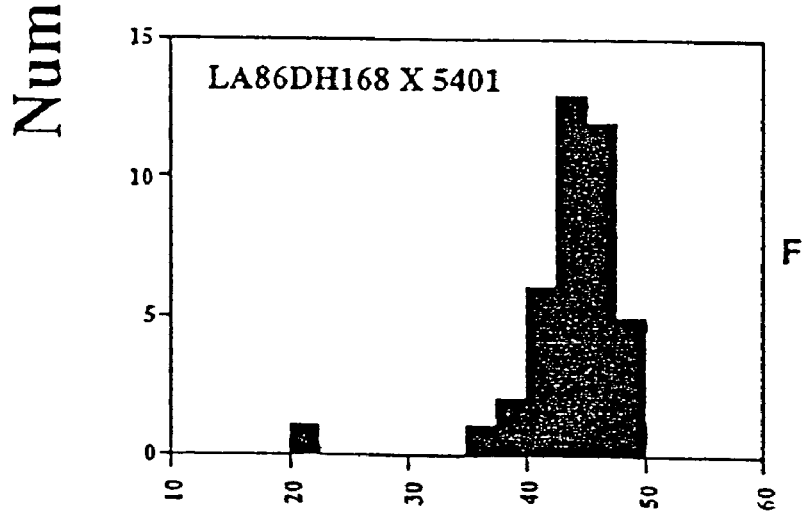
Figure 20:
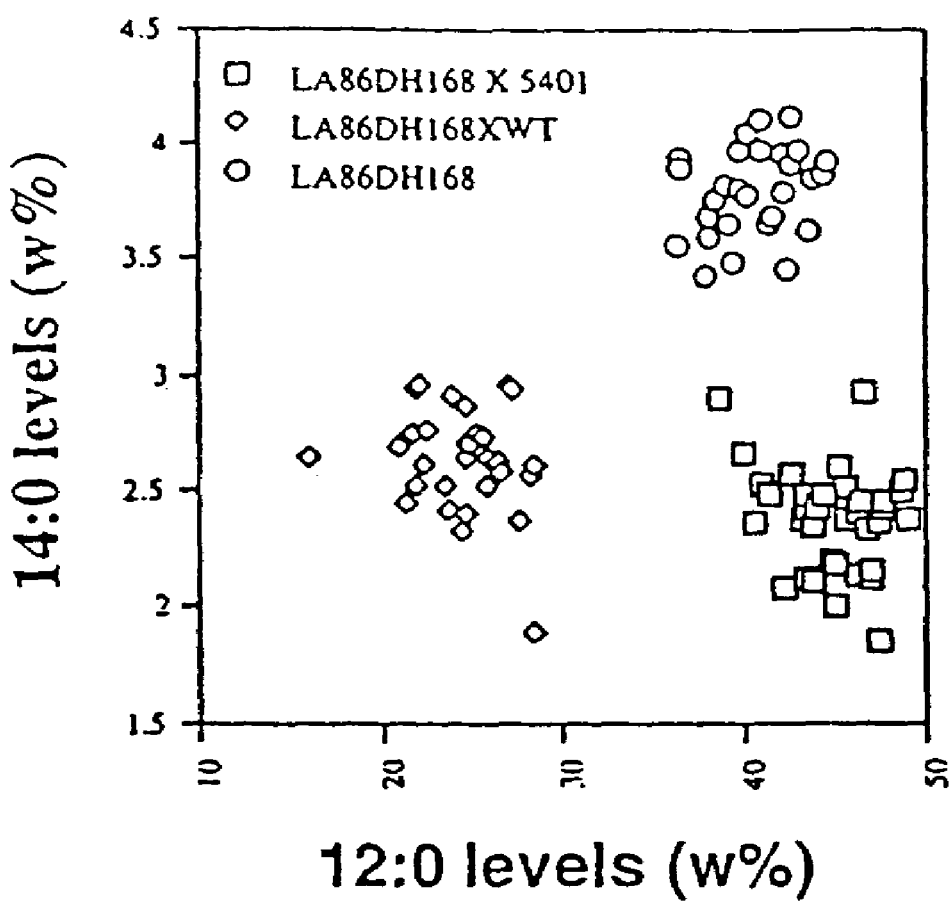
FIG. 20. Graph showing the relative proportions of C12:0 and C14:0 fatty acids in the seeds of transgenic plants containing Uc FatB1 (LA86DH186) and in plants resulting from crosses with wild type (X WT) and with lines expressing Ch KAS A-2-7.

However, crosses between LA86DH186 and the 5401-9 hemizygous line led to an accumulation of up to 57 mol % C12:0 in the seed oil of F1 progeny (FIGS. 19A, 19B, 19C). Interestingly, in crosses with LA86DH186× untransformed control line and LA86DH186×5401-9, levels of C14:0 in the seeds of the F1 progeny decreased to 50% of the levels obtained in homozygous LA86DH186 lines (FIG. 20). Furthermore, increases in the proportion of C12:0 fatty acid resulted in a substantial decline in the proportions of all the long-chain fatty acyl groups (C16:0, C18:0, C18:2, and C18:3). These results indicate that the ChKAS A-2-7 is an enzyme with substrate specificity ranging from C6:0 to C10:0-ACP, and that its over-expression ultimately reduces the longer chain acyl-ACP pools.

Figures 21A, 21B, 21C:
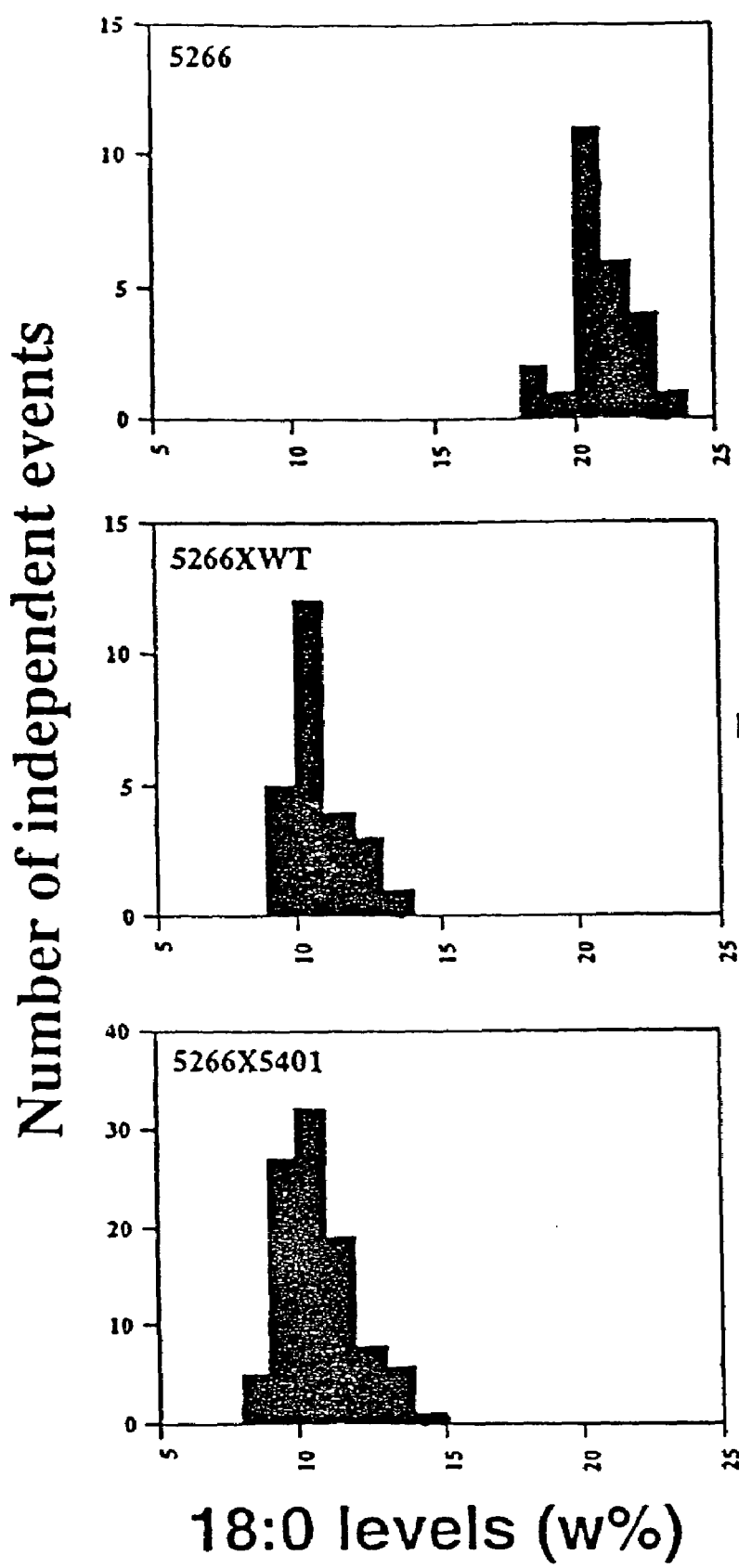
FIG. 21A. Graphs showing the % C18:0 in transgenic plants containing Garm FatB1 (5266) is provided.
FIG. 21B. Graph showing the % C18:0 in transgenic seeds resulting from cross of plants containing Garm FatB1 (5266) and wild type (X WT) is provided.
FIG. 21C. Graph showing the % C18:0 in transgenic seeds of plants resulting from cross of plants containing Garm FatB1 (5266) and lines expressing Ch KAS A-2-7 is provided.

Further evidence is obtained in support of the chain length specificity of the ChKAS A-2-7 in crosses of the 5401-9 line with a transgenic line (5266) expressing an 18:1/18:0 TE from *Garcinia mangostana* (GarmFatA1, U.S. patent application Ser. No. 08/440,845). Transgenic *Brassica* line 5266 has been shown to accumulate up to 24 mol % C18:0 in the seed oil of homozygous lines (FIGS. 21A, 21B, and 21C). However, in the seed oil of F1 progeny of crosses between 5266 and 5401-9 levels of C18:0 were reduced to approximately 12 mol %. Furthermore, levels of C16:0 generated from these crosses was similar to the levels obtained from the seed oil of nontransgenic control plants.

Example 5

In vitro Analysis of Plant KAS Enzymes

Seed extracts were prepared from developing seeds of nontransgenic controls or transgenic *Brassica* expressing chKAS A-2-7 as described in Slabaugh et al. (*Plant Journal*, 1998 in press) and Leonard et al. (Plant Journal, 1998, in press). In vitro fatty acid synthesis assays were performed as described by Post-Beittenmiller (*J. Biol. Chem.* (1991), 266:1858-1865). Extracts were concentrated by ammonium sulfate precipitation and desalting using P-6 columns (Bio-Rad, Hercules, Calif.). Reactions (65 µl) contained 0.1M Tris/HCl (pH 8.0), 1 mM dithiothreitol, 25 mM recombinant spinach ACP1, 1 mM NADH, 2 mM NADPH, 50 µM malonyl-CoA, 10 µM [1-$^{14}$C]acetyl-CoA (50 mCi/mmol), 1 mg/ml BSA, and 0.25 mg/ml seed protein. Selected seed extracts were preincubated with cerulenin at 23° C. for 10 min. Reaction products were separated on an 18% acrlamide gel containing 2.25M urea, electroblotted onto to nitrocellulose and quntitated by phosporimaging using Image QuaNT software (Molecular Dynamics, Sunnyvale, Calif.). Authentic acyl-ACPs were run in parallel, immunoblotted and finally detected by anti-ACP serum to confirm fatty acid chain lengths.

Figure 22:
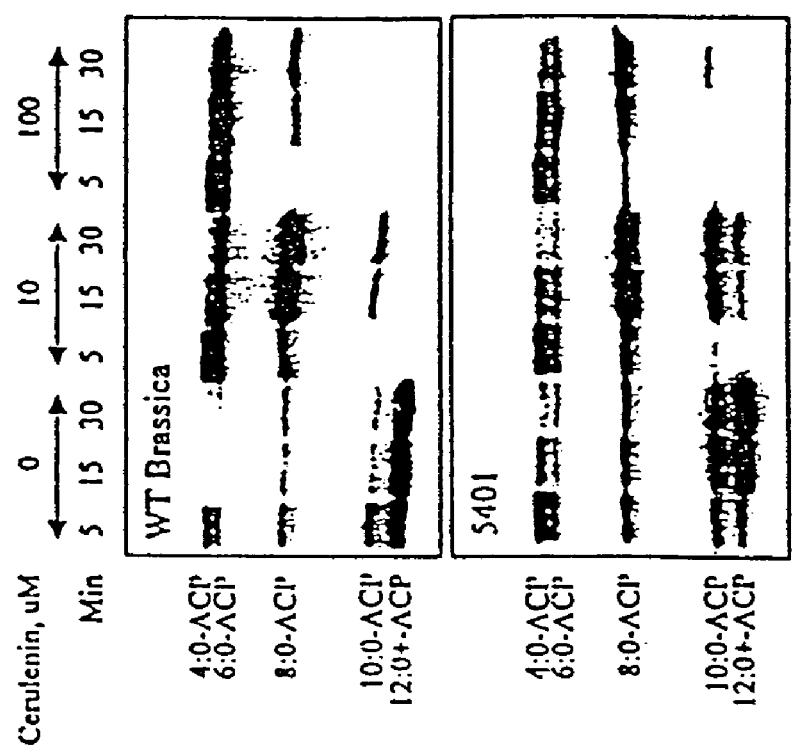
FIG. 22. The activity profile of Ch KAS A in protein extracts from transgenic plants containing Ch KAS A-2-7. Extracts were preptreated with the indicated concentrations of cerulenin.

The results (FIG. 22) indicate that the fatty acid synthesis capabilities of transgenic *Brasica* (5401-9) seed extracts was greater than that obtained from in the nontransgenic controls as measured by the relative abundance of C8:0- and C10:0-ACP at all time points tested. In addition, pretreatment of the extracts with cerulenin, markedly reduced the synthesis of longer chain fatty acids in both the transgenic and nontransgenic control seed extracts. However, the extension of the spinach-ACP was much less inhibited in the seed extracts from the transgenic lines than in the seed extracts of nontransgenic control *Brassica*.

These data further support that Ch KAS A-2-7 is a condensing enzyme active on medium chain acyl-ACPs, and that expression of this enzyme in plants results in enlarged substrate pools to be hydrolyzed by medium-chain specific thioesterases. Furthermore, these data suggest that chKAS A-2-7 also is a cerulenin-resistant condensing enzyme.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claim.

SEQUENCE LISTING

<160> NUMBER OF SEQ ID NOS: 17

<210> SEQ ID NO 1
<211> LENGTH: 1348
<212> TYPE: DNA
<213> ORGANISM: Cuphea hookeriana

<400> SEQUENCE: 1

```
agctccaccg cggtggcggc cgctctagaa ctagtggatc ccccgggctg caggaattcg      60
gcacgagccg atctcggtgc cgaccgcctc tccaagatcg acaaggagag agccggagtg     120
ctggtcggaa caggaatggg tggtctgact gtcttctctg acggggttca gtctcttatc     180
gagaagggtc accggaaaat caccccttc ttcatcccct atgccattac aaacatgggg     240
tctgccctgc tcgctatcga atttggtctc atgggcccaa actattcaat ttccactgca     300
tgtgccactt ccaactactg cttccatgct gccgctaatc atatccgccg tggtgaggct     360
gatcttatga ttgctggagg cactgaggcc gcaatcattc caattgggtt gggaggcttt     420
gtggcttgca gggctttgtc tcaaaggaac gatgacccgc agactgcctc taggccctgg     480
gataaagacc gtgatggttt tgtgatgggt gaaggtgctg gagtgttggt gatggagagc     540
ttggaacatg caatgagacg aggagcaccg attattgcag agtatttggg aggtgcaatc     600
aactgtgatg cttatcacat gactgatcca agggctgatg gtcttggtgt ctcttcttgc     660
attgagagta gccttgaaga tgctggcgtc tcacctgaag aggtcaatta cataaatgct     720
catgcgactt ctactctagc tggggatctc gccgagataa atgccatcaa gaaggttttc     780
aagaacacaa aggatatcaa aattaatgca actaagtcaa tgatcggaca ctgtcttgga     840
gcatctggag gtcttgaagc tatagcgact attaagggaa taaacaccgg ctggcttcat     900
cccagcatta atcaattcaa tcctgagcca tcggtggagt tcgacactgt tgccaacaag     960
aagcagcaac acgaagttaa cgttgcgatc tcgaattcat tcggatttgg aggccacaac    1020
tcagtcgtgg ctttctcggc tttcaagcca tgattaccca tttcacaagg tacttgtcat    1080
tgagaatacg gattatggac ttgcagagta atttccccat gtttgtcgga agagcatatt    1140
accacggttg tccgtcaaac ccatttagga tactgttcta tgtaataaaa ctaaggatta    1200
ttaatttccc tttaatcct gtctccagtt tgagcatgaa attatattta ttttatctta    1260
gaaaggtcaa ataagatttt gttttacctc tgtaaaactt ttgtttgtat tggaaaggaa    1320
```
gtgccgtctc aaaaaaaaaa aaaaaaa                        1348

<210> SEQ ID NO 2
<211> LENGTH: 350
<212> TYPE: PRT
<213> ORGANISM: Cuphea hookeriana

<400> SEQUENCE: 2

```
Ser Ser Thr Ala Val Ala Ala Leu Glu Leu Val Asp Pro Pro Gly
1               5                   10                  15

Cys Arg Asn Ser Ala Arg Ala Asp Leu Gly Ala Asp Arg Leu Ser Lys
            20                  25                  30

Ile Asp Lys Glu Arg Ala Gly Val Leu Val Gly Thr Gly Met Gly Gly
            35                  40                  45

Leu Thr Val Phe Ser Asp Gly Val Gln Ser Leu Ile Glu Lys Gly His
    50                  55                  60

Arg Lys Ile Thr Pro Phe Phe Ile Pro Tyr Ala Ile Thr Asn Met Gly
65                  70                  75                  80

Ser Ala Leu Leu Ala Ile Glu Phe Gly Leu Met Gly Pro Asn Tyr Ser
                85                  90                  95

Ile Ser Thr Ala Cys Ala Thr Ser Asn Tyr Cys Phe His Ala Ala Ala
                100                 105                 110

Asn His Ile Arg Arg Gly Glu Ala Asp Leu Met Ile Ala Gly Gly Thr
        115                 120                 125

Glu Ala Ala Ile Ile Pro Ile Gly Leu Gly Gly Phe Val Ala Cys Arg
    130                 135                 140

Ala Leu Ser Gln Arg Asn Asp Asp Pro Gln Thr Ala Ser Arg Pro Trp
145                 150                 155                 160

Asp Lys Asp Arg Asp Gly Phe Val Met Gly Glu Gly Ala Gly Val Leu
                165                 170                 175

Val Met Glu Ser Leu Glu His Ala Met Arg Arg Gly Ala Pro Ile Ile
                180                 185                 190

Ala Glu Tyr Leu Gly Gly Ala Ile Asn Cys Asp Ala Tyr His Met Thr
            195                 200                 205

Asp Pro Arg Ala Asp Gly Leu Gly Val Ser Ser Cys Ile Glu Ser Ser
    210                 215                 220

Leu Glu Asp Ala Gly Val Ser Pro Glu Glu Val Asn Tyr Ile Asn Ala
225                 230                 235                 240

His Ala Thr Ser Thr Leu Ala Gly Asp Leu Ala Glu Ile Asn Ala Ile
                245                 250                 255

Lys Lys Val Phe Lys Asn Thr Lys Asp Ile Lys Ile Asn Ala Thr Lys
                260                 265                 270

Ser Met Ile Gly His Cys Leu Gly Ala Ser Gly Gly Leu Glu Ala Ile
            275                 280                 285

Ala Thr Ile Lys Gly Ile Asn Thr Gly Trp Leu His Pro Ser Ile Asn
    290                 295                 300

Gln Phe Asn Pro Glu Pro Ser Val Glu Phe Asp Thr Val Ala Asn Lys
305                 310                 315                 320

Lys Gln Gln His Glu Val Asn Val Ala Ile Ser Asn Ser Phe Gly Phe
                325                 330                 335

Gly Gly His Asn Ser Val Val Ala Phe Ser Ala Phe Lys Pro
            340                 345                 350
```

<210> SEQ ID NO 3

-continued

```
<211> LENGTH: 1703
<212> TYPE: DNA
<213> ORGANISM: Cuphea hookeriana
<220> FEATURE:
<221> NAME/KEY: misc_feature
<222> LOCATION: (44)..(1499)
<223> OTHER INFORMATION: unsure at all n locations

<400> SEQUENCE: 3
aaattaaccc tcactaaagg gaacaaaagc tggagctcca ccgnggtggc ggccgctcta      60
gaactagtgg atcccccggg ctgcaggaat tcggcacgag ccggcatggg cctcgtctcc    120
gtattcggct ccgacgtcga ctcttattac gaaaagctcc tctccggcga gagcgggatc    180
agcttaatcg accgcttcga cgcttccaag ttccccacca ggttcggcgg ccagatccgg    240
ggattcaacg cgacgggata catcgacggg aagaacgaca ggaggctcga cgattgcctc    300
gctactgcat tgtcgccggg aagaaggctc tcgaaaattc cgatctcggc ggtgaaagcc    360
tctccaagat tgataaggag agagctggag tgctagttgg aactggtatg ggtggcctaa    420
ccgtcttctc tgacggggtt cagaatctca tcgagaaagg tcaccggaag atctccccgt    480
ttttcattcc ctatgccatt acaaacatgg ggtctgctct gcttgccatc gatttgggtc    540
tgatgggccc aaactattcg atttcaactg catgtgctac ttccaactac tgcttttatg    600
ccgctgccaa tcatatccgc cgaggcgagg ctgacctcat gattgctgga ggaactgagg    660
ctgcaatcat tccaattggg ttaggaggat tcgttgcctg cagggctttta tctcaaagga    720
atgatgaccc tcagactgcc tcaaggccgt gggataagga ccgtgatggt tttgtgatgg    780
gcgaaggggc tggagtattg gttatggaga gcttggaaca tgcaatgaaa cgaggagcgc    840
cgattattgc agaatatttg ggaggtgcag tcaattgtga tgcttatcat atgactgatc    900
caagggctga tgggcttggt gtctcctctt gcattgagag cagtctggaa gatgctgggg    960
tctcacctga agaggtcaat tacataaatg ctcatgcgac ttccactctt gctgggggatc   1020
ttgccgagat aaatgccatc aagaaggttt tcaagaacac caaggaaatc acaatcaatg   1080
caactaagtc gatgatcgga cactgtcttg gagcatcagg gggtcttgaa gccattgcga   1140
caattaaggg aataaccacc ggctggcttc atcccagcat aaaccaattc aatcccgagc   1200
catcagtgga attcgacaca gttgccaaca agaagcagca acatgaagtg aatgttgcta   1260
tctcaaattc attcggattc ggaggccaca actcagttgt agctttctca gccttcaagc   1320
catgattact cggttcaaat gcaaatttgt tgctgagaca gtgagcttca acttgcagag   1380
caattttttta catgccttgt cgtcggaaga gcgtaatacc gggatagttc cttgatagtt   1440
catttaggat gttttactgc aataatcgaa gattatttcc attctaatcc agtctccgnc   1500
gagtttgaga atctatctgt ttgtattaga agaacgagg caagattttg tttcatgttt    1560
gtgtttgtat tacttctttt ttgccttgt caatggcatt taagataagc ttataaaaaa    1620
aaaaaaaaaa aaaaaactc gagggggggc ccggtaccca attcgcccta tagtgagtcg   1680
tatgacaatt cactgtccgt cgg                                            1703

<210> SEQ ID NO 4
<211> LENGTH: 441
<212> TYPE: PRT
<213> ORGANISM: Cuphea hookeriana
<220> FEATURE:
<221> NAME/KEY: Unsure
<222> LOCATION: (15)..(15)
<223> OTHER INFORMATION: X = Any Amino Acid
<220> FEATURE:
<221> NAME/KEY: misc_feature
```

```
<222> LOCATION: (15)..(15)
<223> OTHER INFORMATION: X = Any Amino Acid

<400> SEQUENCE: 4
```

| | | | | | | | | | | | | | | |
|---|---|---|---|---|---|---|---|---|---|---|---|---|---|---|
| Lys | Leu | Thr | Leu | Thr | Lys | Gly | Asn | Lys | Ser | Trp | Ser | Ser | Thr | Xaa | Val |
| 1 | | | | 5 | | | | | 10 | | | | | 15 |

Ala Ala Ala Leu Glu Leu Val Asp Pro Pro Gly Cys Arg Asn Ser Ala
            20                  25                  30

Arg Ala Gly Met Gly Leu Val Ser Val Phe Gly Ser Asp Val Asp Ser
        35                  40                  45

Tyr Tyr Glu Lys Leu Leu Ser Gly Ser Gly Ile Ser Leu Ile Asp
50                  55                  60

Arg Phe Asp Ala Ser Lys Phe Pro Thr Arg Phe Gly Gln Ile Arg
65                  70                  75                  80

Gly Phe Asn Ala Thr Gly Tyr Ile Asp Gly Lys Asn Asp Arg Arg Leu
                85                  90                  95

Asp Asp Cys Leu Arg Tyr Cys Ile Val Ala Gly Lys Lys Ala Leu Glu
            100                 105                 110

Asn Ser Asp Leu Gly Gly Glu Ser Leu Ser Lys Ile Asp Lys Glu Arg
            115                 120                 125

Ala Gly Val Leu Val Gly Thr Gly Met Gly Gly Leu Thr Val Phe Ser
            130                 135                 140

Asp Gly Val Gln Asn Leu Ile Glu Lys Gly His Arg Lys Ile Ser Pro
145                 150                 155                 160

Phe Phe Ile Pro Tyr Ala Ile Thr Asn Met Gly Ser Ala Leu Leu Ala
                165                 170                 175

Ile Asp Leu Gly Leu Met Gly Pro Asn Tyr Ser Ile Ser Thr Ala Cys
            180                 185                 190

Ala Thr Ser Asn Tyr Cys Phe Tyr Ala Ala Ala Asn His Ile Arg Arg
            195                 200                 205

Gly Glu Ala Asp Leu Met Ile Ala Gly Gly Thr Glu Ala Ala Ile Ile
            210                 215                 220

Pro Ile Gly Leu Gly Gly Phe Val Ala Cys Arg Ala Leu Ser Gln Arg
225                 230                 235                 240

Asn Asp Asp Pro Gln Thr Ala Ser Arg Pro Trp Asp Lys Asp Arg Asp
                245                 250                 255

Gly Phe Val Met Gly Glu Gly Ala Gly Val Leu Val Met Glu Ser Leu
            260                 265                 270

Glu His Ala Met Lys Arg Gly Ala Pro Ile Ile Ala Glu Tyr Leu Gly
            275                 280                 285

Gly Ala Val Asn Cys Asp Ala Tyr His Met Thr Asp Pro Arg Ala Asp
            290                 295                 300

Gly Leu Gly Val Ser Ser Cys Ile Glu Ser Ser Leu Glu Asp Ala Gly
305                 310                 315                 320

Val Ser Pro Glu Glu Val Asn Tyr Ile Asn Ala His Ala Thr Ser Thr
                325                 330                 335

Leu Ala Gly Asp Leu Ala Glu Ile Asn Ala Ile Lys Lys Val Phe Lys
            340                 345                 350

Asn Thr Lys Glu Ile Thr Ile Asn Ala Thr Lys Ser Met Ile Gly His
            355                 360                 365

Cys Leu Gly Ala Ser Gly Gly Leu Glu Ala Ile Ala Thr Ile Lys Gly
            370                 375                 380

Ile Thr Thr Gly Trp Leu His Pro Ser Ile Asn Gln Phe Asn Pro Glu
385                 390                 395                 400

```
Pro Ser Val Glu Phe Asp Thr Val Ala Asn Lys Lys Gln Gln His Glu
            405                 410                 415
Val Asn Val Ala Ile Ser Asn Ser Phe Gly Phe Gly Gly His Asn Ser
            420                 425                 430
Val Val Ala Phe Ser Ala Phe Lys Pro
            435                 440

<210> SEQ ID NO 5
<211> LENGTH: 2046
<212> TYPE: DNA
<213> ORGANISM: Cuphea hookeriana

<400> SEQUENCE: 5
actaaaggga acaaaagctg agctccacc gcggtggcgg ccgctctaga actagtggat    60
ccccccgggct gcaggaattc ggcacgagtt ttcttacttg ggtcggctca gctcaggtgt   120
tccaatggcg accgcttctt gcatggttgc gtcccctttc tgtacgtggc tcgtagctgc   180
atgcatgccc acttcatccg acaacgaccc acgttcccct tcccacaagc ggctccgcct   240
ctcccgtcgc cggaggactc tctcctccca ttgctccctc cgcggatcca ccttccaatg   300
cctcgatcct tgcaaccagc aacgcttcct cggggataac ggattcgctt ccctcttcgg   360
atccaagcct cttcgttcaa atcgcggcca cctgaggctc ggccgcactt cccattccgg   420
ggaggtcatg gctgtggcta tgcaacctgc acaggaagtc tccacaaata gaaacctgc    480
taccaagcaa aggcgagtag ttgtgacagg tatgggcgtg gtgactcctc taggccatga   540
ccccgatgtt tactacaaca atctcctaga cggaataagt ggcataagtg agatagagaa   600
cttcgactgc tctcagtttc ccacgagaat tgccggagag atcaagtctt tttccacaga   660
tggctgggtg gccccaaagt tctccgagag gatggacaag ttcatgcttt acatgctgac   720
tgcaggcaag aaagcattag cagatggtgg aatcactgaa gatgcgatga agagctcaa    780
taaaagaaag tgtggagttc tcattggctc cggattgggc ggtatgaagg tattcagcga   840
ttccattgaa gctctgagga cttcatataa gaagatcagt cccttttgtg tacctttttc   900
taccacaaat atgggatccg ctattcttgc aatggacttg gatggatgg gccctaacta   960
ttcgatatca actgcctgtg caacaagtaa cttctgtata ctgaatgctg cgaaccacat  1020
aatcaaaggc gaagcagaca tgatgctttg tggtggctcg gatgcggccg ttttacctgt  1080
tggtttggga ggtttcgtag catgccgagc tttgtcacag aggaataatg accctaccaa  1140
agcttcgaga ccatgggaca gtaatcgtga tggatttgtg atgggagaag gagctggagt  1200
tttacttctt gaggagttag agcatgcaaa gaaaagaggt gcaaccattt atgcggaatt  1260
tctaggtggg agtttcactt gcgacgccta ccacatgacc gagcctcacc ctgaaggagc  1320
tggtgtgatc ctctgcatag agaaggcctt ggctcagtcc ggagtctcga gggaagacgt  1380
aaattacata aatgcgcatg caacttccac tcctgctgga gatatcaagg aataccaagc  1440
tctcgcccac tgtttcggcc aaaacagtga gctgagagtg aattccacca atcgatgat   1500
cggtcacctt cttggaggag ctggtggcgt agaagcagtt gcagtagttc aggcaataag  1560
gacaggatgg atccatccaa atattaattt ggaagacccg gacgaaggcg tggatgcaaa  1620
actgctcgtc ggccctaaga aggagaaact gaaggtcaag gtcggtttgt ccaattcatt  1680
tgggttcggc ggccataact catccatact atttgccccc tgcaactaga aaagagtctg  1740
tggaagccga gagtctttga gaactcatgc acgttagtag cttcttatgc ctctgaaacc  1800
gagatagacc ggctactcga ggggatgcca agatactcc ttgccggtat tggtgttaag   1860
```

-continued

```
agatcactgc ttgtcccttt tatttctc ttctttgag agctttaacc gaggtagtcg    1920 tatttcgag cttttcgaat acatgttcgt tatcggatca atgtgtttct tctaagatca    1980
tttgtaatgc atattttgaa aaaccacatc tcagtatgca aataaaaaa aaaaaaaaa    2040 aaaaaa                                                               2046
```

<210> SEQ ID NO 6
<211> LENGTH: 534
<212> TYPE: PRT
<213> ORGANISM: Cuphea hookeriana

<400> SEQUENCE: 6

```
Met Ala Thr Ala Ser Cys Met Val Ala Ser Pro Phe Cys Thr Trp Leu
 1               5                  10                  15

Val Ala Ala Cys Met Pro Thr Ser Ser Asp Asn Asp Pro Arg Ser Leu
            20                  25                  30

Ser His Lys Arg Leu Arg Leu Ser Arg Arg Arg Thr Leu Ser Ser
        35                  40                  45

His Cys Ser Leu Arg Gly Ser Thr Phe Gln Cys Leu Asp Pro Cys Asn
    50                  55                  60

Gln Gln Arg Phe Leu Gly Asp Asn Gly Phe Ala Ser Leu Phe Gly Ser
65                  70                  75                  80

Lys Pro Leu Arg Ser Asn Arg Gly His Leu Arg Leu Gly Arg Thr Ser
                85                  90                  95

His Ser Gly Glu Val Met Ala Val Ala Met Gln Pro Ala Gln Glu Val
            100                 105                 110

Ser Thr Asn Lys Lys Pro Ala Thr Lys Gln Arg Arg Val Val Val Thr
        115                 120                 125

Gly Met Gly Val Val Thr Pro Leu Gly His Asp Pro Asp Val Tyr Tyr
130                 135                 140

Asn Asn Leu Leu Asp Gly Ile Ser Gly Ile Ser Glu Ile Glu Asn Phe
145                 150                 155                 160

Asp Cys Ser Gln Phe Pro Thr Arg Ile Ala Gly Glu Ile Lys Ser Phe
                165                 170                 175

Ser Thr Asp Gly Trp Val Ala Pro Lys Phe Ser Glu Arg Met Asp Lys
            180                 185                 190

Phe Met Leu Tyr Met Leu Thr Ala Gly Lys Lys Ala Leu Ala Asp Gly
        195                 200                 205

Gly Ile Thr Glu Asp Ala Met Lys Glu Leu Asn Lys Arg Lys Cys Gly
    210                 215                 220

Val Leu Ile Gly Ser Gly Leu Gly Gly Met Lys Val Phe Ser Asp Ser
225                 230                 235                 240

Ile Glu Ala Leu Arg Thr Ser Tyr Lys Lys Ile Ser Pro Phe Cys Val
                245                 250                 255

Pro Phe Ser Thr Thr Asn Met Gly Ser Ala Ile Leu Ala Met Asp Leu
            260                 265                 270

Gly Trp Met Gly Pro Asn Tyr Ser Ile Ser Thr Ala Cys Ala Thr Ser
        275                 280                 285

Asn Phe Cys Ile Leu Asn Ala Ala Asn His Ile Ile Lys Gly Glu Ala
    290                 295                 300

Asp Met Met Leu Cys Gly Gly Ser Asp Ala Ala Val Leu Pro Val Gly
305                 310                 315                 320

Leu Gly Gly Phe Val Ala Cys Arg Ala Leu Ser Gln Arg Asn Asn Asp
                325                 330                 335
```

```
Pro Thr Lys Ala Ser Arg Pro Trp Asp Ser Asn Arg Asp Gly Phe Val
        340                 345                 350

Met Gly Glu Gly Ala Gly Val Leu Leu Leu Glu Glu Leu Glu His Ala
        355                 360                 365

Lys Lys Arg Gly Ala Thr Ile Tyr Ala Glu Phe Leu Gly Gly Ser Phe
        370                 375                 380

Thr Cys Asp Ala Tyr His Met Thr Glu Pro His Pro Glu Gly Ala Gly
385                 390                 395                 400

Val Ile Leu Cys Ile Glu Lys Ala Leu Ala Gln Ser Gly Val Ser Arg
                405                 410                 415

Glu Asp Val Asn Tyr Ile Asn Ala His Ala Thr Ser Thr Pro Ala Gly
                420                 425                 430

Asp Ile Lys Glu Tyr Gln Ala Leu Ala His Cys Phe Gly Gln Asn Ser
                435                 440                 445

Glu Leu Arg Val Asn Ser Thr Lys Ser Met Ile Gly His Leu Leu Gly
        450                 455                 460

Gly Ala Gly Gly Val Glu Ala Val Ala Val Val Gln Ala Ile Arg Thr
465                 470                 475                 480

Gly Trp Ile His Pro Asn Ile Asn Leu Glu Asp Pro Asp Glu Gly Val
                485                 490                 495

Asp Ala Lys Leu Leu Val Gly Pro Lys Lys Glu Lys Leu Lys Val Lys
        500                 505                 510

Val Gly Leu Ser Asn Ser Phe Gly Phe Gly Gly His Asn Ser Ser Ile
        515                 520                 525

Leu Phe Ala Pro Cys Asn
    530

<210> SEQ ID NO 7
<211> LENGTH: 1921
<212> TYPE: DNA
<213> ORGANISM: Cuphea hookeriana

<400> SEQUENCE: 7
cggcacgagg tcacctctta cctcgcctgc ttcgagccct gccatgacta ctacacctcc     60
gcatccttgt tcggatccag gcccatccgc accacccgca ggcaccggag gctcaatcga    120
gcttcccctt ccggggaggc aatggctgtg gctctgcaac ctgcacagga agttaccaca    180
aagaagaagc caagtatcaa acagcggcga gtagttgtga ctggaatggg tgtggtgact    240
cctctaggcc atgaccctga tgttttctac aataatctgc ttgatggaac gagtggcata    300
agtgagatag gacctttga ttgtgctcaa tttcctacga gaattgctgg agagatcaag    360
tctttctcca cagatggttg ggtggccccg aagctctcca gaggatgga caagttcatg    420 ctttacatgc tgactgccgg caagaaagca ttaacaaatg gtggaatcac gaagatgtg    480 atgaaagagc tagataaaag aaaatgcgga gttctcattg ctcagcaat gggtggaatg    540 aaggtattca atgatgccat tgaagcccta aggatttcat ataagaagat gaatcccttt    600
tgtgtacctt tcgctaccac aaatatggga tcagctatgc ttgcaatgga cttgggatgg    660
atgggcccca actactcgat atctactgct tgtgcaacga gtaacttttg tatcctgaat    720
gctgcgaacc acataatcag aggcgaagca gatgtgatgc tttgcggggg ctcagatgcg    780
gtaatcatac ctattggtat gggaggtttt gttgcatgcc gagctttgtc acagagaaat    840
gccgacccta ctaaagcttc aagaccatgg acagtaatc gtgatggatt tgttatgggg    900
gaaggagctg gagtgctact actagaggag ttagagcatg caaagaaaag aggtgcgact    960
```

```
atttacgcag aatttctagg tggaagtttc acttgcgatg cctaccacat gaccgagcct   1020
caccctgatg gagctggagt gattctctgc atagagaagg ctttggctca gtcaggagtc   1080 tctaggaag  acgtaaatta cataaatgca catgccacat ccactccagc tggagatatc    1140
aaagagtacc aagctcttat ccactgtttc ggccaaaaca acgagttaaa agtgaattct   1200
accaaatcaa tgattggtca ccttctcgga gcagccggtg gtgtggaagc agtttcagta   1260
gttcaggcaa taaggactgg gtggatccat ccgaatatta atttggaaaa cccagatgaa   1320
ggcgtggata ccaaattgct cgtgggccct aagaaggaga gactgaacat taaggtcggt   1380
ttgtctaatt cattcgggtt tggtgggcac aactcgtcca tactcttcgc cccttacaac   1440
tagggcgttt catgtgtgga attctactca atctatcaaa gctgaagttt tgaggactcc   1500
agcatgttgg tagctcctta cgtctctaga catgcccatg agttttgtgt cgggagctgt   1560
agtcggaacc atgacggatt gagtactcat ggcgacacag gatatactcc ttgctagaat   1620
tgttagagca ctattcatta tcccattttt tttctgaaat ctccctcctt acggtagttg   1680
tactttcgag cgtttcatcg agtcagtgaa gaagagaaca aagctaactc gggcacgtag   1740
taaccatttg cccttttgttt tgctctctat tttatcgccg ttttgtgggt taaaatttgt   1800
aaaactagac gactggtttg ttttctcttg atcattggag atgtatggcc atatttgcct   1860
ttcattgatg ataaaaaaaa aaaaaaaaa aaaaaaaaaa aaaaaaaaaa aaaaaaaaa     1920 a                                                                    1921

<210> SEQ ID NO 8
<211> LENGTH: 420
<212> TYPE: PRT
<213> ORGANISM: Cuphea hookeriana

<400> SEQUENCE: 8

Lys Lys Lys Pro Ser Ile Lys Gln Arg Arg Val Val Thr Gly Met
1               5                   10                  15

Gly Val Val Thr Pro Leu Gly His Asp Pro Asp Val Phe Tyr Asn Asn
                20                  25                  30

Leu Leu Asp Gly Thr Ser Gly Ile Ser Glu Ile Glu Thr Phe Asp Cys
        35                  40                  45

Ala Gln Phe Pro Thr Arg Ile Ala Gly Glu Ile Lys Ser Phe Ser Thr
    50                  55                  60

Asp Gly Trp Val Ala Pro Lys Leu Ser Lys Arg Met Asp Lys Phe Met
65                  70                  75                  80

Leu Tyr Met Leu Thr Ala Gly Lys Lys Ala Leu Thr Asn Gly Gly Ile
                85                  90                  95

Thr Glu Asp Val Met Lys Glu Leu Asp Lys Arg Lys Cys Gly Val Leu
                100                 105                 110

Ile Gly Ser Ala Met Gly Gly Met Lys Val Phe Asn Asp Ala Ile Glu
        115                 120                 125

Ala Leu Arg Ile Ser Tyr Lys Lys Met Asn Pro Phe Cys Val Pro Phe
    130                 135                 140

Ala Thr Thr Asn Met Gly Ser Ala Met Leu Ala Met Asp Leu Gly Trp
145                 150                 155                 160

Met Gly Pro Asn Tyr Ser Ile Ser Thr Ala Cys Ala Thr Ser Asn Phe
                165                 170                 175

Cys Ile Leu Asn Ala Ala Asn His Ile Ile Arg Gly Glu Ala Asp Val
                180                 185                 190
```

-continued

```
Met Leu Cys Gly Gly Ser Asp Ala Val Ile Pro Ile Gly Met Gly
            195                 200                 205
Gly Phe Val Ala Cys Arg Ala Leu Ser Gln Arg Asn Ala Asp Pro Thr
        210                 215                 220
Lys Ala Ser Arg Pro Trp Asp Ser Asn Arg Asp Gly Phe Val Met Gly
225                 230                 235                 240
Glu Gly Ala Gly Val Leu Leu Leu Glu Glu Leu Glu His Ala Lys Lys
                245                 250                 255
Arg Gly Ala Thr Ile Tyr Ala Glu Phe Leu Gly Gly Ser Phe Thr Cys
            260                 265                 270
Asp Ala Tyr His Met Thr Glu Pro His Pro Asp Gly Ala Gly Val Ile
        275                 280                 285
Leu Cys Ile Glu Lys Ala Leu Ala Gln Ser Gly Val Ser Arg Glu Asp
290                 295                 300
Val Asn Tyr Ile Asn Ala His Ala Thr Ser Thr Pro Ala Gly Asp Ile
305                 310                 315                 320
Lys Glu Tyr Gln Ala Leu Ile His Cys Phe Gly Gln Asn Asn Glu Leu
                325                 330                 335
Lys Val Asn Ser Thr Lys Ser Met Ile Gly His Leu Leu Gly Ala Ala
            340                 345                 350
Gly Gly Val Glu Ala Val Ser Val Val Gln Ala Ile Arg Thr Gly Trp
        355                 360                 365
Ile His Pro Asn Ile Asn Leu Glu Asn Pro Asp Glu Gly Val Asp Thr
    370                 375                 380
Lys Leu Leu Val Gly Pro Lys Lys Glu Arg Leu Asn Ile Lys Val Gly
385                 390                 395                 400
Leu Ser Asn Ser Phe Gly Phe Gly Gly His Asn Ser Ser Ile Leu Phe
                405                 410                 415
Ala Pro Tyr Asn
            420
```

<210> SEQ ID NO 9
<211> LENGTH: 1713
<212> TYPE: DNA
<213> ORGANISM: Cuphea pulcherrima

<400> SEQUENCE: 9

```
ctggtacgcc tgcaggtacc ggtccggaat cccgggtcg acccacgcgt ccgtcttccc      60
actccgatcg ttcttcttcc accgcatctc ttctcttctc ttggcttctc cgccatcctc    120
cgccgccatg cattccctcc agtcaccctc ccttcgggcc tcccgctcg accccttccg     180
ccccaaatca tccaccgtcc gccccctcca ccgagcatca attcccaacg tccgggccgc    240
ttcccccacc gtctccgctc ccaagcgcga accgaccccc aagaagcgcg tcgtgatcac    300
cggaatgggc cttgtctccg ttttcggctc cgacgtcgat gcgtactacg acaagctcct    360
gtcaggcgag agcgggatcg gcccaatcga ccgcttcgac gcctccaagt tccccaccag    420
gttcggcggc cagattcgtg gcttcaactc catgggatac attgacggca aaaacgacag    480
gcggcttgat gattgccttc gctactgcat tgtcgccggg aagaagtctc ttgaggacgc    540
cgatctcggt gccgaccgcc tctccaagat cgacaaggag agagccggag tgctggttgg    600
gacaggaatg ggtggtctga ctgtcttctc tgacggggtt caatctctta cgagaaggg     660
tcaccggaaa atcaccccct tcttcatccc ctatgccatt acaaacatgg ggtctgccct    720
gctcgctatt gaactcggtc tgatgggccc aaactattca atttccactg catgtgccac    780
```

```
ttccaactac tgcttccatg ctgctgctaa tcatatccgc cgtggtgagg ctgatcttat      840
gattgctgga ggcactgagg ccgcaatcat tccaattggg ttgggaggct ttgtggcttg      900
cagggctctg tctcaaagga acgatgaccc tcagactgcc tctaggccct gggataaaga      960
ccgtgatggt tttgtgatgg gtgaaggtgc tggagtgttg gtgctggaga gcttggaaca     1020
tgcaatgaaa cgaggagcac ctattattgc agagtatttg ggaggtgcaa tcaactgtga     1080
tgcttatcac atgactgacc caaggctga tggtctcggt gtctcctctt gcattgagag      1140
tagccttgaa gatgctggcg tctcacctga agaggtcaat tacataaatg ctcatgcgac     1200
ttctactcta gctgggatc tcgccgagat aaatgccatc aagaaggttt tcaagaacac      1260
aaaggatatc aaaattaatg caactaagtc aatgatcgga cactgtcttg agcctctgg      1320 aggtcttgaa gctatagcga ctattaaggg aataaacacc ggctggcttc atcccagcat     1380
taatcaattc aatcctgagc catccgtgga gttcgacact gttgccaaca agaagcagca     1440
acacgaagtt aatgttgcga tctcgaattc atttggattc ggaggccaca actcagtcgt     1500
ggctttctcg gctttcaagc catgattacc catttcacaa ggcacttgtc attgagagta     1560
cggttgttcg tcaaacccat ttaggatact gttctatgta aaaaaaagta aggattatca     1620
ctttcccttc taatcctgtc tccagtttga gaatgaaatt atatttattt taaaaaaaaa     1680
aaaaaagggc ggccgctcta gaggatccaa gct                                  1713
```

<210> SEQ ID NO 10
<211> LENGTH: 465
<212> TYPE: PRT
<213> ORGANISM: Cuphea pulcherrima

<400> SEQUENCE: 10

```
Met His Ser Leu Gln Ser Pro Ser Leu Arg Ala Ser Pro Leu Asp Pro
1               5                   10                  15

Phe Arg Pro Lys Ser Ser Thr Val Arg Pro Leu His Arg Ala Ser Ile
            20                  25                  30

Pro Asn Val Arg Ala Ala Ser Pro Thr Val Ser Ala Pro Lys Arg Glu
        35                  40                  45

Thr Asp Pro Lys Lys Arg Val Val Ile Thr Gly Met Gly Leu Val Ser
    50                  55                  60

Val Phe Gly Ser Asp Val Asp Ala Tyr Tyr Asp Lys Leu Leu Ser Gly
65                  70                  75                  80

Glu Ser Gly Ile Gly Pro Ile Asp Arg Phe Asp Ala Ser Lys Phe Pro
                85                  90                  95

Thr Arg Phe Gly Gly Gln Ile Arg Gly Phe Asn Ser Met Gly Tyr Ile
            100                 105                 110

Asp Gly Lys Asn Asp Arg Arg Leu Asp Asp Cys Leu Arg Tyr Cys Ile
        115                 120                 125

Val Ala Gly Lys Lys Ser Leu Glu Asp Ala Asp Leu Gly Ala Asp Arg
    130                 135                 140

Leu Ser Lys Ile Asp Lys Glu Arg Ala Gly Val Leu Val Gly Thr Gly
145                 150                 155                 160

Met Gly Gly Leu Thr Val Phe Ser Asp Gly Val Gln Ser Leu Ile Glu
                165                 170                 175

Lys Gly His Arg Lys Ile Thr Pro Phe Phe Ile Pro Tyr Ala Ile Thr
            180                 185                 190

Asn Met Gly Ser Ala Leu Leu Ala Ile Glu Leu Gly Leu Met Gly Pro
        195                 200                 205
```

```
Asn Tyr Ser Ile Ser Thr Ala Cys Ala Thr Ser Asn Tyr Cys Phe His
    210                 215                 220

Ala Ala Ala Asn His Ile Arg Arg Gly Glu Ala Asp Leu Met Ile Ala
225                 230                 235                 240

Gly Gly Thr Glu Ala Ala Ile Ile Pro Ile Gly Leu Gly Gly Phe Val
                245                 250                 255

Ala Cys Arg Ala Leu Ser Gln Arg Asn Asp Asp Pro Gln Thr Ala Ser
            260                 265                 270

Arg Pro Trp Asp Lys Asp Arg Asp Gly Phe Val Met Gly Glu Gly Ala
        275                 280                 285

Gly Val Leu Val Leu Glu Ser Leu Glu His Ala Met Lys Arg Gly Ala
    290                 295                 300

Pro Ile Ile Ala Glu Tyr Leu Gly Gly Ala Ile Asn Cys Asp Ala Tyr
305                 310                 315                 320

His Met Thr Asp Pro Arg Ala Asp Gly Leu Gly Val Ser Ser Cys Ile
                325                 330                 335

Glu Ser Ser Leu Glu Asp Ala Gly Val Ser Pro Glu Val Asn Tyr
            340                 345                 350

Ile Asn Ala His Ala Thr Ser Thr Leu Ala Gly Asp Leu Ala Glu Ile
            355                 360                 365

Asn Ala Ile Lys Lys Val Phe Lys Asn Thr Lys Asp Ile Lys Ile Asn
370                 375                 380

Ala Thr Lys Ser Met Ile Gly His Cys Leu Gly Ala Ser Gly Gly Leu
385                 390                 395                 400

Glu Ala Ile Ala Thr Ile Lys Gly Ile Asn Thr Gly Trp Leu His Pro
                405                 410                 415

Ser Ile Asn Gln Phe Asn Pro Glu Pro Ser Val Glu Phe Asp Thr Val
            420                 425                 430

Ala Asn Lys Lys Gln Gln His Glu Val Asn Val Ala Ile Ser Asn Ser
        435                 440                 445

Phe Gly Phe Gly Gly His Asn Ser Val Val Ala Phe Ser Ala Phe Lys
    450                 455                 460

Pro
465

<210> SEQ ID NO 11
<211> LENGTH: 1802
<212> TYPE: DNA
<213> ORGANISM: Cuphea pulcherrima

<400> SEQUENCE: 11
ggtcgaccca cgcgtccggg ctttccgacc acatttcatt tcttgcctcg ttatctccgc    60
cgctcctccg ccgtcgttcg ccgccgccgc catgcaatcc ctccactccc cttccctccg   120
cccctcccct ctcgagccct tccgcctcaa ttcccctcc tccgccgccg ctctccgccc    180
cctccgtcgc gccagcctcc ccgtcatccg tgctgccacc gcctccgccc ccaagcgcga   240
gtccgacccc aagaagcggg tcgtcatcac cggcatgggc ctcgtctccg tcttcggctc   300
cgacgtcgac gcctactacg acaagctgct ctccggcgag agcggcatca gcctaatcga   360
ccgcttcgac gcttccaaat tccccaccag gttcgccggc cagatccgtg gcttcaacgc   420
gacgggctac atcgacggca agaacgaccg gcggctcgac gattgcctcc gctactgcat   480
tgtcgccggc aagaaggctc tcgaagacgc cgatctcgcc ggccaatccc tctccaagat   540
tgataaggag agggccggag tgctagttgg aaccggtatg ggtggcctaa ctgtcttctc   600
```

```
tgacggggtt cagaatctca tcgagaaagg tcaccggaag atctccccgt ttttcattcc      660
atatgccatt acaaacatgg ggtctgcgct gcttgccatc gatttgggtc tgatgggccc      720
aaactattcg atttcaactg catgtgctac ttccaactac tgcttttatg ctgccgccaa      780
tcatatccgc cgaggtgagg ctgacctgat gattgctgga ggaactgagg ctgcggtcat      840
tccaattggt ttaggaggat tcgttgcctg cagggcttta tctcaaagga atgatgatcc      900
tcagactgcc tcaaggccgt gggataagga ccgtgatggc tttgtgatgg gtgaaggggc      960
tggagtattg gttatggaga gcttggagca tgcaatgaaa cggggagcgc cgattattgc     1020
agaatatttg ggaggtgcag tcaactgtga tgcttatcat atgactgatc caagggctga     1080
tgggcttggt gtctcctcgt gcattgagag cagtctcgaa gatgccgggg tctcacctga     1140
agaggtcaat tacataaatg ctcatgcgac ttctactctt gctggggatc ttgccgagat     1200
aaatgccatt aagaaagttt tcaagaacac caaggaaatc aaaatcaatg caactaagtc     1260
aatgatcgga cactgtcttg gagcatcagg aggtcttgaa gccatcgcaa ccattaaggg     1320
aataaccacc ggctggcttc atcccagcat taatcaattt aatcccgagc catcggtgga     1380
cttcaacact gttgccaaca aaagcagca acatgaagtg aacgtcgcta tctcgaattc     1440
ttttggattt ggagggcaca actcggttgt ggcattctca gctttcaagc catgaattct     1500
acttggttca aaatgcacac cagttgctga gatagggctt caacttgcag agcaattttt     1560
taaatgcctt gtcggaagag cgtaataccg gaataggtcg gtccttttga tagttcctcga    1620
agccatttag gatgatgttt tactgtaata atcgaagatg attcccattt taaatctagt     1680
ctctgattta tgtattagaa agaccaatga agattttgt gtcatgttg tgttgtcaat       1740
gttatttaag ataaagcaaa aaaaaaaaaa aagggcggcc gctctagagg atccagctta    1800
ct                                                                    1802
```

<210> SEQ ID NO 12
<211> LENGTH: 467
<212> TYPE: PRT
<213> ORGANISM: Cuphea pulcherrima

<400> SEQUENCE: 12

```
Met Gln Ser Leu His Ser Pro Ser Leu Arg Pro Ser Pro Leu Glu Pro
1               5                   10                  15

Phe Arg Leu Asn Ser Pro Ser Ser Ala Ala Ala Leu Arg Pro Leu Arg
            20                  25                  30

Arg Ala Ser Leu Pro Val Ile Arg Ala Ala Thr Ala Ser Ala Pro Lys
        35                  40                  45

Arg Glu Ser Asp Pro Lys Lys Arg Val Val Ile Thr Gly Met Gly Leu
    50                  55                  60

Val Ser Val Phe Gly Ser Asp Val Asp Ala Tyr Tyr Asp Lys Leu Leu
65                  70                  75                  80

Ser Gly Glu Ser Gly Ile Ser Leu Ile Asp Arg Phe Asp Ala Ser Lys
                85                  90                  95

Phe Pro Thr Arg Phe Ala Gly Gln Ile Arg Gly Phe Asn Ala Thr Gly
            100                 105                 110

Tyr Ile Asp Gly Lys Asn Asp Arg Arg Leu Asp Asp Cys Leu Arg Tyr
        115                 120                 125

Cys Ile Val Ala Gly Lys Lys Ala Leu Glu Asp Ala Asp Leu Ala Gly
    130                 135                 140

Gln Ser Leu Ser Lys Ile Asp Lys Glu Arg Ala Gly Val Leu Val Gly
145                 150                 155                 160
```

```
Thr Gly Met Gly Gly Leu Thr Val Phe Ser Asp Gly Val Gln Asn Leu
                165                 170                 175
Ile Glu Lys Gly His Arg Lys Ile Ser Pro Phe Ile Pro Tyr Ala
            180                 185                 190
Ile Thr Asn Met Gly Ser Ala Leu Leu Ala Ile Asp Leu Gly Leu Met
            195                 200                 205
Gly Pro Asn Tyr Ser Ile Ser Thr Ala Cys Ala Thr Ser Asn Tyr Cys
    210                 215                 220
Phe Tyr Ala Ala Ala Asn His Ile Arg Arg Gly Glu Ala Asp Leu Met
225                 230                 235                 240
Ile Ala Gly Gly Thr Glu Ala Ala Val Ile Pro Ile Gly Leu Gly Gly
                245                 250                 255
Phe Val Ala Cys Arg Ala Leu Ser Gln Arg Asn Asp Asp Pro Gln Thr
                260                 265                 270
Ala Ser Arg Pro Trp Asp Lys Asp Arg Asp Gly Phe Val Met Gly Glu
            275                 280                 285
Gly Ala Gly Val Leu Val Met Glu Ser Leu Glu His Ala Met Lys Arg
    290                 295                 300
Gly Ala Pro Ile Ile Ala Glu Tyr Leu Gly Gly Ala Val Asn Cys Asp
305                 310                 315                 320
Ala Tyr His Met Thr Asp Pro Arg Ala Asp Gly Leu Gly Val Ser Ser
                325                 330                 335
Cys Ile Glu Ser Ser Leu Glu Asp Ala Gly Val Ser Pro Glu Glu Val
                340                 345                 350
Asn Tyr Ile Asn Ala His Ala Thr Ser Thr Leu Ala Gly Asp Leu Ala
            355                 360                 365
Glu Ile Asn Ala Ile Lys Lys Val Phe Lys Asn Thr Lys Glu Ile Lys
    370                 375                 380
Ile Asn Ala Thr Lys Ser Met Ile Gly His Cys Leu Gly Ala Ser Gly
385                 390                 395                 400
Gly Leu Glu Ala Ile Ala Thr Ile Lys Gly Ile Thr Thr Gly Trp Leu
                405                 410                 415
His Pro Ser Ile Asn Gln Phe Asn Pro Glu Pro Ser Val Asp Phe Asn
            420                 425                 430
Thr Val Ala Asn Lys Lys Gln Gln His Glu Val Asn Val Ala Ile Ser
            435                 440                 445
Asn Ser Phe Gly Phe Gly Gly His Asn Ser Val Val Ala Phe Ser Ala
    450                 455                 460
Phe Lys Pro
465

<210> SEQ ID NO 13
<211> LENGTH: 2369
<212> TYPE: DNA
<213> ORGANISM: Cuphea pulcherrima

<400> SEQUENCE: 13
gtacgcctgc aggtaccggt ccggaattcc cgggtcgacc cacgcgtccg cataaaagag    60
agagagaggg atccatcgaa tgcggccacc ctcctttcat cttcgattca ttaccatacc   120
attccgctga tccatttttcc gccttttccg ggtctttcat cccaaagggt atccttttct   180
atcctatctt ctcaaagggt cagtcagttc cctccaatgc ctgccgcctc ttccctgctc   240
gcttcccctc tctgtacgtg gctccttgcc gcctgcatgt ctacctcctt ccaccccctcc   300
```

```
gaccctcttc cgccttccat ctcctctcct cgccgacgcc tctcccgccg ccggattctc      360
tcccaatgcg ccccactacc ttctgcttcc tccgccctcc gcggatccag tttccatacc      420
ctcgtcacct cttacctcgc ctgcttcgag ccctgccatg actactatac atccgcatcc      480
ttgttcggat ccagacccat tcgcaccacc cgcaggcacc ggaggctcaa tcgagcttcc      540
ccttccaggg aggcaatggc cgtggctctg caacctgaac aggaagttac cacaaagaag      600
aagccaagta tcaaacagcg gcgagtagtt gtgactggaa tgggtgtggt gactcctcta      660
ggccatgacc ctgatgtttt ctacaataat ctgcttgatg aacgagtgg cataagcgag        720
atagagacct tgattgtgc tcaatttcct acgagaattg ctggagagat caagtctttc        780
tccacagatg gttgggtggc cccgaagctc tctaagagga tggacaagtt catgctatac      840
atgctgaccg ctggcaagaa agcattaaca gatggtggaa tcaccgaaga tgtgatgaaa      900
gagctagata aagaaaatg cggagttctc attggctcag caatgggtgg aatgaaggta        960
ttcaatgatg ccattgaagc cctaaggatt tcatataaga gatgaatcc cttttgtgta       1020
cctttcgcta ccacaaatat gggatcagct atgcttgcaa tggacttggg atggatgggg     1080
cccaactact cgatatctac tgcttgtgca acgagtaact tttgtataat gaatgctgcg     1140
aaccatataa tcagaggcga agcagatgtg atgctttgcg ggggctcaga tgcggtaatc     1200
atacctattg gtatgggagg ttttgttgca tgccgagctt tgtcccagag aaattccgac     1260
cctactaaag cttcaagacc atgggacagt aatcgtgatg gatttgttat ggggggaagga    1320
gctggagtgc tactactaga ggagttggag catgcaaaga aaagaggtgc gactatttac      1380
gcagaatttc taggtgggag tttcacttgc gatgcctacc acatgaccga gcctcaccct     1440
gatggagctg gagtgattct ctgcatagag aaggctttgg ctcagtcagg agtctctagg     1500
gaagacgtaa attacataaa tgcccatgcc acatccactc cggctggaga tatcaaagag    1560
taccaagctc ttatccactg tttcggccaa acagagagt taaaagttaa ttcaaccaaa     1620
tcaatgattg gtcaccttct cggagcagcc ggtggtgtgg aagcagtttc agtagttcag     1680
gcaataagga ctgggtggat ccatccgaat attaatttgg aaaacccaga tgaaggcgtg    1740
gatacaaaat tgctcgtggg tcctaagaag gagagactga acgttaaggt cggtttgtct     1800
aattcatttg ggtttggtgg gcacaactcg tccatactct tcgcccccta catctaggac      1860
gtttccgtgt gtggaattct actcaacata tcaaagctga gttttgagg actccagcat     1920
gttggtagct ccttacgtct ctagacatgc ccatgagttt tgtgtccgga gctttagtcg      1980
gaaccatgac ggattgagta ctcatggcga cacttgatat actccttgct agaattgttg     2040
gtagagcaat attcattatc tcatattttt tttttctctg aaatctccct ccttgcaata     2100
gttgtacttt cgagcttttc atcgagtcag tgaagaagaa acaaagctg ttaactcggg       2160
cacgtagtaa ccatttgccc tttgttttgc tctctatttc atcaccgttt tgtggtttta     2220
aaatttgtaa aactagaaga ctggtttaga ttggtttgtt ttctcattga taattggggr      2280
atgtatgttt tggaaataaa aaaaaaaaa aaaaaaaaa aaaaaaaaa aaaaaaaaa         2340
aaaaaaaaaa agggcggccg ctctagagg                                       2369
```

<210> SEQ ID NO 14
<211> LENGTH: 546
<212> TYPE: PRT
<213> ORGANISM: Cuphea pulcherrima

<400> SEQUENCE: 14

Met Pro Ala Ala Ser Ser Leu Leu Ala Ser Pro Leu Cys Thr Trp Leu

-continued

```
  1               5              10              15
Leu Ala Ala Cys Met Ser Thr Ser Phe His Pro Ser Asp Pro Leu Pro
             20                  25                  30

Pro Ser Ile Ser Ser Pro Arg Arg Leu Ser Arg Arg Ile Leu
             35                  40                  45

Ser Gln Cys Ala Pro Leu Pro Ser Ala Ser Ser Ala Leu Arg Gly Ser
             50                  55                  60

Ser Phe His Thr Leu Val Thr Ser Tyr Leu Ala Cys Phe Glu Pro Cys
 65                  70                  75                  80

His Asp Tyr Tyr Thr Ser Ala Ser Leu Phe Gly Ser Arg Pro Ile Arg
                 85                  90                  95

Thr Thr Arg Arg His Arg Arg Leu Asn Arg Ala Ser Pro Ser Arg Glu
                100                 105                 110

Ala Met Ala Val Ala Leu Gln Pro Glu Gln Glu Val Thr Thr Lys Lys
                115                 120                 125

Lys Pro Ser Ile Lys Gln Arg Arg Val Val Thr Gly Met Gly Val
            130                 135                 140

Val Thr Pro Leu Gly His Asp Pro Asp Val Phe Tyr Asn Asn Leu Leu
145                 150                 155                 160

Asp Gly Thr Ser Gly Ile Ser Glu Ile Glu Thr Phe Asp Cys Ala Gln
                165                 170                 175

Phe Pro Thr Arg Ile Ala Gly Glu Ile Lys Ser Phe Ser Thr Asp Gly
                180                 185                 190

Trp Val Ala Pro Lys Leu Ser Lys Arg Met Asp Lys Phe Met Leu Tyr
            195                 200                 205

Met Leu Thr Ala Gly Lys Lys Ala Leu Thr Asp Gly Gly Ile Thr Glu
            210                 215                 220

Asp Val Met Lys Glu Leu Asp Lys Arg Lys Cys Gly Val Leu Ile Gly
225                 230                 235                 240

Ser Ala Met Gly Gly Met Lys Val Phe Asn Asp Ala Ile Glu Ala Leu
                245                 250                 255

Arg Ile Ser Tyr Lys Lys Met Asn Pro Phe Cys Val Pro Phe Ala Thr
                260                 265                 270

Thr Asn Met Gly Ser Ala Met Leu Ala Met Asp Leu Gly Trp Met Gly
            275                 280                 285

Pro Asn Tyr Ser Ile Ser Thr Ala Cys Ala Thr Ser Asn Phe Cys Ile
            290                 295                 300

Met Asn Ala Ala Asn His Ile Ile Arg Gly Glu Ala Asp Val Met Leu
305                 310                 315                 320

Cys Gly Gly Ser Asp Ala Val Ile Ile Pro Ile Gly Met Gly Gly Phe
                325                 330                 335

Val Ala Cys Arg Ala Leu Ser Gln Arg Asn Ser Asp Pro Thr Lys Ala
            340                 345                 350

Ser Arg Pro Trp Asp Ser Asn Arg Asp Gly Phe Val Met Gly Glu Gly
            355                 360                 365

Ala Gly Val Leu Leu Leu Glu Glu Leu Glu His Ala Lys Lys Arg Gly
            370                 375                 380

Ala Thr Ile Tyr Ala Glu Phe Leu Gly Gly Ser Phe Thr Cys Asp Ala
385                 390                 395                 400

Tyr His Met Thr Glu Pro His Pro Asp Gly Ala Gly Val Ile Leu Cys
                405                 410                 415

Ile Glu Lys Ala Leu Ala Gln Ser Gly Val Ser Arg Glu Asp Val Asn
            420                 425                 430
```

Tyr Ile Asn Ala His Ala Thr Ser Thr Pro Ala Gly Asp Ile Lys Glu
        435                 440                 445

Tyr Gln Ala Leu Ile His Cys Phe Gly Gln Asn Arg Glu Leu Lys Val
        450                 455                 460

Asn Ser Thr Lys Ser Met Ile Gly His Leu Leu Gly Ala Ala Gly Gly
465                 470                 475                 480

Val Glu Ala Val Ser Val Gln Ala Ile Arg Thr Gly Trp Ile His
                485                 490                 495

Pro Asn Ile Asn Leu Glu Asn Pro Asp Glu Gly Val Asp Thr Lys Leu
            500                 505                 510

Leu Val Gly Pro Lys Lys Glu Arg Leu Asn Val Lys Val Gly Leu Ser
        515                 520                 525

Asn Ser Phe Gly Phe Gly Gly His Asn Ser Ser Ile Leu Phe Ala Pro
        530                 535                 540

Tyr Ile
545

<210> SEQ ID NO 15
<211> LENGTH: 2372
<212> TYPE: DNA
<213> ORGANISM: Cuphea pulcherrima
<220> FEATURE:
<221> NAME/KEY: misc_feature
<222> LOCATION: (1)..(2300)
<223> OTHER INFORMATION: unsure at all n locations

<400> SEQUENCE: 15

```
acntggtccg gaattcccgg gtcgacccac gcgtccgcga cgccaaccca caccaaactt      60
cctcagcttc tcttctcaag acggacgcca ttggcagcag acagacagac agacagaccc     120
ataaaagaga gagagaggga tccatcgaat gcggccaccc tcctttcatc ttcgattcat     180
taccatacca ttccgctgat ccattttccg ccttttccgg gtctttcatc ccaaagggta     240
tccttttcta tcctatcttc tcaaagggtc agtcagttcc ctccaatgcc tgccgcctct     300
tccctgctcg cttcccctct ctgtacgtgg ctccttgccg cctgcatgtc tacctccttc     360
caccctccg accctcttcc gccttccatc tcctctcctc gccgacgcct ctcccgccgc     420
cggattctct cccaatgcgc cccactacct tctgcttcct ccgccctccg cggatccagt     480
ttccataccc tcgtcacctc ttacctcgcc tgcttcgagc cctgccatga ctactataca     540
tccgcatcct tgttcggatc cagacccatt cgcaccaccc gcaggcaccg gaggctcaat     600
cgagcttccc cttccagggg aggcaatggc cgtggctctg caacctgaac aggaagttac     660
cacaaagaag aagccaagta tcaaacagcg gcgagtagtt gtgactggaa tgggtgtggt     720
gactcctcta ggccatgaac ctgatgtttt tctacaataa tctgcttgat ggaacgagtg     780
gcataagcga gatagagacc tttgattgtg ctcaatttcc tacgagaatt gctggagaga     840
tcaagtcttt ctccacagat ggttgggtgg ccccgaagct ctctaagagg atggacaagt     900
tcatgctata catgctgact gctggcaaga aagcattaac agatggtgga atcaccgaag     960
atgtgatgaa agagctagat aaaagaaaat gcggagttct cattggctca gcaatgggtg    1020
gaatgaaggt attcaatgat gccattgaag ccctaaggat tcatataag aagatgaatc    1080
cctttttgtgt acctttcgct accacaaata tgggatcagc tatgcttgca atggacttgg    1140
gatggatggg gcccaactac tcgatatcta ctgcttgtgc aacgagtaac ttttgtataa    1200
tgaatgctgc gaaccatata atcagaggcg aagcagatgt gatgctttgc gggggctcag    1260
```

-continued

```
atgcggtaat catacctatt ggtatgggag gttttgttgc atgccgagct ttgtcccaga    1320
gaaattccga ccctactaaa gcttcaagac catgggacag taatcgtgat ggatttgtta    1380
tgggggaagg agctggagtg ctactactag aggagttgga gcatgcaaag aaaagaggtg    1440
cgactattta cgcagaattt ctaggtggga gtttcacttg cgatgcctac cacatgaccg    1500
agcctcaccc tgatggagct ggagtgattc tctgcataga aaggctttg gctcagtcag     1560 gagtctctag ggaagacgta aattacataa atgcccatgc cacatccact ccggctggag    1620
atatcaaaga gtaccaagct cttatccact gtttcggcca aaacagagag ttaaaagtta    1680
attcaaccaa atcaatgatt ggtcaccttc tcggagcagc cggtggtgtg aagcagtttt    1740
cagtagttca ggcaataagg actgggtgga tccatccgaa tattaatttg gaaaacccag    1800
atgaaggcgt ggatacaaaa ttgctcgtgg gtcctaagaa ggagagactg aacgttaagg    1860
tcggtttgtc taattcattt gggtttggtg ggcacaactc gtccatactc ttcgcccctt    1920
acatctagga cgtttcgtgt gtggaattct actcaacata tcaaagctga agttttgagg    1980
actccagcat gttggtagct ccttacgtct ctagacatgc ccatgagttt tgtgtccgga    2040
gctttagtcg gaaccatgac ggattagta ctcatggcga cacttgatat actccttgct     2100
agaattgttg gtagagcaat attcattatc tcatattttt tttttctctg aaatctccct    2160
ccttgcaata gttgtacttt cgagcttttc atcgagtcag tgaagaagag aacaaagctg    2220
ttaactcggg cacgtagtaa ccatttgccc tttgttttgc tctctatttc atcaccgttt    2280
tgtggtttta aaatttgtaa aactagaaga ctggtttaga ttggtttgtt ttctcaaaaa    2340
aaaaaaaaaa gggcggccgc tctagaggat cc                                  2372
```

<210> SEQ ID NO 16
<211> LENGTH: 1580
<212> TYPE: DNA
<213> ORGANISM: Cuphea hookeriana
<220> FEATURE:
<221> NAME/KEY: misc_feature
<222> LOCATION: (1)..(1578)
<223> OTHER INFORMATION: unsure at all n locations

<400> SEQUENCE: 16

```
cctgaatcgg attcaagaga gagtttcgtt gctgggatgg cgaatgcatc tgggtttctg     60
ggttcttcag ttcctgccct gagaagggca actcagcatt cgatttcatc gtctcgtgga    120
tcttcctcgg agtttgtctc caaaaggtgt ttttgctgta gtgccgttca ggattctgac    180
aggcagtctt tggtgattc tcgctcgccg aggcttgtga gtagaggatg caaattaatt     240
ggatctggtt ctgctatacc agctcttcaa gtctcaaatg atgatcttgc taaaattgtc    300
gacaccaatg atgaatggat tactgtccga acggggatcc gcaaccgaag ggttctctca    360
ggtaaagata gtcttacaaa tttagcatca gaggcagcaa ggaaagctct agagatggca    420
caggtagacg caaatgatgt ggatatggtt ttgatgtgta cttctacccc tgaggacctt    480
ttcggcagtg ctcctcagat atcgaaagca cttggctgca aaaagaatcc tttgtcttac    540
gacattaccg ctgcatgcag tggatttgtg ttgggtttag tctcagctgc ttgccacatt    600
agaggtgggg gttttaacaa tattctagtg attggtgctg attctctttc tcggtatgtt    660
gactggaccg atcggggaac atgtattctc tttggagatg ctgctggagc tgtagtggtg    720
cagtcatgtg atgctgagga agatgggctc tttgcttttg atttgcatag cgatggagat    780
gggcaaaggc atctaaaagc tgcaatcaaa gaagatgaag ttgataaagc cctgggacat    840
aatgggtcca tcagagattt tccaccaagg cgttcttcat actcttgcat ccaaatgaac    900
```

-continued

```
ggtaaagagg tattccgctt tgcttgccgc tctgtgcctc agtcaatcga atcagcactt    960
ggaaaggccg gtcttaatgg atccaacatc gactggttgc tgcttcatca ggcaaatcag   1020
aggatcattg atgcagtagc aacacgtcta gaggttcctc aagaacgaat tatctcaaac   1080
ttggcaaatt acgggaacac tagtgcggca tccattccct tggcactaga cgaagctgtg   1140
aggagtggaa atgtgaagcc gggtcacgtg attgcaaccg caggatttgg cgccggactc   1200
acatggggtt ctgctattat caggtgggga taagactgaa gccgagccag cactgcagct   1260
tcctctcaaa ccgatgtttc acgaaatttt gcttccatga ccanaaaaag aagaagtcag   1320
tcttttatgg agcaagcaac acgacacgat cttcatcaca ttgcccttt tcgttcccct    1380 tttccattag tttgatgatt ttgctgacaa tacaataccc atagtttctt ttgtccccaa   1440
taagttattt gtttcttgtt taattgttca gcttttactt cattttgtct cgggacattg   1500
gagatgacag cataaacatc atgtttatat tttgctaaaa aaaaaaaaaa aaaaaaaaa    1560 aaaaaaaaaa aaaaaaaaa                                               1580
```

<210> SEQ ID NO 17
<211> LENGTH: 398
<212> TYPE: PRT
<213> ORGANISM: Cuphea hookeriana

<400> SEQUENCE: 17

```
Met Ala Asn Ala Ser Gly Phe Leu Gly Ser Val Pro Ala Leu Arg
1               5                   10                  15

Arg Ala Thr Gln His Ser Ile Ser Ser Arg Gly Ser Ser Ser Glu
                20                  25                  30

Phe Val Ser Lys Arg Val Phe Cys Cys Ser Ala Val Gln Asp Ser Asp
                35                  40                  45

Arg Gln Ser Leu Gly Asp Ser Arg Ser Pro Arg Leu Val Ser Arg Gly
        50                  55                  60

Cys Lys Leu Ile Gly Ser Gly Ser Ala Ile Pro Ala Leu Gln Val Ser
65                  70                  75                  80

Asn Asp Asp Leu Ala Lys Ile Val Asp Thr Asn Asp Glu Trp Ile Thr
                85                  90                  95

Val Arg Thr Gly Ile Arg Asn Arg Arg Val Leu Ser Gly Lys Asp Ser
                100                 105                 110

Leu Thr Asn Leu Ala Ser Glu Ala Ala Arg Lys Ala Leu Glu Met Ala
        115                 120                 125

Gln Val Asp Ala Asn Asp Val Asp Met Val Leu Met Cys Thr Ser Thr
    130                 135                 140

Pro Glu Asp Leu Phe Gly Ser Ala Pro Gln Ile Ser Lys Ala Leu Gly
145                 150                 155                 160

Cys Lys Lys Asn Pro Leu Ser Tyr Asp Ile Thr Ala Ala Cys Ser Gly
                165                 170                 175

Phe Val Leu Gly Leu Val Ser Ala Ala Cys His Ile Arg Gly Gly Gly
            180                 185                 190

Phe Asn Asn Ile Leu Val Ile Gly Ala Asp Ser Leu Ser Arg Tyr Val
        195                 200                 205

Asp Trp Thr Asp Arg Gly Thr Cys Ile Leu Phe Gly Asp Ala Ala Gly
    210                 215                 220

Ala Val Val Val Gln Ser Cys Asp Ala Glu Glu Asp Gly Leu Phe Ala
225                 230                 235                 240

Phe Asp Leu His Ser Asp Gly Asp Gly Gln Arg His Leu Lys Ala Ala
```

-continued

```
                        245                      250                          255
Ile Lys Glu Asp Glu Val Asp Lys Ala Leu Gly His Asn Gly Ser Ile
            260                      265                      270

Arg Asp Phe Pro Pro Arg Arg Ser Ser Tyr Ser Cys Ile Gln Met Asn
            275                      280                      285

Gly Lys Glu Val Phe Arg Phe Ala Cys Arg Ser Val Pro Gln Ser Ile
            290                      295                      300

Glu Ser Ala Leu Gly Lys Ala Gly Leu Asn Gly Ser Asn Ile Asp Trp
305                      310                      315                      320

Leu Leu Leu His Gln Ala Asn Gln Arg Ile Ile Asp Ala Val Ala Thr
                325                      330                      335

Arg Leu Glu Val Pro Gln Glu Arg Ile Ile Ser Asn Leu Ala Asn Tyr
            340                      345                      350

Gly Asn Thr Ser Ala Ala Ser Ile Pro Leu Ala Leu Asp Glu Ala Val
            355                      360                      365

Arg Ser Gly Asn Val Lys Pro Gly His Val Ile Ala Thr Ala Gly Phe
        370                      375                      380

Gly Ala Gly Leu Thr Trp Gly Ser Ala Ile Ile Arg Trp Gly
385                      390                      395
```

What is claimed is:

1. A method for producing medium-chain fatty acids in transgenic plant seeds by expression of one or more plant medium-chain thioesterase proteins heterologous to said transgenic plant, comprising
    (a) providing for expression of a plant synthase factor protein heterologous to said transgenic plant, wherein said synthase is a β-ketoacyl-ACP synthase (KAS) factor A protein from a *Cuphea* species:
    (b) providing for expression of said one or more plant medium-chain thioesterase proteins in conjunction with (a),
    whereby the percentage of medium-chain fatty acids produced in said transgenic plant seeds expressing both said plant synthase factor protein and said one or more plant medium-chain thioesterase proteins is increased as compared to the percentage of medium-chain fatty acids produced in seeds expressing only said one or more plant medium-chain thioesterase proteins.

2. The method of claim 1, wherein said *Cuphea* species is *C. hookeriana* or *C. pulcherrima*.

3. The method of claim 2 wherein said KAS factor A protein comprises a coding sequence as set forth in SEQ ID NO:5.

4. The method of claim 2 wherein said KAS factor A protein comprises a coding sequence encoding an amino acid sequence as set forth in SEQ ID NO:6.

5. The method of claim 2 wherein said synthase factor A protein comprises a coding sequence encoding an amino acid sequence set forth in residues 125-466 of SEQ ID NO:6.

* * * * *